(12) United States Patent
Mahfouz

(10) Patent No.: US 11,744,650 B2
(45) Date of Patent: Sep. 5, 2023

(54) METHODS AND DEVICES FOR KNEE SURGERY WITH INERTIAL SENSORS

(71) Applicant: TechMah Medical LLC, Cincinnati, OH (US)

(72) Inventor: Mohamed R. Mahfouz, Knoxville, TN (US)

(73) Assignee: TECHMAH MEDICAL LLC, Knoxville, TN (US)

( * ) Notice: Subject to any disclaimer, the term of this patent is extended or adjusted under 35 U.S.C. 154(b) by 340 days.

(21) Appl. No.: 17/177,353

(22) Filed: Feb. 17, 2021

(65) Prior Publication Data
US 2021/0236210 A1     Aug. 5, 2021

Related U.S. Application Data

(63) Continuation of application No. 16/447,021, filed on Jun. 20, 2019, now Pat. No. 11,284,945.
(Continued)

(51) Int. Cl.
*A61B 34/20*     (2016.01)
*A61B 34/10*     (2016.01)
(Continued)

(52) U.S. Cl.
CPC ............ *A61B 34/20* (2016.02); *A61B 5/4528* (2013.01); *A61B 34/10* (2016.02); *A61B 34/30* (2016.02);
(Continued)

(58) Field of Classification Search
None
See application file for complete search history.

(56) References Cited

U.S. PATENT DOCUMENTS

| 7,640,106 B1 | 12/2009 | Stokar et al. |
| 8,425,524 B2 * | 4/2013 | Aker ................. A61B 17/157 |
| | | 606/88 |

(Continued)

FOREIGN PATENT DOCUMENTS

| CA | 2933235 | 6/2015 |
| WO | 2015089118 | 6/2015 |
| WO | 2019246357 | 12/2019 |

OTHER PUBLICATIONS

European Patent Office, Extended European Search Report in EP 19823476.7, dated Jun. 24, 2021.
(Continued)

*Primary Examiner* — Christian A Sevilla
(74) *Attorney, Agent, or Firm* — ALLEN, DYER, DOPPELT + GILCHRIST, P.A. Attorneys at Law

(57) ABSTRACT

A method of navigating a cutting instrument, via a computer system, the method comprising: (a) mounting a patient-specific anatomical mapper (PAM) to a human in a single known location and orientation, where the PAM includes a surface precisely and correctly mating with a human surface correctly in only a single location and orientation; (b) mounting a reference inertial measurement unit (IMU) to the human; (c) operatively coupling a guide to the PAM, where the guide includes an instrument inertial measurement unit (IMU) and at least one of a cutting slot and a pin orifice; (d) outputting data from the reference IMU and the instrument IMU indicative of changes in position and orientation of the guide with respect to the human; (e) repositioning the guide with respect to the human to a position and an orientation consistent with a plan for carrying out at least one of a cut and pin placement; and, (f) visually displaying feedback concerning the position and orientation of the guide with respect to the human using data output from the reference
(Continued)

IMU and the instrument IMU, which data is processed by a computer program and the computer program directs the visually displayed feedback.

30 Claims, 30 Drawing Sheets

Related U.S. Application Data

(60) Provisional application No. 62/687,462, filed on Jun. 20, 2018.

(51) Int. Cl.
| | |
|---|---|
| A61B 5/00 | (2006.01) |
| A61B 34/30 | (2016.01) |
| A61F 2/38 | (2006.01) |
| A61F 2/46 | (2006.01) |
| A61B 5/11 | (2006.01) |
| A61B 17/15 | (2006.01) |

(52) U.S. Cl.
CPC .......... *A61F 2/3859* (2013.01); *A61F 2/3868* (2013.01); *A61F 2/461* (2013.01); *A61F 2/4657* (2013.01); *A61F 2/4684* (2013.01); *A61B 5/1121* (2013.01); *A61B 17/154* (2013.01); *A61B 2034/102* (2016.02); *A61B 2034/105* (2016.02); *A61B 2034/107* (2016.02); *A61B 2034/108* (2016.02); *A61B 2034/2048* (2016.02); *A61B 2034/2055* (2016.02); *A61B 2034/2072* (2016.02); *A61B 2562/0219* (2013.01); *A61B 2562/0223* (2013.01); *A61F 2002/4633* (2013.01)

(56) References Cited

U.S. PATENT DOCUMENTS

| | | | | |
|---|---|---|---|---|
| 10,363,149 | B2* | 7/2019 | van der Walt | A61F 2/4657 |
| 2001/0034530 | A1* | 10/2001 | Malackowski | A61B 34/20 |
| | | | | 606/130 |
| 2006/0058616 | A1* | 3/2006 | Marquart | A61B 34/20 |
| | | | | 600/407 |
| 2006/0064005 | A1 | 3/2006 | Triano et al. | |
| 2008/0081982 | A1* | 4/2008 | Simon | A61B 34/25 |
| | | | | 600/407 |
| 2009/0222014 | A1* | 9/2009 | Bojarski | A61B 17/1746 |
| | | | | 606/88 |
| 2009/0248044 | A1 | 10/2009 | Amiot et al. | |
| 2010/0310141 | A1 | 12/2010 | Wilson | |
| 2011/0208093 | A1 | 8/2011 | Gross et al. | |
| 2011/0275957 | A1 | 11/2011 | Bhandari | |
| 2011/0320153 | A1 | 12/2011 | Lightcap et al. | |
| 2012/0221008 | A1 | 8/2012 | Carroll | |
| 2013/0217998 | A1 | 8/2013 | Mahfouz et al. | |
| 2015/0157416 | A1 | 6/2015 | Andersson | |
| 2016/0157751 | A1 | 6/2016 | Mahfouz | |
| 2016/0361101 | A1* | 12/2016 | Moctezuma de la Barrera | |
| | | | | A61B 17/809 |
| 2017/0132389 | A1 | 5/2017 | McCaulley et al. | |
| 2017/0367766 | A1 | 12/2017 | Mahfouz | |
| 2019/0000559 | A1 | 1/2019 | Berman et al. | |
| 2019/0000576 | A1 | 1/2019 | Mintz et al. | |
| 2019/0070011 | A1 | 3/2019 | Fanson et al. | |
| 2019/0350728 | A1 | 11/2019 | van der Walt et al. | |
| 2020/0196908 | A1 | 6/2020 | Ben-haim et al. | |
| 2020/0197112 | A1 | 6/2020 | Chin et al. | |
| 2020/0261163 | A1 | 8/2020 | Helm et al. | |
| 2021/0000548 | A1 | 1/2021 | Mahfouz | |
| 2021/0000612 | A1 | 1/2021 | Mahfouz | |

OTHER PUBLICATIONS

ISA/US International Search Report and Written Opinion in PCT/US2014/069411, dated Apr. 23, 2015.
Japan Patent Office, office action in JP 2016-538056, dated Dec. 26, 2017.
Canadian Intellectual Property Office, office action in CA 2933235, dated Sep. 28, 2017.
Canadian Intellectual Property Office, office action in CA 2933235, dated Jul. 3, 2018.
Salamon, Accurate Tilt Estimation of a Rotating Platform Using Inertial Sensing, Drexel University, Jun. 2014.
ST Microelectronics, LSM303DLH, Dec. 2009.
TO, Quaternionic Attitude Estimation with Inertial Measuring Unit for Robotic and Human Body Motion Tracking using Sequential Monte Carlo Methods with Hyper-Dimensional Spherical Distributions, University of Tennessee, Knoxville, Dec. 2012.
ISA/US International Search Report and Written Opinion in PCT/US19/38164, dated Sep. 9, 2019.

* cited by examiner

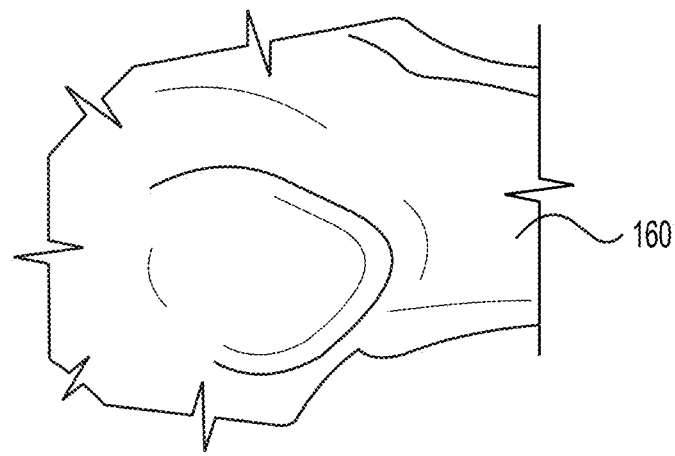
FIG. 31
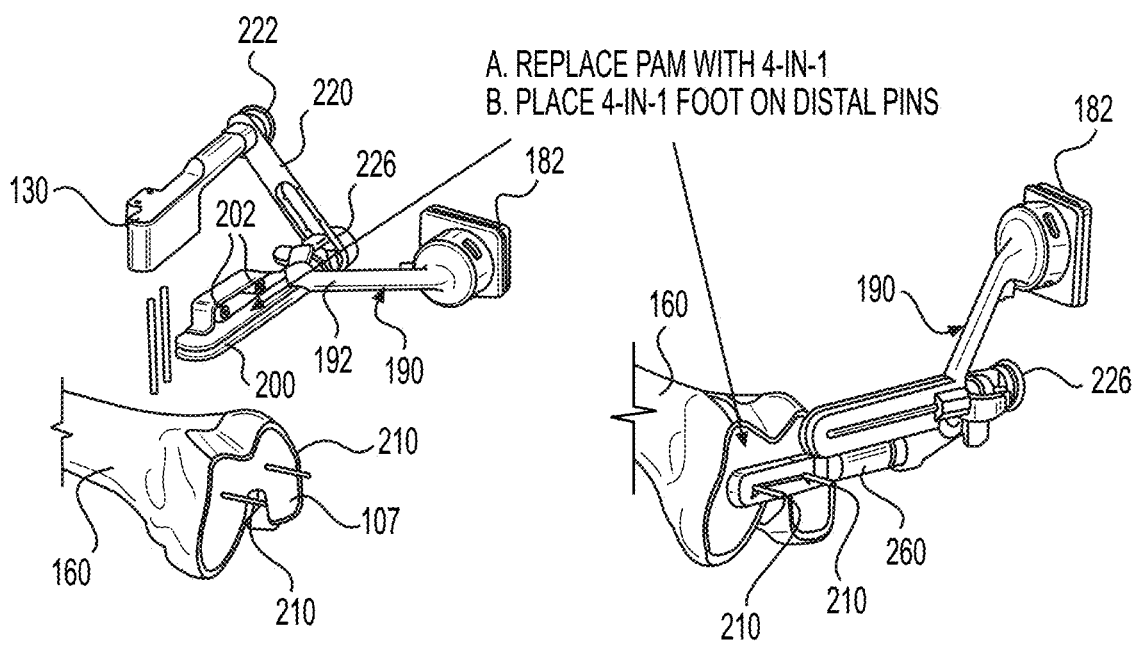
FIG. 32  FIG. 33

METHODS AND DEVICES FOR KNEE SURGERY WITH INERTIAL SENSORS

CROSS REFERENCE TO RELATED APPLICATIONS

The present application is a continuation of U.S. patent application Ser. No. 16/447,021, titled METHODS AND DEVICES FOR KNEE SURGERY WITH INERTIAL SENSORS," filed Jun. 20, 2019, now U.S. Pat. No. 11,284,945, which claimed the benefit of U.S. Provisional Patent Application Ser. No. 62/687,462, titled "METHODS AND DEVICES FOR KNEE SURGERY WITH INERTIAL SENSORS," filed Jun. 20, 2018, the disclosure of each of which is incorporated herein by reference.

INTRODUCTION TO THE INVENTION

The present disclosure is directed to devices, methods, and techniques related to computer aided surgery and computer planned surgery.

Computer aided surgery has been shown to improve precision of orthopedic surgery in most large joints, specifically hip and knee joints. Conventional knee replacement surgery requires several surgical trays with a plethora of unique surgical instruments, where each surgical tray is expensive, heavy, and requires sterilization for reuse. Technology has been developed in the field of computer aided surgery to reduce the number of instruments while maintaining or slightly improving precision. Current configurations of such technologies include surgical robotics, optical navigation, and inertial sensor-based instrumentation.

Each of these current systems has inherent advantages and disadvantages. For example, robotic systems are expensive, bulky, and often require significant time to setup, tear down, and execute the surgical procedure. Optical systems are also expensive, suffer from line-of-sight issues, and require similar time as robotics to setup and tear down. Inertial systems, in most of their current forms, require significant manual instrumentation to constrain the degrees of freedom due to shortcomings in the technology, often requiring at least one or two instrument trays. Therefore, there is a need for technology to improve surgical precision without the cost, space constraints, and capital equipment requirements of current technologies.

What is disclosed herein are techniques, methods, and devices as part of a computer aided surgical navigation system for the knee joint surgeries and instrumentation to support the same so that the navigation system may be delivered in a "just-in-time" manner with minimal instrumentation.

It is a first aspect of the present invention to provide a method of navigating a cutting instrument, via a computer system, the method comprising: (a) mounting a patient-specific anatomical mapper (PAM) to a human in a single known location and orientation, where the PAM includes a surface precisely and correctly mating with a human surface correctly in only a single location and orientation; (b) mounting a reference inertial measurement unit (IMU) to the human; (c) operatively coupling a guide to the PAM, where the guide includes an instrument inertial measurement unit (IMU) and at least one of a cutting slot and a pin orifice; (d) outputting data from the reference IMU and the instrument IMU indicative of changes in position and orientation of the guide with respect to the human; (e) repositioning the guide with respect to the human to a position and an orientation consistent with a plan for carrying out at least one of a cut and pin placement; and, (f) visually displaying feedback concerning the position and orientation of the guide with respect to the human using data output from the reference IMU and the instrument IMU, which data is processed by a computer program and the computer program directs the visually displayed feedback.

In a more detailed embodiment of the first aspect, the PAM is mounted to at least one of a tibia and a femur. In yet another more detailed embodiment, the reference IMU is mounted to at least one of a tibia and a femur. In a further detailed embodiment, operatively coupling the guide to the PAM includes using a mechanical connection comprising at least two joints to allow repositioning of the cutting guide independent of the PAM. In still a further detailed embodiment, the at least two joints comprise at least one of a revolute joint and a spherical joint. In a more detailed embodiment, the at least two joints comprise a pair of revolute joints and a spherical joint. In a more detailed embodiment, the method further includes registering the reference IMU with respect to the instrument IMU while at least one of the reference IMU and the instrument IMU is in a known position and orientation with respect to the human. In another more detailed embodiment, the instrument IMU is mountable to the guide in only a single known location and orientation. In yet another more detailed embodiment, the reference IMU is mountable to the patient in a plurality of locations and orientations. In still another more detailed embodiment, registering the reference IMU with respect to the instrument IMU includes holding the IMUs stationary with respect to one another for a predetermined period of time.

In yet another more detailed embodiment of the first aspect, repositioning the guide with respect to the human includes repositioning the guide with respect to the PAM. In yet another more detailed embodiment, the method further includes performing an evaluation using a load measuring device operatively coupled to the instrument IMU to assess knee joint laxity. In a further detailed embodiment, the plan comprises a plan for placing the pin. In still a further detailed embodiment, visually displaying feedback includes displaying a virtual model of patient anatomy and reference indicia reflecting a position of the guide with respect to the patient anatomy. In a more detailed embodiment, visually displaying feedback includes displaying a virtual model of patient anatomy and reference indicia reflecting an intended location for the cut on the virtual model. In a more detailed embodiment, the method further includes mounting at least one pin to a resected aspect of the patient, orienting a static cutting guide with respect to the patient using the at least one pin, and mounting the static cutting guide to the patient post orienting the static cutting guide. In another more detailed embodiment, the method further includes mounting at least one pin to a resected aspect of the patient, orienting a guide foot with respect to the patient using the at least one pin, mounting the guide foot to the patient post orienting the guide foot, discontinuing the operative coupling between the PAM and guide, and operatively coupling the guide to the guide foot.

It is a second aspect of the present invention to provide a surgical equipment system comprising: (a) a first inertial measurement unit (IMU) having a gyroscope, an accelerometer, and a magnetometer; (b) a second inertial measurement unit (IMU) having a gyroscope, an accelerometer, and a magnetometer, the second IMU configured to be mounted to a reference device, where the reference device is configured to be mounted to patient anatomy; (c) a patient-specific anatomical mapper (PAM) that includes a surface precisely and correctly mating with a patient anatomy surface in only a single location and orientation, where the PAM is configured to be mounted to the patient anatomy surface; and, (d) a guide configured to be operatively coupled to the PAM when in use, the guide including at least one of a cutting slot and a pin orifice, the guide configured to couple to the first IMU in a predetermined known position and orientation.

In a more detailed embodiment of the second aspect, the system further includes a controller including software having preloaded at least one virtual anatomical model of the patient anatomy and a pre-operative surgical plan indicating the position and orientation of an intended bone resection with respect to the at least one virtual anatomical model of the patient anatomy, the controller configured to be communicatively coupled to the first and second IMUs to receive IMU data and to translate the received IMU data to determine the position and orientation of the guide with respect to the patient anatomy and output instructions for a display to visually represent the virtual anatomical model of the patient anatomy and provide guidance as to whether the guide is positioned with respect to the patient anatomy consistent with the pre-operative surgical plan to achieve the intended bone resection. In yet another more detailed embodiment, the patient-specific anatomical mapper is configured to engage at least one of a proximal tibia and a distal femur. In a further detailed embodiment, the patient-specific anatomical mapper comprises a first tibia PAM and a second femur PAM. In still a further detailed embodiment, the system further includes a mechanical connection operative to couple the guide to the PAM, the mechanical connection including at least one joint. In a more detailed embodiment, the at least one joint comprises at least two joints. In a more detailed embodiment, the at least two joints include a revolute joint and a spherical joint. In another more detailed embodiment, the at least two joints include a pair of revolute joints. In yet another more detailed embodiment, the mechanical connection is configured to concurrently mount to a first predetermined location of the PAM and a second predetermined location of the guide to assume a registration position and orientation. In still another more detailed embodiment, the system further includes a load measuring device configured to couple to the first IMU in a known position and orientation.

In yet another more detailed embodiment of the second aspect, the load measuring device comprises at least one of a plurality of piezoresistive sensors, a plurality of capacitive sensors, and a plurality of piezoelectric based strain sensors. In yet another more detailed embodiment, the system further comprises an orthopedic implant placement device configured to couple to the first IMU in a known position and orientation. In a further detailed embodiment, the orthopedic implant placement device is configured to couple to an orthopedic implant in a predetermined location and orientation, where the orthopedic implant comprises at least one of an orthopedic trial and a final orthopedic implant. In still a further detailed embodiment, the orthopedic implant comprises at least one of a tibial implant and a femoral implant as part of at least one of a knee replacement surgery or a knee revision surgery. In a more detailed embodiment, the system further includes a display communicatively coupled to the controller, the display operative to visually represent the virtual anatomical model of the patient anatomy and provide guidance as to whether the guide is positioned with respect to the patient anatomy consistent with the pre-operative surgical plan to achieve the intended bone resection. In a more detailed embodiment, the display comprises a plurality of display windows. In another more detailed embodiment, each of the plurality of display windows is associated with a stand-alone screen. In yet another more detailed embodiment, the system further comprises an orthopedic implant comprising at least one of a final orthopedic implant and an orthopedic trial. In still another more detailed embodiment, the final orthopedic implant comprises a component of a total knee joint replacement or a partial knee joint replacement.

In a more detailed embodiment of the second aspect, the final orthopedic implant comprises at least one of a patient-specific femoral component and a patient-specific tibial component of a total knee replacement. In yet another more detailed embodiment, the system further includes a guide foot configured to be operatively coupled to the guide when the guide foot is mounted to the patient anatomy in order to facilitate at least one bone cut.

It is a third aspect of the present invention to provide a method of using inertial measurement units to facilitate three dimensional tracking of a surgical tool, via a computer system, the method comprising: (a) mounting a first inertial measurement unit (IMU) to a first mammalian tissue so that the first IMU is not repositionable with respect to the first mammalian tissue; (b) operatively coupling a second inertial measurement unit (IMU) to the first mammalian tissue by using a patient-specific anatomical mapper (PAM) having a surface precisely and correctly mating with a surface of the first mammalian tissue in only a single location and orientation, the second IMU being repositionable with respect to the first mammalian tissue; (c) registering the position and orientation of the second IMU with respect to the first mammalian tissue and the first IMU while the PAM is mounted to the first mammalian tissue; (d) mounting the second IMU to a surgical tool; and, (e) tracking a position and an orientation of the surgical tool and first mammalian tissue in three dimensions while the second IMU is mounted to the surgical tool and repositionably coupled to the PAM.

In a more detailed embodiment of the third aspect, the method further comprises visually displaying feedback concerning the position and orientation of the surgical tool with respect to the first mammalian tissue using data output from the first and second IMUs, which data is processed by a computer program and the computer program directs the visually displayed feedback. In yet another more detailed embodiment, the feedback comprises a virtual model of the first mammalian tissue and first indicia on the virtual model indicating the relative real-world position of the surgical tool with respect to the first mammalian tissue. In a further detailed embodiment, the feedback further comprises a second indicia on the virtual model indicating an intended position of the surgical tool with respect to the first mammalian tissue consistent with a predetermined plan. In still a further detailed embodiment, the PAM is mounted to at least one of a tibia and a femur. In a more detailed embodiment, the first mammalian tissue comprises at least one of a tibia and a femur. In a more detailed embodiment, the surgical tool is operatively coupled to the PAM. In another more detailed embodiment, operatively coupling the surgical tool to the PAM includes using a mechanical connection comprising at least two joints to allow repositioning of the surgical tool independent of the PAM. In yet another more detailed embodiment, the at least two joints comprise at least one of a revolute joint and a spherical joint. In still another more detailed embodiment, the at least two joints comprise a pair of revolute joints and a spherical joint.

In yet another more detailed embodiment of the third aspect, the second IMU is mountable to the surgical tool in only a single known location and orientation. In yet another more detailed embodiment, the first IMU is mountable to the first mammalian tissue in a plurality of locations and orientations. In a further detailed embodiment, the position and orientation of the second IMU with respect to the first mammalian tissue includes holding the first and second IMUs stationary with respect to one another for a predetermined period of time. In still a further detailed embodiment, the method further includes performing an evaluation using a load measuring device operatively coupled to the second IMU to assess knee joint laxity.

It is a fourth aspect of the present invention to provide a surgical equipment kit for a knee replacement or revision procedure comprising: (a) a first inertial measurement unit (IMU) having a gyroscope, an accelerometer, and a magnetometer, (b) a second inertial measurement unit (IMU) having a gyroscope, an accelerometer, and a magnetometer; (c) a tibial patient-specific anatomical mapper (PAM) that includes a surface precisely and correctly mating with a tibial surface in only a single location and orientation, where the tibial PAM is configured to be mounted to the tibial surface; and, (d) a femoral patient-specific anatomical mapper (PAM) that includes a surface precisely and correctly mating with a femoral surface in only a single location and orientation, where the femoral PAM is configured to be mounted to the femoral surface, where the second IMU is configured to be operatively coupled to at least one of the tibial PAM and the femoral PAM.

In a more detailed embodiment of the fourth aspect, the kit further includes a cutting guide configured to be repositionably coupled to at least one of the tibial PAM and the femoral PAM, the cutting guide including at least one of a cutting slot and a pin orifice, the guide configured to couple to the first IMU in a predetermined known position and orientation. In yet another more detailed embodiment, the kit further includes a mechanical connection comprising at least two joints to operatively couple the cutting guide to at least one of the tibial PAM and the femoral PAM. In a further detailed embodiment, the orthopedic implant comprises a non-patient-specific implant. In still a further detailed embodiment, the non-patient-specific implant includes a femoral condyle and a tibial tray insert. In a more detailed embodiment, the non-patient-specific implant includes a femoral implant having a pair of condyles and a tibial tray insert having a pair of condyle receivers. In a more detailed embodiment, the kit further includes a reference housing configured to be rigidly mounted to at least one of a tibia and a femur, the reference housing configured to mount to the first IMU correctly in only a single position and orientation. In another more detailed embodiment, the kit further includes a 4-in-1 static cutting block. In yet another more detailed embodiment, the kit further includes a 4-in-1 reconfigurable cutting block. In still another more detailed embodiment, the kit further includes a physical memory device upon which is stored computer readable code that, when executed by a computer, is operative to provide surgical navigation guidance consistent with a pre-operative plan.

In yet another more detailed embodiment of the fourth aspect, the mass customized implant includes a femoral implant having a pair of condyles and a tibial tray insert having a pair of condyle receivers. In yet another more detailed embodiment, the at least two joints comprise at least one of a revolute joint and a spherical joint. In a further detailed embodiment, the at least two joints comprise a pair of revolute joints and a spherical joint. In still a further detailed embodiment, the kit further includes an orthopedic implant configured to replace at least a portion of a knee joint. In a more detailed embodiment, the orthopedic implant comprises a patient-specific implant. In a more detailed embodiment, the patient-specific implant includes a femoral condyle and a tibial tray insert. In another more detailed embodiment, the patient-specific implant includes a femoral implant having a pair of condyles and a tibial tray insert having a pair of condyle receivers. In yet another more detailed embodiment, the orthopedic implant comprises a mass customized implant. In still another more detailed embodiment, the mass customized implant includes a femoral condyle and a tibial tray insert. In yet another more detailed embodiment, the kit includes a copy of an internet address that may be accessed to provide stored computer readable code that, when executed by a computer, is operative to provide surgical navigation guidance consistent with a pre-operative plan.

It is a fifth aspect of the present invention to provide a surgical equipment kit for a knee replacement or revision procedure comprising: (a) a tibial patient-specific anatomical mapper (PAM) that includes a surface precisely and correctly mating with a tibial surface in only a single location and orientation, where the tibial PAM is configured to be mounted to the tibial surface; and, (b) a femoral patient-specific anatomical mapper (PAM) that includes a surface precisely and correctly mating with a femoral surface in only a single location and orientation, where the femoral PAM is configured to be mounted to the femoral surface.

In a more detailed embodiment of the fifth aspect, the kit further includes a first inertial measurement unit (IMU) having a gyroscope, an accelerometer, and a magnetometer, a second inertial measurement unit (IMU) having a gyroscope, an accelerometer, and a magnetometer, where the second IMU is configured to be operatively coupled to at least one of the tibial PAM and the femoral PAM. In yet another more detailed embodiment, the kit further includes a cutting guide configured to be repositionably coupled to at least one of the tibial PAM and the femoral PAM, the cutting guide including at least one of a cutting slot and a pin orifice, the guide configured to couple to the first IMU in a predetermined known position and orientation. In a further detailed embodiment, the kit further includes a mechanical connection comprising at least two joints to operatively couple the cutting guide to at least one of the tibial PAM and the femoral PAM. In still a further detailed embodiment, the at least two joints comprise at least one of a revolute joint and a spherical joint. In a more detailed embodiment, the at least two joints comprise a pair of revolute joints and a spherical joint. In a more detailed embodiment, the kit further includes an orthopedic implant configured to replace at least a portion of a knee joint. In another more detailed embodiment, the orthopedic implant comprises a patient-specific implant.

In a more detailed embodiment of the fifth aspect, the patient-specific implant includes a femoral condyle and a tibial tray insert. In yet another more detailed embodiment, the patient-specific implant includes a femoral implant having a pair of condyles and a tibial tray insert having a pair of condyle receivers. In a further detailed embodiment, the orthopedic implant comprises a mass customized implant. In still a further detailed embodiment, the mass customized implant includes a femoral condyle and a tibial tray insert. In a more detailed embodiment, the mass customized implant includes a femoral implant having a pair of condyles and a tibial tray insert having a pair of condyle receivers. In a more detailed embodiment, the orthopedic implant comprises a non-patient-specific implant. In another more detailed embodiment, the non-patient-specific implant includes a femoral condyle and a tibial tray insert. In yet another more detailed embodiment, the non-patient-specific implant includes a femoral implant having a pair of condyles and a tibial tray insert having a pair of condyle receivers. In still another more detailed embodiment, the kit further includes a reference housing configured to be rigidly mounted to at least one of a tibia and a femur, the reference housing configured to mount to the first IMU correctly in only a single position and orientation.

In yet another more detailed embodiment of the fifth aspect, the kit further includes a 4-in-1 static cutting block. In yet another more detailed embodiment, the kit further includes a 4-in-1 reconfigurable cutting block. In a further detailed embodiment, the kit further includes a physical memory device upon which is stored computer readable code that, when executed by a computer, is operative to provide surgical navigation guidance consistent with a pre-operative plan. In still a further detailed embodiment, the kit further includes a copy of an internet address that may be accessed to provide stored computer readable code that, when executed by a computer, is operative to provide surgical navigation guidance consistent with a pre-operative plan. In a more detailed embodiment, the kit further includes a load measuring device configured to couple to the first IMU in a known position and orientation. In a more detailed embodiment, the load measuring device comprises at least one of a plurality of piezoresistive sensors, a plurality of capacitive sensors, and a plurality of piezoelectric based strain sensors. In another more detailed embodiment, the kit further includes an orthopedic implant placement device configured to couple to the second IMU in a known position and orientation. In yet another more detailed embodiment, the orthopedic implant placement device is configured to correctly couple to an orthopedic implant in only a predetermined location and orientation.

It is a sixth aspect of the present invention to provide a surgical navigation system comprising: (a) a tibial patient-specific anatomical mapper (PAM) that includes a surface precisely and correctly mating with a tibial surface in only a single location and orientation, where the tibial PAM is configured to be mounted to the tibial surface; (b) a femoral patient-specific anatomical mapper (PAM) that includes a surface precisely and correctly mating with a femoral surface in only a single location and orientation, where the femoral PAM is configured to be mounted to the femoral surface; (c) a first inertial measurement unit (IMU) having a gyroscope, a plurality of accelerometers, and a magnetometer; (d) a first transmitter communicatively coupled to the first IMU; (e) a second inertial measurement unit (IM U) having a gyroscope, a plurality of accelerometers, and a magnetometer; (f) a second transmitter communicatively coupled to the second IMU; (g) a first signal receiver communicatively coupled to the first and second transmitters; (h) a cutting guide configured to be operatively coupled to at least one of the tibial PAM and the femoral PAM, the guide including at least one of a cutting slot and a pin orifice, the cutting guide configured to couple to the first IMU correctly in only a single position and orientation; and, (i) a controller communicatively coupled to the first signal receiver, the controller including software having access to a virtual model of patient anatomy and a pre-operative surgical plan indicating intended resection cuts with respect to the virtual model.

In a more detailed embodiment of the sixth aspect, the system further includes a visual display communicatively coupled to the controller, wherein the controller software configured to process data from the first and second IMUs to determine the position and orientation of the cutting guide with respect to the patient anatomy and output instructions for the visual display to visually represent the virtual model of the patient anatomy and provide guidance as to whether the cutting guide is positioned with respect to the patient anatomy consistent with the pre-operative surgical plan to achieve the intended resection cuts. In yet another more detailed embodiment, the tibial PAM is configured to engage a proximal portion of a tibia and the femoral PAM is configured to engage a distal portion of the femur. In a further detailed embodiment, the system further includes a mechanical connection operative to couple the cutting guide to at least one of the tibial PAM and the femoral PAM, the mechanical connection including at least one joint. In still a further detailed embodiment, the at least one joint comprises at least two joints. In a more detailed embodiment, the at least two joints include a revolute joint and a spherical joint. In a more detailed embodiment, the at least two joints include a pair of revolute joints. In another more detailed embodiment, the mechanical connection is configured to concurrently mount to a first predetermined location of at least one of the tibial PAM and the femoral PAM and a second predetermined location of the cutting guide to assume a registration position and orientation.

In a more detailed embodiment of the sixth aspect, the system further includes a load measuring device configured to couple to the first IMU in a known position and orientation. In yet another more detailed embodiment, the load measuring device comprises at least one of a plurality of piezoresistive sensors, a plurality of capacitive sensors, and a plurality of piezoelectric based strain sensors. In a further detailed embodiment, the system further includes an orthopedic implant placement device configured to couple to the first IMU in a known position and orientation. In still a further detailed embodiment, the orthopedic implant placement device is configured to couple to an orthopedic implant in a predetermined location and orientation, where the orthopedic implant comprises at least one of an orthopedic trial and a final orthopedic implant. In a more detailed embodiment, the orthopedic implant comprises at least one of a tibial implant and a femoral implant as part of at least one of a knee replacement surgery or a knee revision surgery. In a more detailed embodiment, the visual display comprises a plurality of display windows. In another more detailed embodiment, each of the plurality of display windows is associated with a stand-alone screen. In yet another more detailed embodiment, the system further includes an orthopedic implant comprising at least one of a final orthopedic implant and an orthopedic trial. In still another more detailed embodiment, the final orthopedic implant comprises a component of a total knee joint replacement or a partial knee joint replacement. In yet another more detailed embodiment, the final orthopedic implant comprises at least one of a patient-specific femoral component and a patient-specific tibial component of a total knee replacement. In yet another more detailed embodiment, the system further includes a guide foot configured to be operatively coupled to the cutting guide when the guide foot is mounted to the patient anatomy in order to facilitate at least one bone cut.

It is a seventh aspect of the present invention to provide a method of conducting a surgical procedure, the surgical procedure comprising repositioning a cutting guide using navigation guidance displayed on a visual display, the cutting guide including a first inertial measurement unit (IMU), the cutting guide operatively coupled to a femoral patient-specific anatomical mapper (PAM) that includes a surface precisely and correctly mating with a femoral surface in only a single location and orientation, where the navigation guidance includes at least one of a virtual model of the cutting guide and a virtual model of a patient femur, as well as an indication regarding a three dimensional position of the cutting guide with respect to the patient femur using data from the first IMU, where the navigation guidance also includes guidance for repositioning the cutting guide to make a femoral bone cut consistent with a pre-operative surgical plan In a more detailed embodiment of the seventh aspect, the method further includes repositioning the cutting guide using navigation guidance displayed on the visual display, the cutting guide including the first inertial measurement unit (IMU), the cutting guide operatively coupled to a tibial patient-specific anatomical mapper (PAM) that includes a surface precisely and correctly mating with a tibial surface in only a single location and orientation, where the navigation guidance includes at least one of the virtual model of the cutting guide and a virtual model of a patient tibia, as well as an indication regarding the three dimensional position of the cutting guide with respect to the patient tibia using data from the first IM U, where the navigation guidance also includes guidance for repositioning the cutting guide to make a tibial bone cut consistent with the pre-operative surgical plan. In yet another more detailed embodiment, the method further includes mounting the femoral PAM surface to the patient femoral surface in the correct single location and orientation, coupling a second inertial measurement unit (IMU) to the patient femur, and registering the first and second IMUs with respect to one another. In a further detailed embodiment, the method further includes mounting the tibial PAM surface to the patient tibial surface in the correct single location and orientation, coupling a second inertial measurement unit (IMU) to the patient tibia, and registering the first and second IMUs with respect to one another. In still a further detailed embodiment, the navigation guidance includes only the virtual model of the cutting guide. In a more detailed embodiment, the navigation guidance includes only the virtual model of the patient femur. In a more detailed embodiment, the navigation guidance includes at least one of the virtual model of the patient femur and the virtual model of the patient tibia, in addition to a first cutting line representing the real-world position of the cutting guide and a second cutting line representing an intended pre-operative plan position of the cutting guide for making at least one of the femoral bone cut and the tibial bone cut.

In a further detailed embodiment, the method further includes making the femoral bone cut using a surgical saw guided by the cutting guide, and repositioning the cutting guide using navigation guidance displayed on the visual display, the cutting guide including the first inertial measurement unit (IMU) and being operatively coupled to the femoral patient-specific anatomical mapper (PAM), where the navigation guidance includes at least one of the virtual model of the cutting guide and the virtual model of the patient femur, as well as an indication regarding the three dimensional position of the cutting guide with respect to the patient femur using data from the first IMU, where the navigation guidance also includes guidance for repositioning the cutting guide to make a subsequent femoral bone cut consistent with the pre-operative surgical plan. In still a further detailed embodiment, the method further includes making the femoral bone cut using a surgical saw guided by the cutting guide, where the femoral bone cut is a distal resection, and repositioning the cutting guide using navigation guidance displayed on the visual display, the cutting guide including the first inertial measurement unit (IMU) and being operatively coupled to the femoral patient-specific anatomical mapper (PAM), where the navigation guidance includes at least one of the virtual model of the cutting guide and the virtual model of the patient femur, as well as an indication regarding the three dimensional position of the cutting guide with respect to the patient femur using data from the first IMU, where the navigation guidance also includes guidance for repositioning the cutting guide to drill holes into the resected femur consistent with the pre-operative surgical plan. In a more detailed embodiment, the method further includes drilling holes into the resected femur femoral bone using a surgical drill guided by the cutting guide, inserting surgical pins into the drill holes, repositioning a 4-in-1 cutting guide against the resected femur using the inserted surgical pins for alignment, and making at least one femoral resection cut using guidance from the 4-in-1 cutting guide. In a more detailed embodiment, the method further includes drilling holes into the resected femur femoral bone using a surgical drill guided by the cutting guide, inserting surgical pins into the drill holes, repositioning a fixed position cutting guide against the resected femur using the inserted surgical pins for alignment, and making at least one femoral resection cut using guidance from the fixed position cutting guide.

BRIEF DESCRIPTION OF THE DRAWINGS

FIG. 31 is a profile view of a distal end of a femur post making five resection cuts in accordance with a TKA pre-operative plan.

FIG. 32 is an elevated perspective view of a distal end of the femur showing components in accordance with the instant disclosure dismounted therefrom.

FIG. 33 is an elevated perspective view of a distal end of the femur showing components in accordance with the instant disclosure mounted thereto, including a guide foot that replaces the PAM.

DETAILED DESCRIPTION OF EXEMPLARY EMBODIMENTS

The exemplary embodiments of the present disclosure are described and illustrated below to encompass exemplary devices, methods, and techniques related to computer aided surgery and computer planned surgery. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
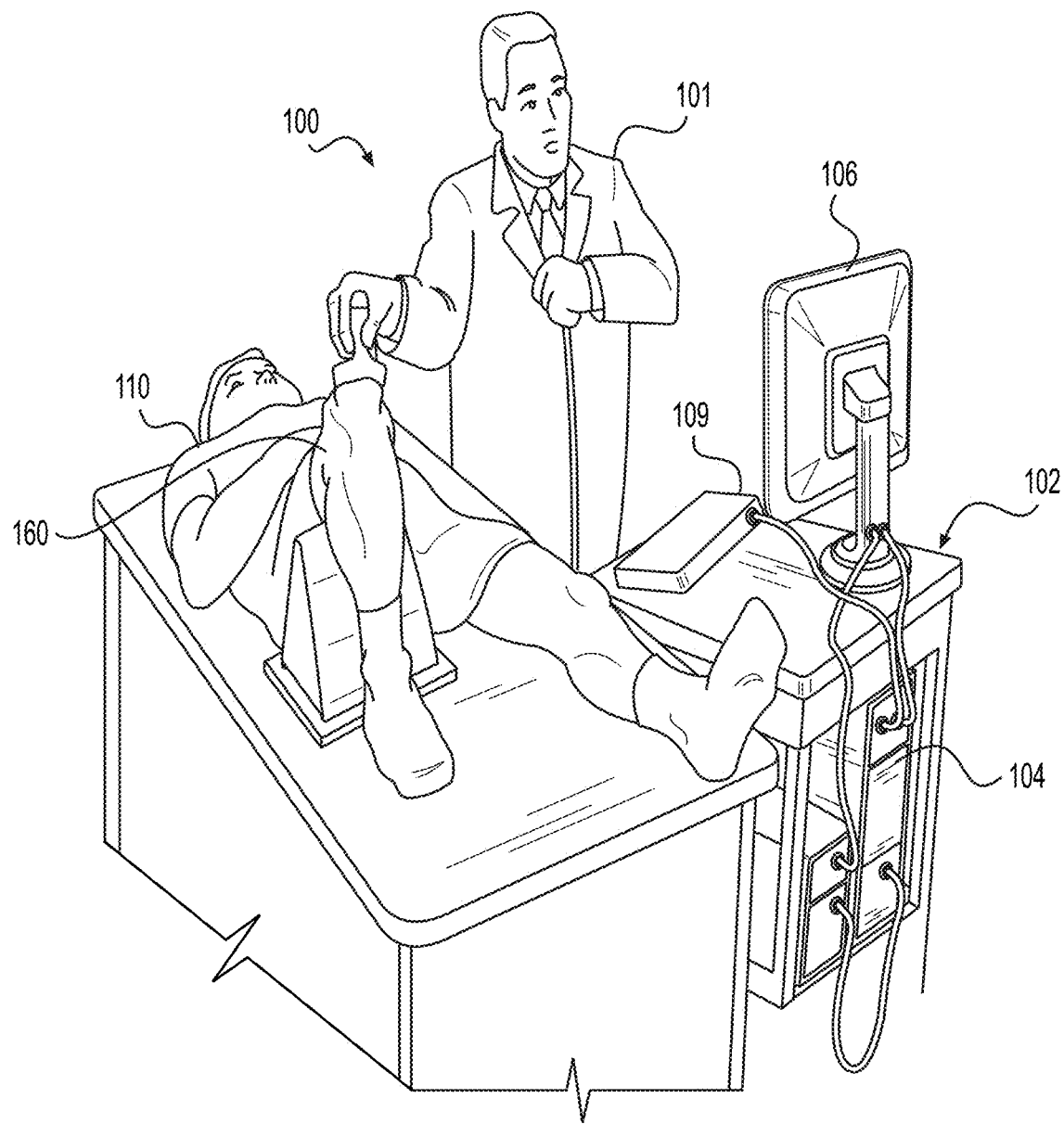
FIG. 1 is a diagram depicting portions of an exemplary image guided surgical system in accordance with the instant disclosure.
Figure 2:
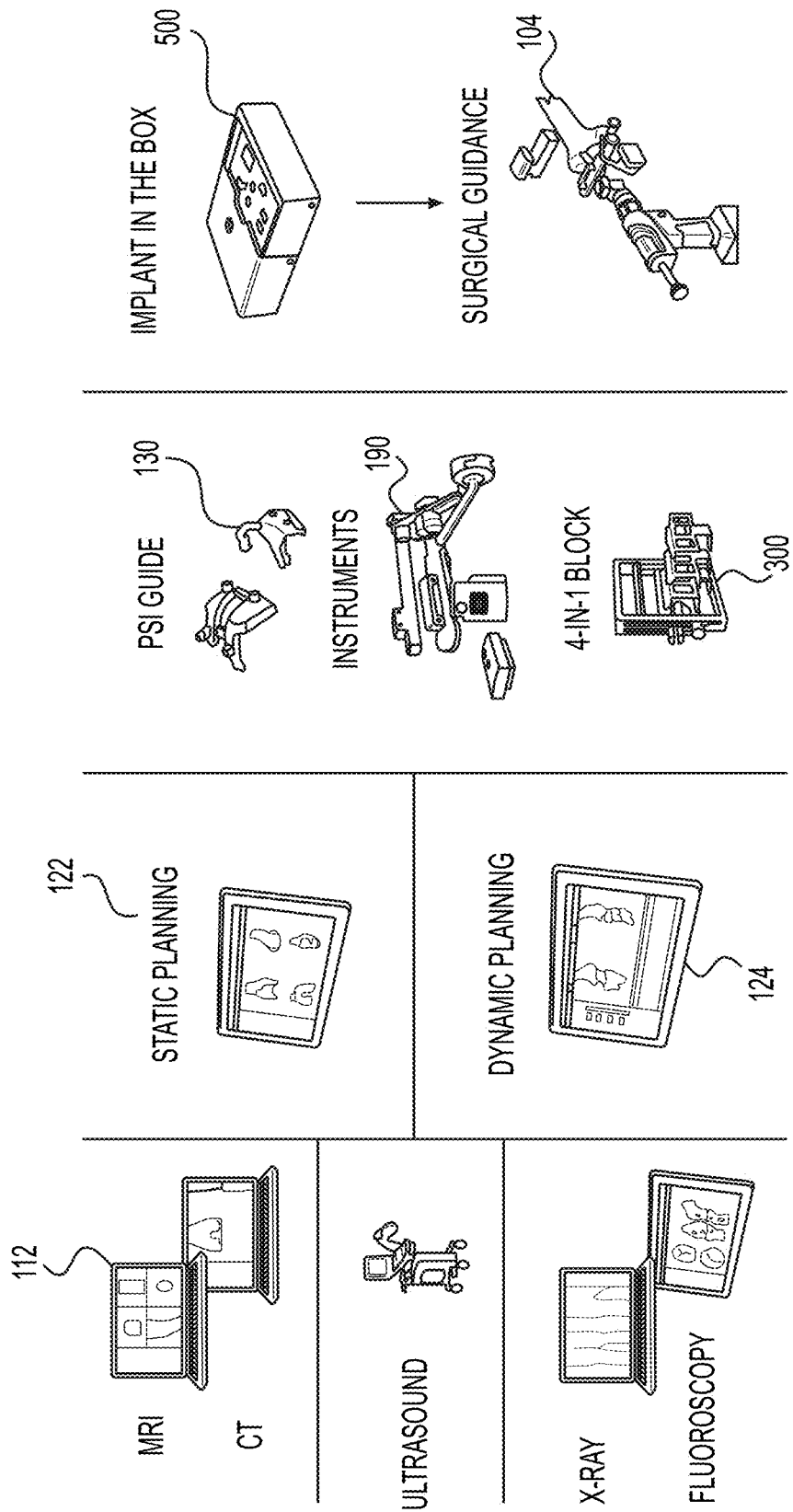
FIG. 2 is a diagram depicting an overview of an exemplary sequence in accordance with the instant disclosure where pre-operative images are eventually converted into surgical kits and surgical guidance instructions.
Figure 3:
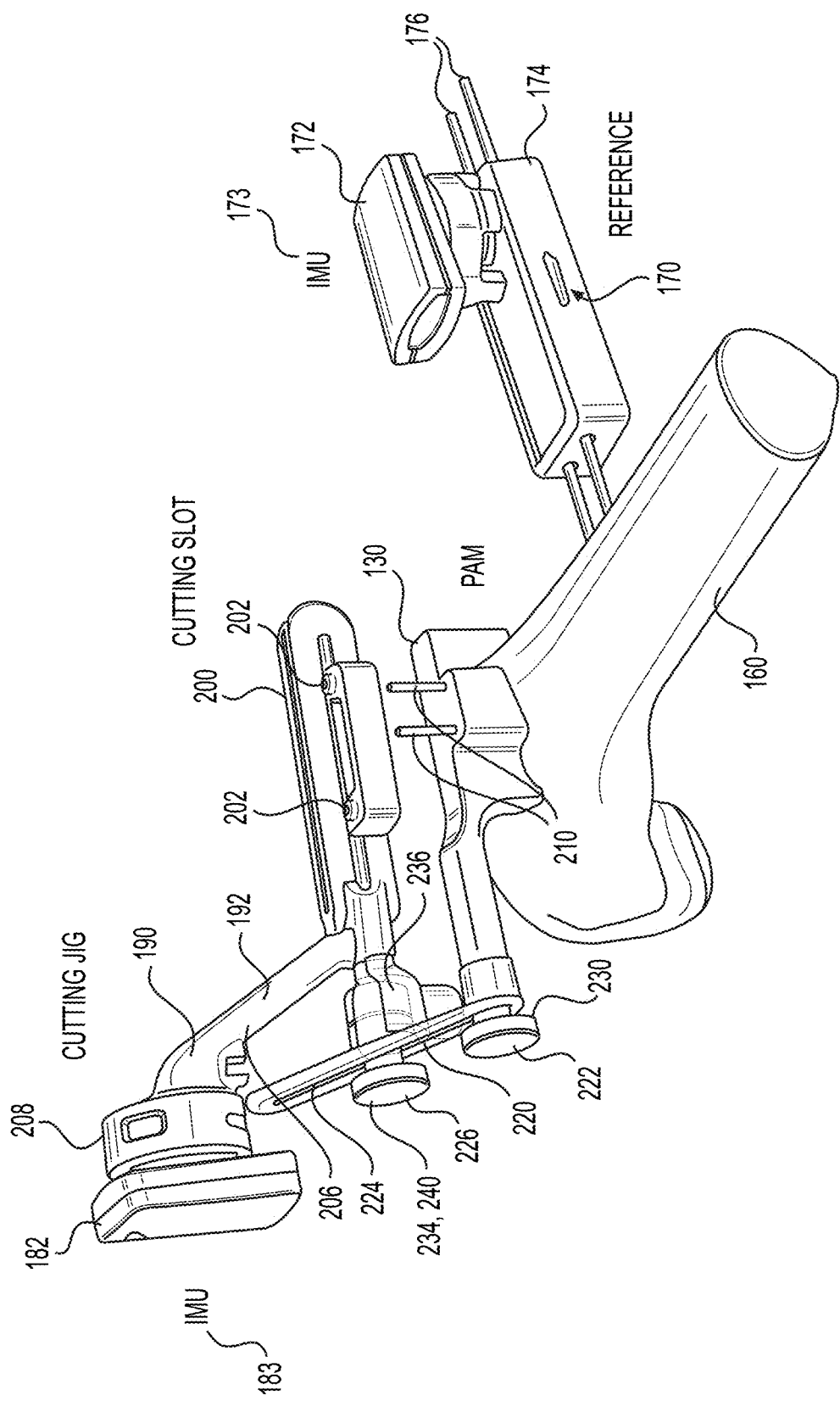
FIG. 3 is an elevated perspective view of a distal femur showing exemplary components of the image guided surgical system mounted thereto.

Referencing FIGS. 1-3, an image guided surgical system 100 in accordance with the instant disclosure for use by a surgeon 101 or other personnel may comprise a workstation 102 that includes a computer/controller and associated software 104 communicatively coupled to one or more visual displays 106 and input devices 109 (e.g., keyboard, mouse, etc.) and surgical instruments 170, 190 to facilitate surgical navigation related to an orthopedic replacement or revision surgery. In exemplary form, the instant surgery will involve a total knee arthroplasty replacement or revision procedure. Nevertheless, those skilled in the art will understand that the exemplary techniques, systems, software, and components may be used as part of any orthopedic replacement or revision surgical procedure and by no means are limited to the knee.

In this exemplary embodiment, the associated software 104 includes surgical navigation software making use of tissue models (that may include bone and soft tissue models) 114 that may be specific to the patient 110. By way of example, imaging of the patient 110 may be undertaken during or in advance of surgery using any of the known imaging modalities 112 sufficient for producing one or more patient-specific virtual tissue models 114 including, but not limited to, X-ray, fluoroscopy, ultrasound, CT, MRI. From the data output using at least one of the imaging modalities 112, one or more patient-specific virtual tissue models 114 may be created using any of various methods known to those skilled in the art of bone reconstruction. For example, for knee surgeries, exemplary patient-specific virtual tissue models may include, but are not limited to, bones of femur, tibia, and patella, cartilage associated with one or more of these bones, and connective ligament tissue. As part of the virtual tissue models 114, the software 104 may be uploaded with data reflecting the relative positions of the bones with respect to one another so that static poses of the models are available over a range of motion and, in addition or in the alternative, dynamic images of the models are available to show virtual motion of the models with respect to one another across a range of motion. These dynamic images may be extracted directly from certain modalities, such as, without limitation, fluoroscopy, or may be extrapolated using computer simulation software making use of a plethora of static poses across a range of motion.

The exemplary software 104 may make use of the virtual tissue models 114 to create or incorporate a pre-operative surgical plan to achieve the knee replacement or revision. As part of an exemplary surgical plan, virtual models 120 of one or more orthopedic implants may be loaded or created and then test fit onto the virtual tissue models 114 in order to identify the sizing of the implant(s), the bone cuts (resection cuts) needing to be made, and the proper placement of the eventual orthopedic implant(s). By way of example, the exemplary software 104 incorporates a static planner 122 that allows fitting of a virtual model of an orthopedic implant 120 onto at least one of the patient's virtual bone models 114 in order to assess fit, sizing, identification of anatomical landmarks, and bone cut positions for receiving the eventual implant. As part of this static planner 122, once a virtual implant is chosen and its position is finalized with respect to the virtual tissue models 114, the planner may calculate the position of the bone cuts (for the actual patient bone) needed to effectuate implantation of the orthopedic implant. This static planner 122 is contrasted with an available dynamic planner 124 as part of the software 102, which allows concurrent repositioning of the virtual tissue models 114 and the orthopedic implant models 120 as a unified unit so that one may assess kinematic factors for determining implant type, shape, size, and position on the resected patient bone. Those skilled in the art are familiar with kinematic considerations surgeons utilize to differentiate between orthopedic implants and the factors a surgeon uses to choose an orthopedic implant using kinematic data. As part of this dynamic planner 124, once a virtual implant is chosen and its position is finalized with respect to the virtual tissue models 114, the planner may calculate the position of the bone cuts (for the actual patient bone) needed to effectuate implantation of the orthopedic implant.

After the pre-operative surgical plan is created or uploaded, one may use the preoperative plan to create custom instrumentation for the femur, tibia, and/or patella, that includes, without limitation, patient anatomical mappers (PAMs) 130 and cutting guides 190.

A PAM 130 comprises a patient-specific device that matches the patient anatomy in only a single known position and orientation and may be mounted to the patient using surgical pins 210. By way of example, the PAM 130 may have one surface with a negative geometry precisely mating with the patient anatomy (in other words, the surface shape of the PAM precisely follows the surface, including shape changes, of the patient anatomy, so that a patient trough would reflect a PAM crest, while a patient crest would reflect a PAM trough). By utilizing a PAM that fits to the patient anatomy in only a single location and orientation, instrumentation or other parts having known geometries (size, width, length, height, etc.) may be attached to the PAM to facilitate localization of position and orientation of the instrumentation or other parts within a frame of reference utilized by the surgical navigation software. In other words, because one knows the exact position and orientation of the PAM with respect to a patient anatomy (e.g., a bone), any structure (having known dimensions) rigidly mounted to the PAM will also have a known position and orientation with respect to the patient anatomy. And a PAM may be utilized in combination with a cutting guide 190.

In accordance with the instant disclosure, exemplary cutting guides 190 may be aligned and positioned with the aid of the PAM 130. By way of introduction, an exemplary cutting guide 190 may be repositionably mounted to the PAM 130 so that the PAM is used for its reference position to know the position and orientation of the cutting guide with respect to a patient's bone. Conversely, or in addition, the cutting guide 190 may be disengaged from the PAM 130. In such an instance, the PAM 130 may be coupled to a pinner having orifices configured to receive an alignment pin in only a single orientation. Using the pinner, once correctly positioned, two or more pins are inserted into a patient's bone so that the pins align with orifices of an exemplary cutting guide (disjoined from the PAM 130). In this manner, an exemplary cutting guide may be aligned by sliding over the pins in order to align the cutting guide to make one or more bone cuts.

The pre-operative surgical plan may also be used to create computer instructions, referred to herein as a patient case file or surgical plan, that may be loaded into an associated surgical navigation software application 104 to facilitate real-time guidance of the relevant surgical instrumentation. In addition, the instrumentation and instruments needed for surgery, which may be created or chosen using the static 122 and/or dynamic planner 124, may be manufactured, packaged, sterilized, and assembled into a kit 500 for delivery in a just-in-time manner.

Referring to FIG. 3, a distal femur 160 of the patient 110 may include a rigid reference 170 attached to a patient bone, either via an existing surgical incision or percutaneously. In exemplary form, the rigid reference 170 comprises a component of the image guided surgical system 100 and may include a housing 174 mounted to a pair of pins 176 fastened to the femur 160. The rigid reference 170 facilitates tracking of a patient bone 160 by the housing 174 coupling with or including an inertial measurement unit device 172 or other tracking device that communicates (whether wired or wirelessly) with the surgical navigation workstation 102. In exemplary form, an inertial measurement unit (IMUs) device 172 may include an inertial measurement unit (IMU) 173, a battery, and a wireless transmitter contained within a single housing, where the device 172 may be operative to create and transmit data to the surgical navigation software application 104. Each IMU 173, 183 may consist of at least one triaxial accelerometer, one triaxial magnetometer, and one triaxial gyroscope. In this manner, the IMU 173, 183 generates data indicative of acceleration in three orthogonal axes, magnetic data, and gyroscopic data, which the surgical navigation software application 104 uses to determine changes in position and orientation of the IMU. Accordingly, by having the INU 173 rigidly mounted to the bone (e.g., femur 160) using the rigid reference 170, changes in position and orientation of the IMU can be quickly and accurately attributed to changes in position and orientation for the bone. Thus, by knowing how the IMU 173 is being repositioned as a function of time, the surgical navigation software application 104 is also able to determine changes in position and orientation of the bone over the same time period. As will be discussed hereafter, by initializing the IMU device 172 of the rigid reference 170 with respect to a second IMU device 182 associated with a cutting guide 190, a relative position of the cutting guide with respect to the patient bone can be determined by the surgical navigation software application 104.

Turning back to FIG. 3, an exemplary cutting guide 190 in accordance with the instant disclosure is configured to be repositionably mounted to a PAM 130 in order to guide a surgeon in making one or more bone cuts. This exemplary cutting guide 190 may be used for each of the femoral and tibial resections as part of a total knee arthroplasty.

In this exemplary embodiment, the cutting guide 190 includes a guide body 192 having at least one cutting slot 200 for guiding a surgical sagittal saw or similar tool 250 (see FIG. 25) along a planar path to make one or more bone cuts. The guide body 192 may also, separate from or in addition to the slot 200, delineate one or more though orifices 202 sized to allow throughput of a surgical pin 210. By way of example, each surgical pin 210 may be mounted to the patient's bone and be utilized to guide and couple to a fixed position cutting block 300 (see FIG. 30). In this exemplary embodiment, the guide body 192 includes a neck 206 terminating at a receiver 208 configured to have mounted thereto the second inertial measurement device 182.

By way of example, the second inertial measurement device 182 may include an inertial measurement unit (IMU) 183, a battery, and a wireless transmitter contained within a single housing, where the device 182 may be operative to create and transmit data to the surgical navigation software application 104.

As disclosed herein, each IMU 173, 183 may comprise three gyroscopes, three accelerometers, and three Hall-effect magnetometers (set of three, tri-axial gyroscopes, accelerometers, magnetometers) that may be integrated into a single circuit board or comprised of separate boards of one or more sensors (e.g., gyroscope, accelerometer, magnetometer) in order to output data concerning three directions perpendicular to one another (e.g., X, Y, Z directions). In this manner, each IMU 173, 183 may be operative to generate 21 voltage or numerical outputs from the three gyroscopes, three accelerometers, and three magnetometers. In exemplary form, each IMU 173, 183 may include a sensor board and a processing board, with a sensor board including an integrated sensing module consisting of three accelerometers, three gyroscopic sensors and three magnetometers (LSM9DS, ST-Microelectronics) and two integrated sensing modules consisting of three accelerometers, and three magnetometers (LSM303, ST-Microelectronics). In particular, the IMU 173, 183 may also include angular momentum sensors measuring rotational changes in space for at least three axes: pitch (up and down), yaw (left and right) and roll (clockwise or counter-clockwise rotation). In this manner, the IMUs 173, 183 generates data indicative of acceleration in three orthogonal axes, magnetic data, and gyroscopic data, which the surgical navigation software application 104 uses to determine changes in position and orientation of each IMU.

By having the IMU 183 rigidly mounted to the cutting guide 190, changes in position and orientation of each IMU 173, 183 can be quickly and accurately attributed to changes in position and orientation of the cutting guide with respect to the patient bone. Thus, by knowing how the IMU 183 is being repositioned as a function of time, the surgical navigation software application 104 is also able to determine changes in position and orientation of the cutting guide 190 over the same time period. As will be discussed hereafter, by initializing the IMU 173 of the rigid reference 170 with respect to the second IMU 183 associated with the cutting guide 190, a relative position of the cutting guide with respect to the patient bone can be determined by the surgical navigation software application 104.

By way of example, the cutting guide 190 may have any number of known positions, such that when the cutting slot 200 is placed into one of these known positions, the position of the cutting slot 200 is known relative to the PAM 130. In order to repositionably mount the cutting guide 190 to the PAM 130, a mechanical connection 220 exists therebetween that may include one or more joints. In exemplary form, the mechanical connection 220 includes a lower joint 222, an adjuster 224, and an upper joint 226.

By way of example, the lower joint 222 may be at or near the connection of the PAM 130 to the cutting slot 200. The lower joint 222 may comprise a revolute joint including a bolt or screw 230 (optionally spring loaded) that may be tightened to selectively inhibit rotation of the adjuster 224 with respect to the PAM 130 and, accordingly, in a coarse sense adjust the position of the cutting slot 200. Alternatively, the lower joint 222 may be any joint or motion activated device (motor driven) that allows selective repositioning of the adjuster 224 with respect to the PAM 130 so that, when desired, repositioning of the adjuster with respect to the PAM is substantially inhibited.

By way of example, the adjuster 224 may comprise an oblong or extended ring at least a portion of the lower joint 222 engages to fix and release the position of the adjuster with respect to the lower joint. Similarly, the adjuster 224 is also mounted to the upper joint 226 which, in exemplary form, may comprise a revolute joint 234.

In exemplary form, the revolute joint 234 may include a bolt or screw 240 (optionally spring loaded) that may be tightened to selectively inhibit rotation of the adjuster 224 with respect to the cutting guide 190. Alternatively, the upper joint 226 may be any joint or motion activated device (motor driven) that allows selective repositioning of the adjuster 224 with respect to the cutting guide 190 so that, when desired, repositioning of the adjuster with respect to the cutting guide is substantially inhibited. In addition to the revolute joint 234, the upper joint 226 may also include a spherical joint 236. In this fashion, when the spherical joint is not locked, the cutting guide 190 may be angularly repositioned with respect to the adjuster 224 (and PAM 130) up to 45 degrees with respect to an axis extending parallel to the rotational axis of the revolute joint 234. As will be discussed in more detail hereafter, the adjustability of the spherical joint 236 may be utilized to adjust the varus or valgus nature of a distal femoral bone cut.

Figure 4:
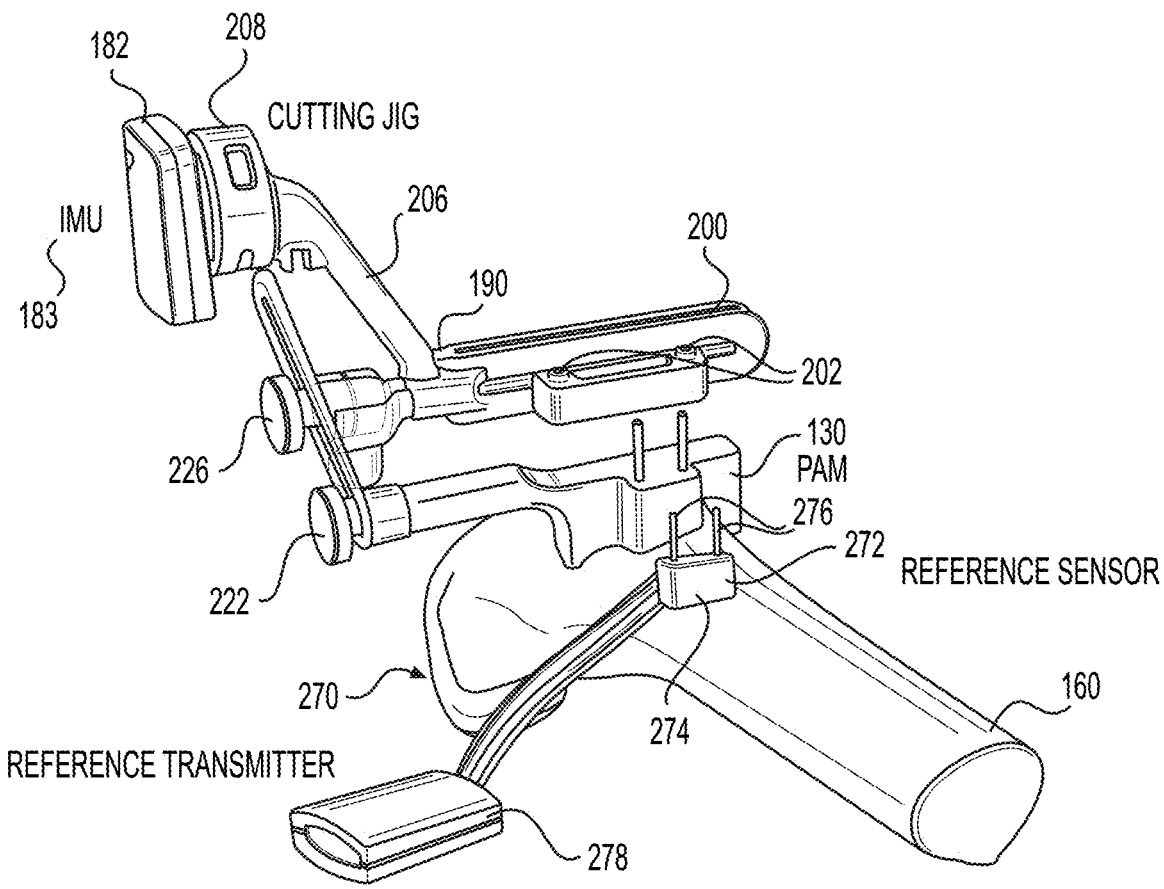
FIG. 4 is an elevated perspective view of a distal femur showing exemplary and alternate exemplary components of the image guided surgical system mounted thereto.

Turning to FIG. 4, an alternate exemplary rigid reference 270, that may be used in lieu of or in addition to the rigid reference 170 of FIG. 3, comprises a reference housing 272, that includes an inertial measurement unit, mounted to a pair of pins 276 fastened to the femur 160. This alternate exemplary rigid reference 270 facilitates tracking of a patient bone 160 by communicatively coupling (whether wired 273 or wirelessly) the reference housing 272 (with the IMU 274) with a reference transmitter located within a housing 278 that also houses a power supply (e.g., battery). In exemplary form, the relatively small size of the reference housing 272 allows it to be mounted to the patient bone 160 without requiring an additional incision or larger incision to access the surgical site of the joint replacement or revision. In other words, this alternate exemplary rigid reference 270 provides a size advantage (smaller) over the other rigid reference 170 by not requiring the transmitter and power supply be rigidly mounted to the patient bone. For example, the IMU is operative to create and convey data to the transmitter, which passes the data onto the surgical navigation software application 104. The IMU 274 may consist of at least one triaxial accelerometer, one triaxial magnetometer, and one triaxial gyroscope. In this manner, the IMU 274 generates data indicative of acceleration in three orthogonal axes, magnetic data, and gyroscopic data, which the surgical navigation software application 104 uses to determine changes in position and orientation of the IMU. Accordingly, by having the IMU 274 rigidly mounted to the bone (e.g., femur 160) using the rigid reference 270, changes in position and orientation of the IMU can be quickly and accurately attributed to changes in position and orientation for the bone.

Thus, by knowing how the IMU 274 is being repositioned as a function of time, the surgical navigation software application 104 is also able to determine changes in position and orientation of the bone over the same time period. As will be discussed hereafter, by initializing the IMU device 274 of the rigid reference 270 with respect to the second IMU device 182 associated with the cutting guide 190, a relative position of the cutting guide with respect to the patient bone can be determined by the surgical navigation software application 104.

Referencing FIG. 1 again, the workstation 102 running the surgical navigation software 104 is operative to process sensor data from the IMUs 173/274, 183 and convert this sensor data to information relating to a resection plane location relative to the patient anatomy. In addition, the surgical navigation software 104 is operative to provide visualization to a surgeon via the one or more visual displays 106. In exemplary form, visualization may include 3D virtual tissue models 114, 3D virtual models of the cutting guide 190 or cutting slot 200, projections, text, or any other forms of communicating the orientation and position of the cutting slot relative to the patient anatomy. The information communicated as part of the visualization may be updated at a minimum of ten frames per second so that the information being displayed may be considered near real-time or real-time.

Any or all of the components of the cutting guide 190 may be disposable for single-use. Alternatively, any or all of the components of the cutting guide 190 may be reusable and amenable to resterilization. In any event, any or all of the components of the cutting guide 190, PAM 130, and rigid references 170, 270 may be fabricated from numerous materials such as, without limitation, polymers, metals, and composites, and may be fabricated using techniques including, but not limited to, additive manufacturing, injection molding, machine milling, and casting. Assembly and connection of individual components of cutting guide 190, PAM 130, and rigid references 170, 270 may be performed by any means available, such as appropriate press fitting, locking, utilization of external fixation devices such as set screws, adhesives, welding, or other methods known to those skilled in mechanical assemblies to secure components to one another. While various components of the cutting guide 190, PAM 130, and rigid references 170, 270 may have been discussed separately herein, it is understood that any or all the components may be integrated or separable.

Figure 5:
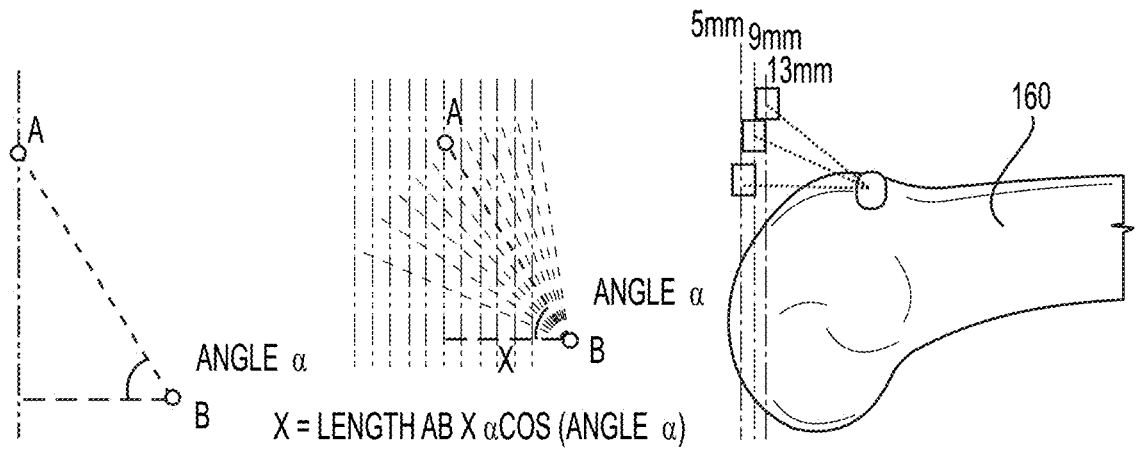
FIG. 5 is a series of illustrations correlating trigonometry with the possible locations of a distal femoral resection plane.

Referring to FIG. 5, to provide real-time feedback as to the position and orientation of the cutting slot 200, IMUs 173/274, 183 are operative to generate data indicative of orientation and position, which is communicated to the surgical navigation software 104 running on the workstation 102. The following is a discussion of how orientation and position of the cutting slot 200 are determined by the surgical navigation software 104 when teamed with known dimensions for the surgical equipment (e.g., cutting guide 190, PAM 130) in an exemplary procedure for a total knee arthroplasty (TKA).

IMUs 173/274, 183 in accordance with the instant disclosure may measure orientation about an x-axis, y-axis, and z-axis, but may not directly measure translation. In order to determine translation of the IMUs, one may use external sensors or have the IMUs initialized using a starting position and orientation that is known with respect to a real-world object (e.g., a bone). For example, the external sensors may comprise linear positioning sensors (e.g. linear variable displacement transformer, linear motion encoder, ultrasonic ranging, or optical ranging) to provide translation information.

In exemplary form, as discussed hereafter, the instant disclosure may make use of an initialization position where the IMUs 173/274, 183 are rigidly mounted to the cutting guide 190 and PAM 130, respectively, so that the relative position and orientation of the cutting guide with respect to the PAM is known (and the relative position and orientation of the IMUs 173/274, 183 is also known). By way of further example, this initialization position may have cutting slot 200 aligned along the same plane as the PAM. After establishing this initialization position, the cutting guide 190 may be repositioned with respect to the PAM. 130 to carry out the femoral bone cuts established via the pre-operative surgical plan.

In the context of the instant disclosure, pre-operative surgical planning will establish the depth (e.g., location) of the distal bone cut for a TKA, as well as the placement of the PAM 130 on the patient bone 160. As depicted in FIG. 5, with the depth of the distal bone cut known, identified as "x", and the starting position B known from the placement of the PAM 130 with respect to the bone 160, two pieces of information are required in order to position the cutting guide 190 correctly to effectuate the distal cut: (1) the angle $\alpha$; and (2) the distance AB. The distance AB is a function of known instrument dimensions (this is the linear distance from the center of the PAM to the center of the cutting slot 200), where the distance AB is constant in accordance with the instant disclosure and does not change as the cutting guide 190 is rotated about the PAM 130 via the lower joint 222. As a result, using trigonometry, one can calculate the angle $\alpha$ from the equation of FIG. 5. And knowing this angle $\alpha$, the surgical navigation software 104 tracks the angular change of the cutting slot 200, via the IMU 173, 274, relative to the patient bone using the IMU 183 of the PAM 130, so that when cutting slot is positioned at angle $\alpha$, the surgical navigation software informs the surgeon the cutting slot is positioned in accordance with the pre-operative surgical plan, so that the surgeon may carry out the distal femoral bone cut. In case the cutting slot 200 is not aligned with angle $\alpha$, the surgical navigation software provides feedback to the surgeon indicating how the cutting slot should be repositioned to achieve angle $\alpha$. As will be discussed hereafter, the joints 226, 236 associated with the cutting guide 190 may be repositioned to adjust for varus/valgus, flexion/extension, and other known degrees of freedom.

In accordance with the instant disclosure, knowing the instrument (PAM 130, cutting guide 190) dimensions is important for calculating the relative position and orientation of the instruments dynamically during a surgical procedure, such as TKA. For example, each of the PAM 130, cutting guide 190, and cutting slot 200 may be appropriately sized to facilitate performing the desired surgery, preferably with minimal modification to the standard incision or minimally invasive incision. Appropriate dimensions for each component (e.g., the PAM 130, cutting guide 190, and cutting slot 200) may be selected prior to surgery in many ways. For example, each component may be made in a patient-specific manner, where all dimensions are selected to best match the patient and the surgical plan. Because patient-specific manufacturing may not be cost effective, another option is to choose dimensions based on population analysis. Those skilled in the art of orthopedic instrumentation will be familiar with sizing based on population analysis.

In general, a dimension of the anatomy is measured across several samples—a population—so that the range and variation of measurement is known across the samples. If desired, the population may be subdivided so that the range and variation of the measurement within each population subdivision is known. Methods of performing this subdivision include, but are not necessarily limited to, building regression models, unsupervised or supervised clustering, mixture modeling, partitioning, or any other methodology. In such a way, the best set of dimensions, or sizes, may be chosen for each component. This process may be performed in an automatic or semi-automatic way using statistical geometrical models or machine learning methods.

Using the known dimensions of component parts of each instrument, including post assembly, one can determine the allowable working volume of the surgical instrument—specifically the reachable cut orientation and positions—using methods familiar to those skilled in the art of robotic manipulators and forward kinematics. For example, the Denavit-Hartenberg (DH) parameters of each joint are known given the type of joint revolute, spherical, or any other—and the known dimensions of each linkage of the mechanical connection 220 as outlined above. From this information the DH convention may be used to establish the appropriate series of transformations between the first revolute joint 222 and the cutting slot 200. By calculating the end position and orientation at all or most of the allowable range of the variables for each joint, the working volume of the cutting slot 200 can be calculated for each of the steps in the surgical procedure. This convention may be used to verify that the chosen component dimensions are sufficient to achieve the desired surgical plan. FIGS. 6-15 show some possible critical dimensions of component parts of the system 100 as well as examples of population variations, which serve as inputs to dimensional choice.

Figure 6:
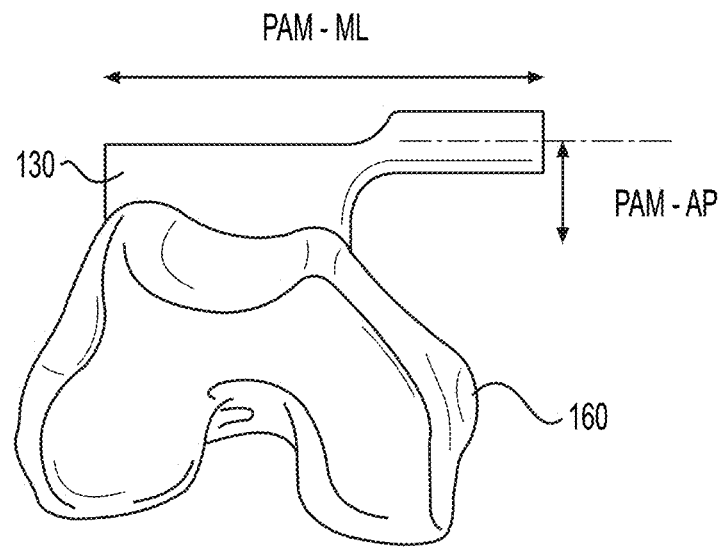
FIG. 6 is an end view of a distal femur showing an exemplary patient anatomical mapper mounted thereto, as well as identifying the dimension that is medial-lateral, as well as the dimension that is anterior-posterior.

Referencing FIG. 6, the PAM 130 may include critical dimensions, in addition to the patient specific features, comprising the (mediolateral) ML width and (anteroposterior) AP height. In this exemplary disclosure, the PAM 130 sets the center of rotation for the cutting guide 190, where the location of the PAM 130 can be selected to optimize the accuracy and performance of the system 100. The AP and ML dimensions should be carefully chosen so that the mechanical connection 220 coupling the PAM 130 to the cutting guide 190 clears both the intended incision and the medial aspect of the femora without causing impingement of the cutting guide with the bone or soft tissue once assembled. Similarly, the length of the cutting guide 190, as well as the location of the locking positions via the mechanical connection 220, should be selected to facilitate each of the procedural steps—allowing the cutting slot 200 to be properly positioned and manipulated without impingement.

Figure 7:
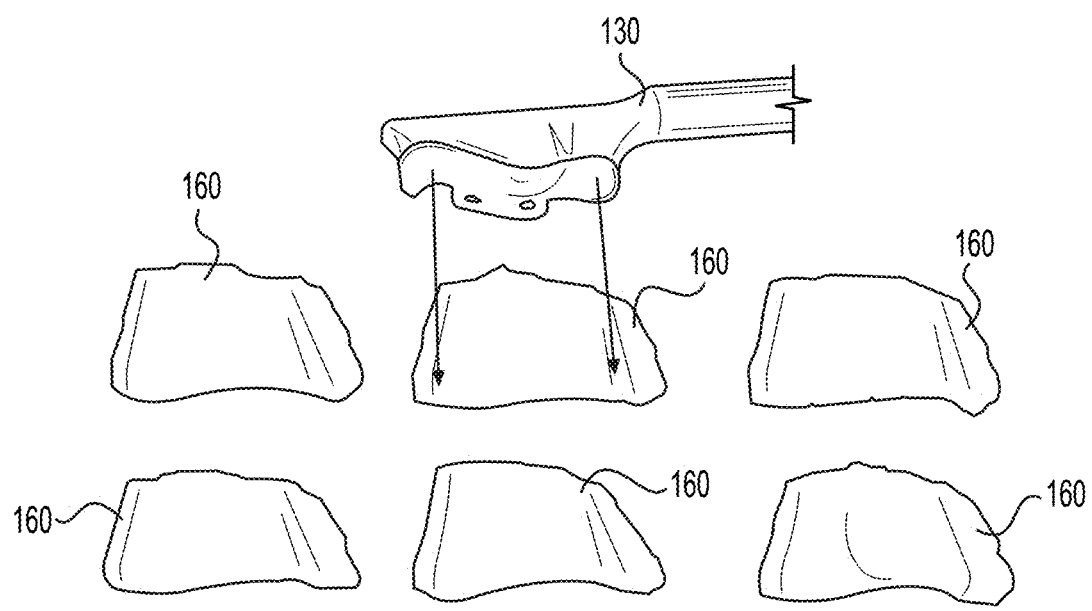
FIG. 7 is a graphical illustration of several different patient anatomical surfaces from a distal femur taken across a population within an anatomical statistical atlas and how using a generic model, the model can be deformed to be patient-specific when creating a patient anatomical mapper.

Referencing FIG. 7, an exemplary method for establishing and optimizing the mating site of the PAM 130 on the patient bone 160 includes utilization of a trained human expert as part of the pre-operative plan or, in addition to or in lieu of, using artificial intelligence (AI). AI learns the design constraints with regard to accuracy and the population morphology using measurements or surface geometry extracted from population statistics (i.e. statistical atlas), and outputs a location of the PAM 130 optimized for accuracy to achieve the desired plan.

Figure 8:
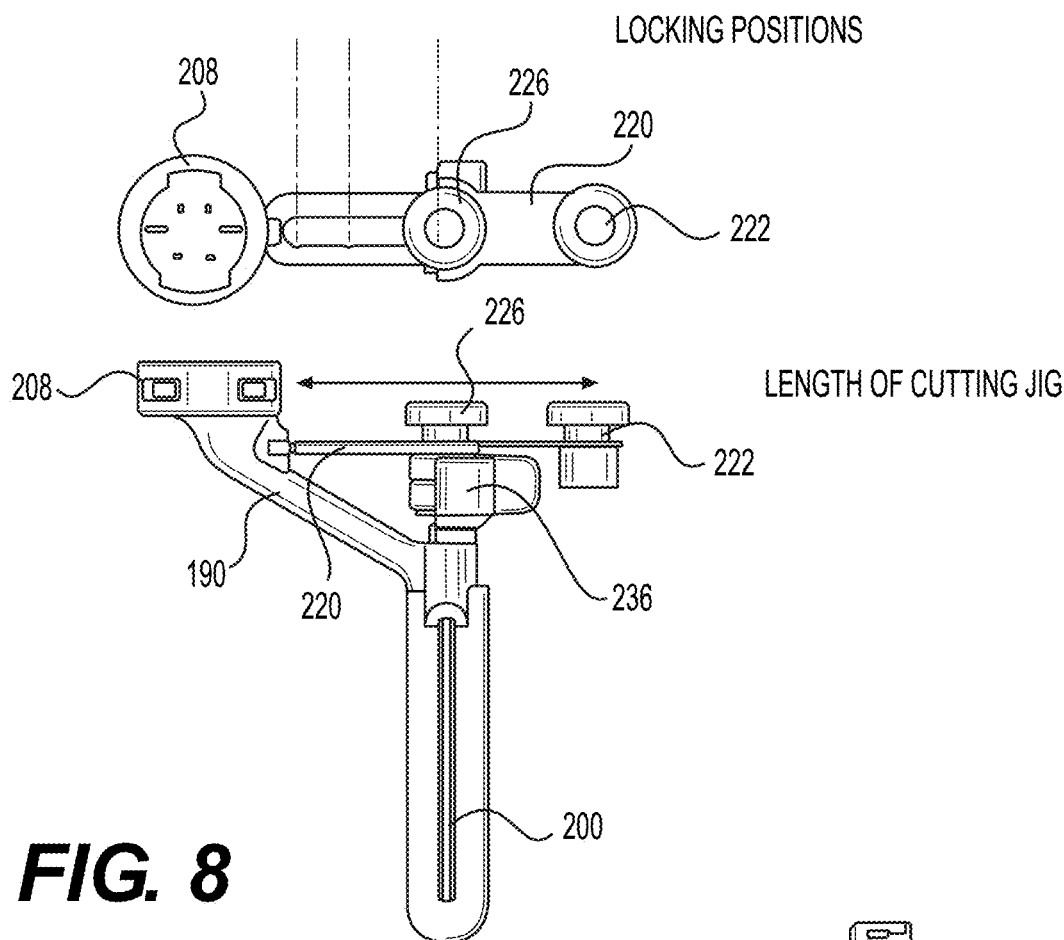
FIG. 8 are profile and overhead views of the same exemplary cutting guide and mechanical connection in accordance with the instant disclosure.
Figure 9:
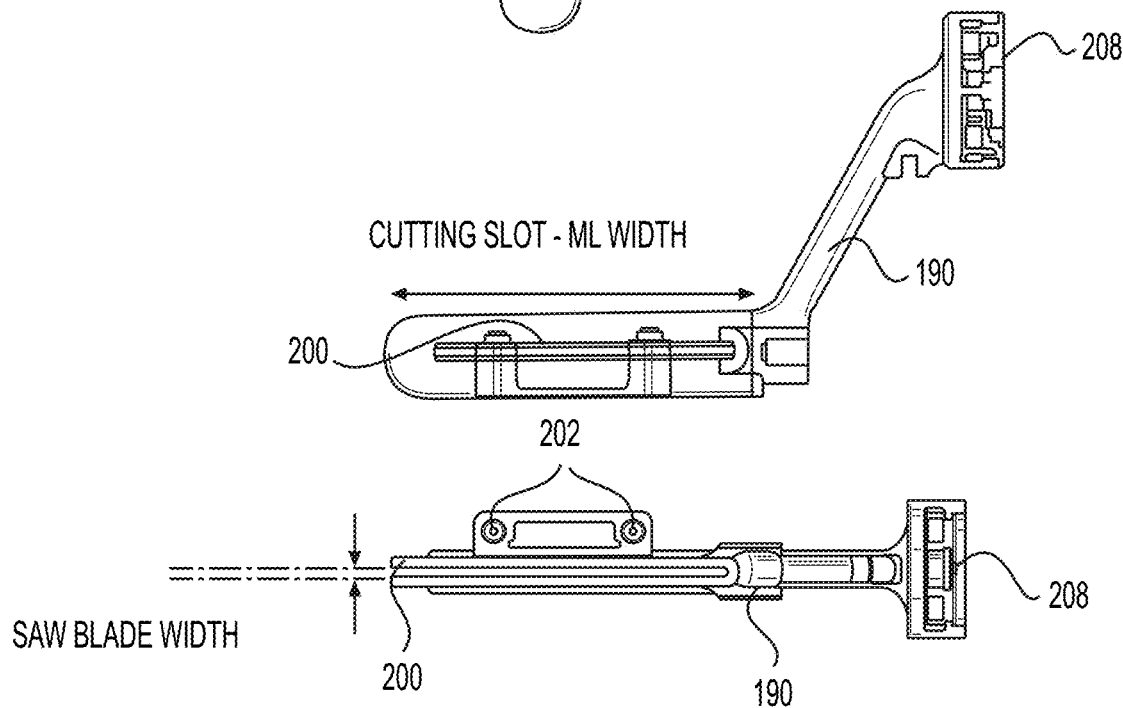
FIG. 9 are frontal and overhead views of the same alternate exemplary cutting guide and mechanical connection in accordance with the instant disclosure.

Turning to FIGS. 8 and 9, an exemplary cutting guide 190 in accordance with the instant disclosure may include a cutting slot 200 having dimensions that may be, configured in part, based upon the intended saw blade a surgeon anticipates using during the TKA, in order to appropriately capture the saw blade. In many TKA procedures, surgeons will utilize an oscillating tip saw to remove bone from the distal femur to prepare the femur to accept an orthopedic implant. Exemplary saw blades for an oscillating tip saw may have a thickness of approximately 1.19 millimeters, though other thickness may be used from time-to-time. In this manner, the width of the cutting slot 200 (in the AP direction) may be slightly greater than the thickness of the intended saw blade. The more precise the tolerance between the cutting slot 200 width and the saw blade results in greater precision that the bone cut of the blade is coplanar with the slot. In addition to establishing the AP width of the cutting slot 200, the ML length of the cutting slot should be chosen to allow resection of the entire distal, posterior and anterior surfaces as dictated by the pre-operative surgical plan.

Figure 10:
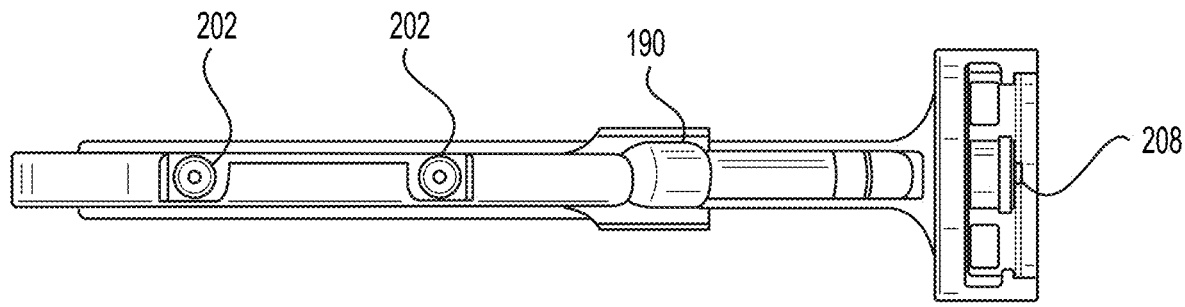
FIG. 10 is an overhead view of a further alternate exemplary cutting guide in accordance with the instant disclosure.

Referring to FIG. 10, an alternate exemplary cutting guide 290 includes a guide body 292 that replaces the cutting slot 200 with at least two guide pin holes 294. In this alternate exemplary cutting guide 290, the guide pin holes 294 match corresponding holes of a separate cutting block 300 (see FIG. 30) so that the guide 290 can be utilized to position two or more surgical pins 210 that are then utilized to align the cutting block. In other words, the cutting guide 290 is utilized by the surgeon to know where the drill holes and correspondingly fasten surgical pins 210 to the patient's bone. By way of further example, the pin holes drilled (or the position of the surgical pins themselves) into the patient's bone may be of the same distance from one another as the pin holes on a conventional distal cutting block 300. Post drilling of the pin holes, the guide 290 may be replaced with a separate cutting block, which is aligned to the patient's bone using the surgical pins. By way of example, exemplary conventional cutting blocks are available from Smith & Nephew, Zimmer, DePuy, and Stryker.

Figure 11:
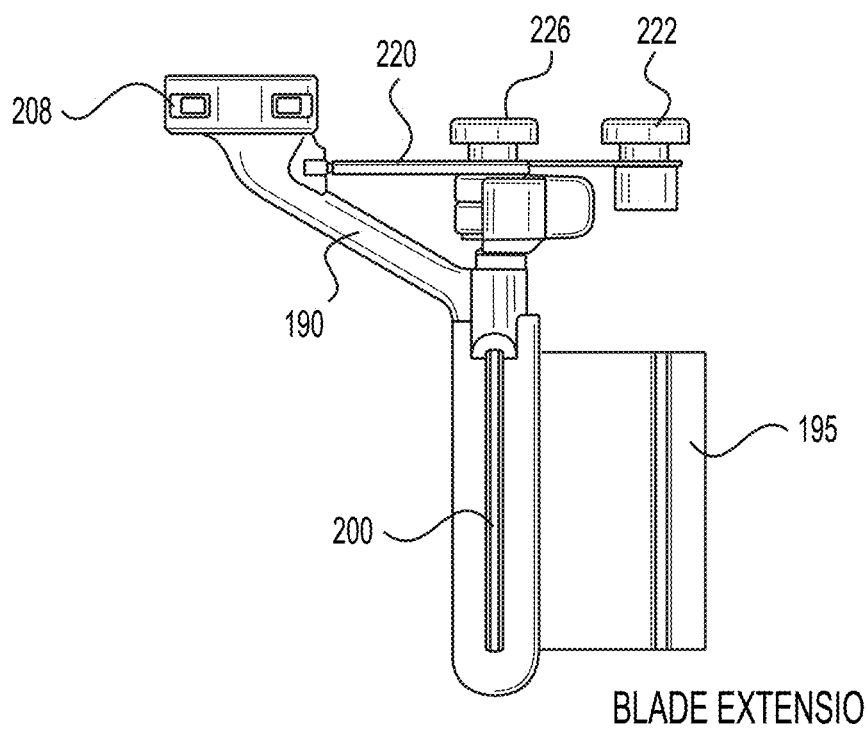
FIG. 11 is an overhead view of an exemplary pin guide and mechanical connection in accordance with the instant disclosure.

Looking at FIG. 11, the exemplary cutting guide 190 may include a blade support attachment 195 selectively coupled to the guide body 192 in order to provide stability to the surgical blade extending through the cutting slot 200.

Figure 12:
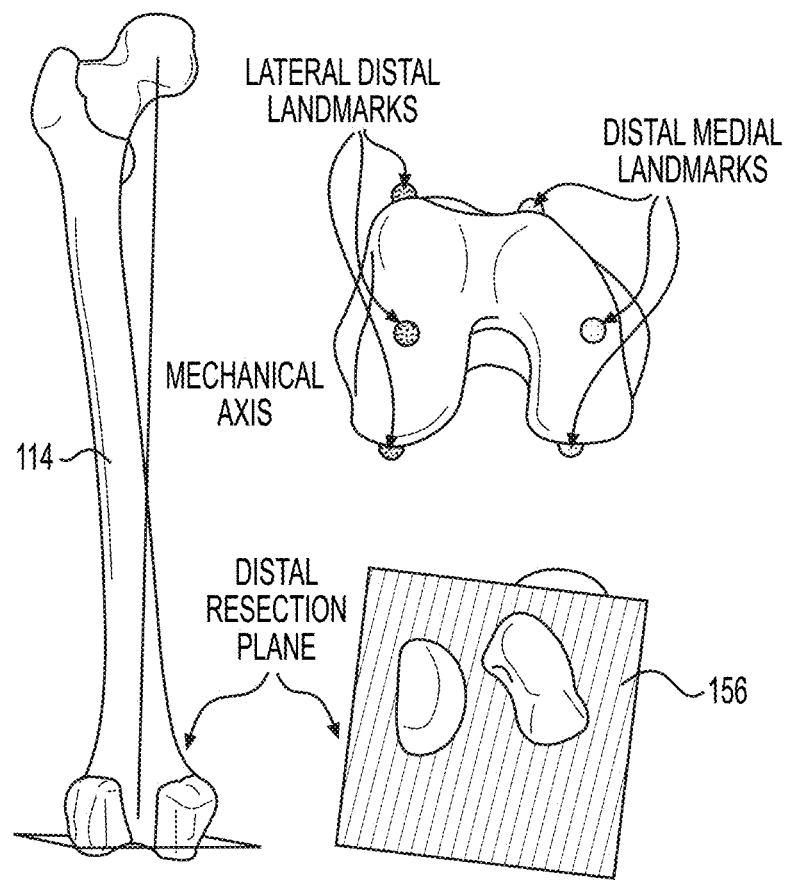
FIG. 12 is a compilation of graphics reflecting how automatic landmarks within a statistical atlas may be identified.
Figure 13:
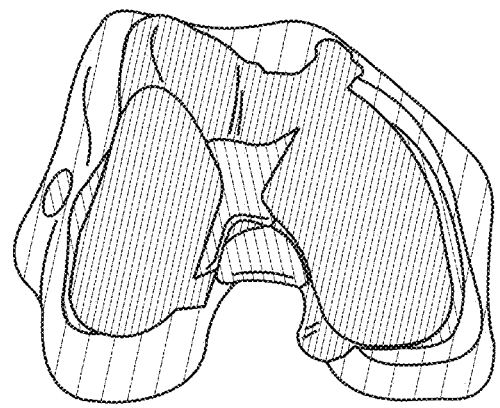
FIG. 13 is a distal end view of three superimposed femurs showing the differences in medio-lateral width of the distal resection for a total knee arthroplasty procedure.
Figure 14:
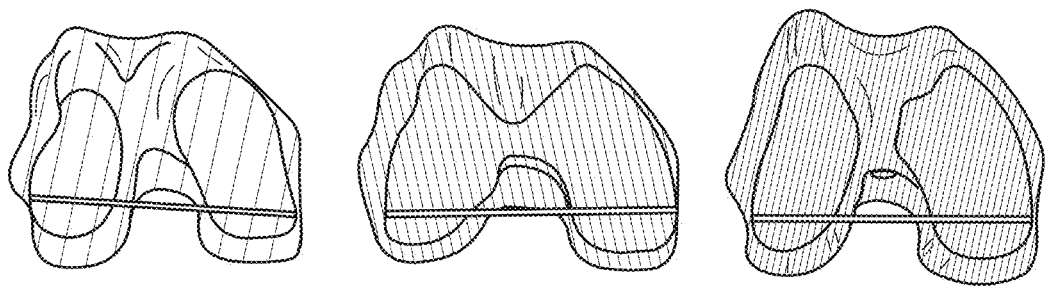
FIG. 14 comprises a series of distal end view of femurs from a statistical atlas showing how much bone is removed for a distal resection cut for different sized femurs.
Figure 15:
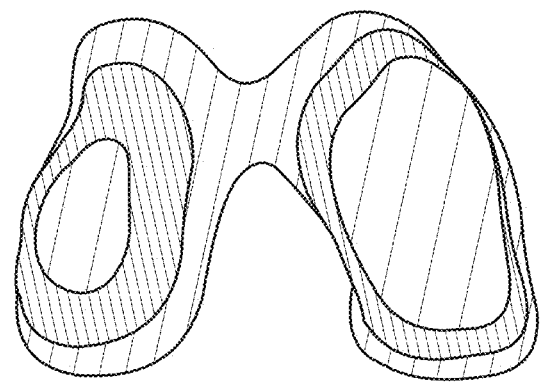
FIG. 15 is superimposed planar view showing how changes in resection depth at the distal end of the femur result in progressively more bone being removed.
Figure 16:
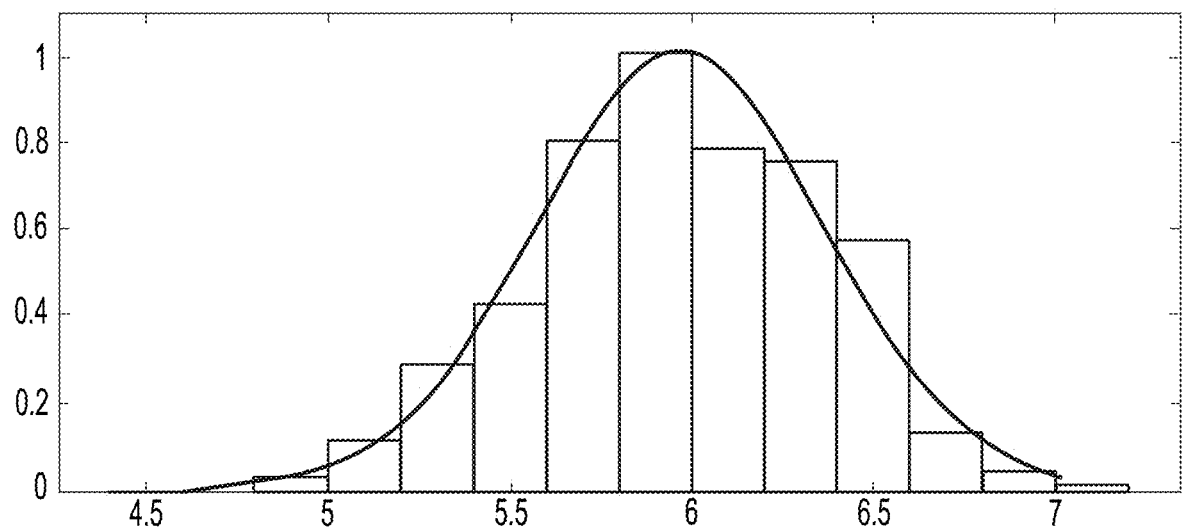
FIG. 16 is a statistical distribution across a statistical atlas population showing how medio-lateral resection width varies across the population.

FIGS. 12-16 reflect an exemplary process for automatic landmarking of the patient bone model 114, this this case the femur, using the pre-operative surgical planning software 104. As depicted in FIG. 12, the software 104 is operative to use statistical atlas automatic landmarking to compute the location of the mechanical axis, the distal resection point, which are both used to compute the suggested, preferred femoral distal resection plane 156. FIG. 13 depicts extraction and measurement of the medio-lateral width of the resection across a given population of the statistical atlas. The extracted and measured medio-lateral widths are used to create the design envelope for the distal cutting slot 200 dimensions (representatives from the statistical atlas population are depicted, with blue reflecting the largest size, green depicting a medium size, and red reflecting the smallest size). FIG. 14 shows the distal femoral resection cuts made to representatives of the statistical atlas. FIG. 15 reflects the relationship between resected medio-lateral dimensions and changes in distal resection plane 156 depth. For instance, the yellow color reflects positioning the resection plane 156 4 millimeters more distal than the planned or suggested resection plane location, whereas red reflects positioning the resection plane at the planned or suggested location and, finally, light blue reflects positioning the resection plane 4 millimeters more proximal than the planned or suggested resection plane location. Finally, FIG. 16 depicts medio-lateral widths across the statistical atlas population to establish cutting slot 200 dimensions that capture most or all of a given population.

Turning to FIGS. 17-20, as an early step in surgical navigation, registration is undertaken to align the image guided surgical system 100 to the patient bone 160. As part of establishing registration, the PAM 130 may be aligned to the patient bone 160 so that the patient specific surface(s) of the PAM match and precisely contact the patient anatomy in only a single orientation and position. Upon positioning the PAM 130 on the patient bone 160 so the PAM occupies the single orientation and position matching precisely the topography of the tissue (e.g., bone), the PAM may be mounted to the patient tissue (e.g., bone) using one or more surgical pins 210 or screws that are received within holes that may be drilled in to the patient tissue. In this fashion, the PAM 130 is rigidly affixed to the patient tissue so that as the tissue is repositioned, so too is the PAM. In addition to mounting the PAM 130 to patient tissue, the rigid reference 170 is also mounted to patient tissue. As discussed herein, the cutting guide 190 is repositionably mounted to the PAM 130 via the mechanical connection.

Figure 17:
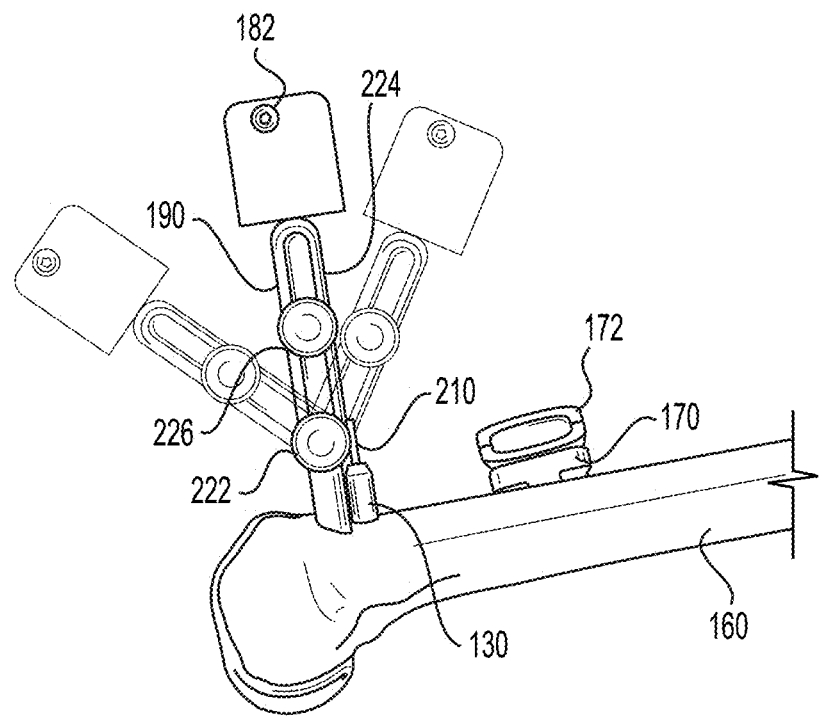
FIG. 17 is a distal femur showing an exemplary cutting guide repositionable among three positions, where a plurality of further positions are possible, and showing how the position of the cutting guide can be changed by pivoting about a lower revolute joint.
Figure 18:
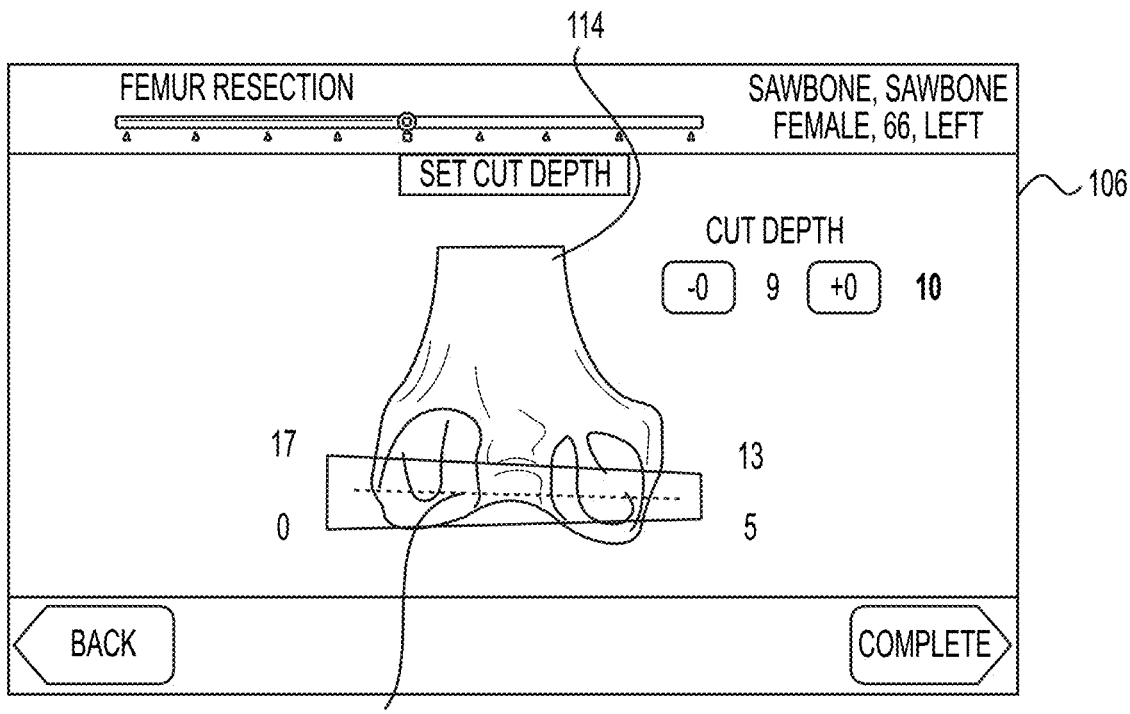
FIG. 18 is a screen shot from a display in accordance with the instant system and disclosure showing a virtual distal femur model and a dotted line showing the pre-operative intended location of the resection with respect to the model.

As depicted in FIGS. 17 and 18, in exemplary form, the cutting guide 190 is mounted to the PAM 130 in a known registration position and orientation using the mechanical connection 220, which is in turn a known position and orientation relative to the patient bone 160 (e.g., the femur) by way of the PAM. More specifically, as depicted in FIG. 17, the lower joint 222 couples the PAM 130 to the adjuster 224, and the upper joint 226 couples the cutting guide 190 to the adjuster. In particular, the cutting guide 190 is oriented so that a dominant longitudinal axis of the cutting slot 200 is parallel to a dominant longitudinal axis of the cutting guide so the axes are co-planar. In addition, a spacing is set between the cutting guide 190 and the PAM 130, along the adjuster 224 using the joints 222, 226, that corresponds to a predetermined spacing that is known. In this manner, the position of the cutting guide 190 in solid lines is the predetermined position with respect to the PAM 130. It should be noted that by adjusting the revolute lower joint 222, the cutting guide 190 may be rotated about the PAM 130 as depicted in phantom lines. When the cutting guide 190 is mounted to the PAM 130, via the mechanical connection 220, and assumes the known registration position (and when the rigid reference 170 is mounted to the patient tissue), data from the IMUs 173, 183 is recorded by the image guided surgical system 100 to establish a point of reference. More specifically, data from the IMUs 173, 183 is processed to determine changes in position and orientation of the cutting guide 190 with respect to the patient bone 160. In this fashion, future motions of the patient bone 160 are tracked independently using the IMU 173 of the rigid reference 170, while motions of the cutting guide 190 are tracked separately using the tracking IMU 183. As a result, as depicted in FIG. 18, the image guided surgical system 100 displays a virtual bone model 114 of the patient's bone 160 along with a phantom line 185 denoting the position and orientation of the cutting slot 200 (that may be color highlighted (e.g., green)) to differentiate between a position of the cutting slot that is or is not consistent with a pre-operative surgical plan establishing the position and orientation of a bone cutting plane.

Figure 19:
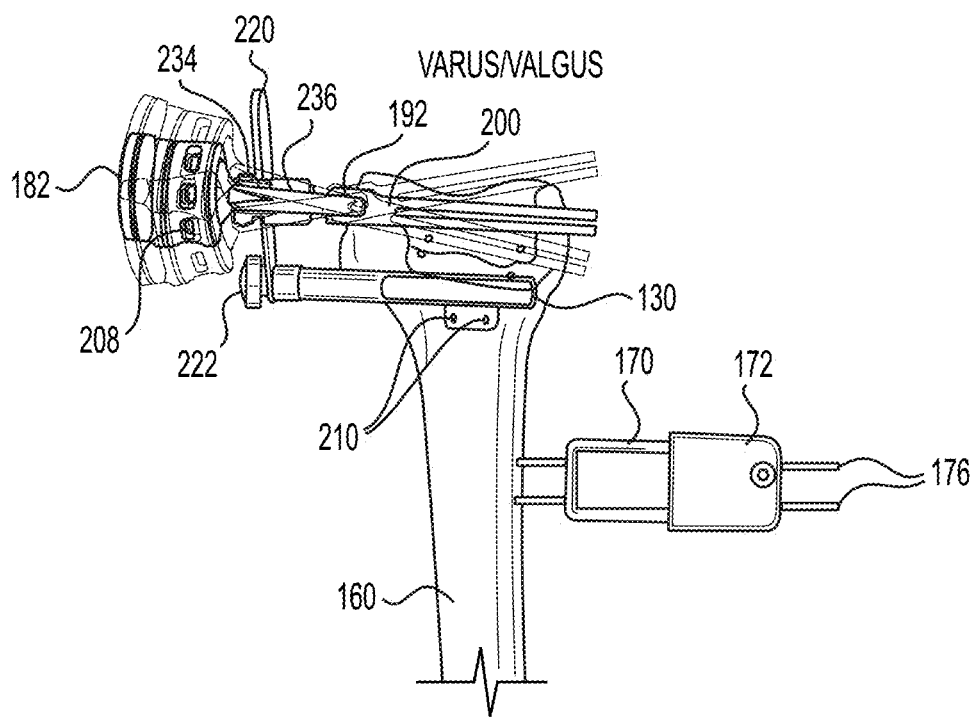
FIG. 19 is a distal femur showing an exemplary cutting guide repositionable among a plurality of positions, where a plurality of further positions are possible, and showing how the position of the cutting guide can be changed by repositioning an upper spherical joint.
Figure 20:
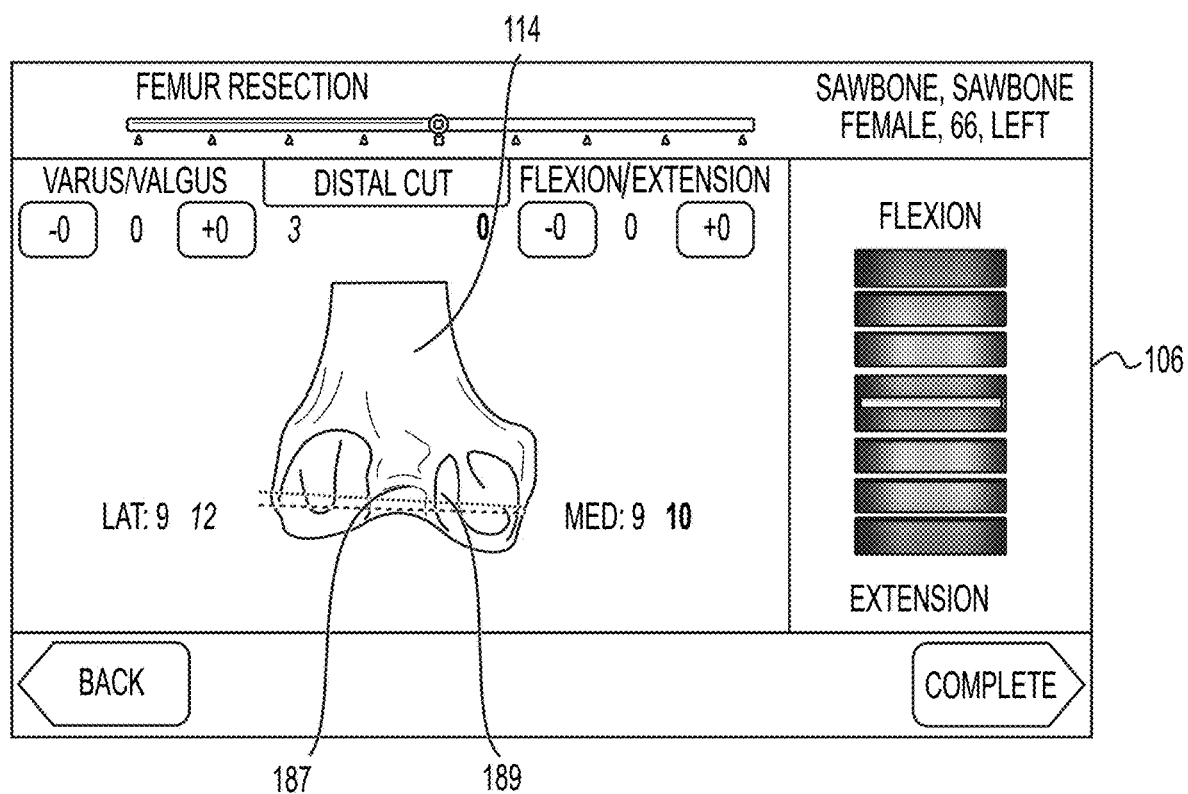
FIG. 20 is a screen shot from a display in accordance with the instant system and disclosure showing a virtual distal femur model and a first dotted line showing the pre-operative intended location of the resection with respect to the model, as well as a second dotted line showing the actual position of the cutting guide slot with respect to the patient anatomy.
Figure 21:
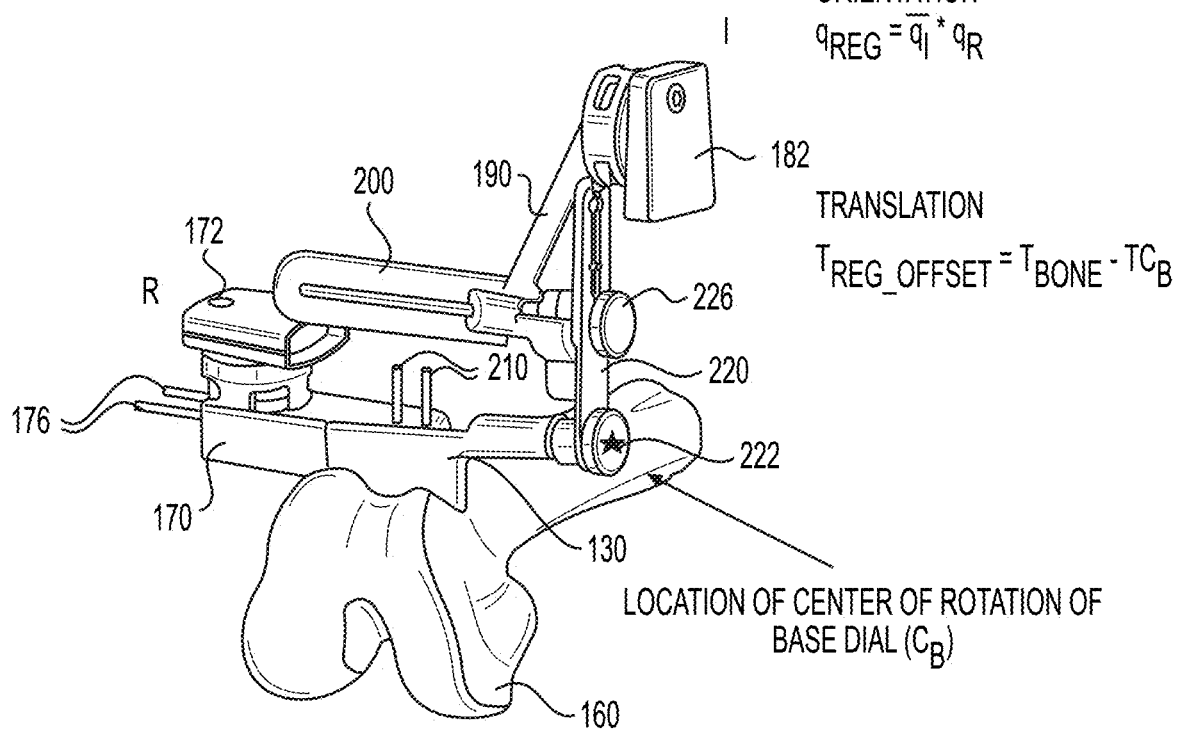
FIG. 21 is an elevated perspective view from the distal end of a femur with components in accordance with the instant disclosure mounted thereto and points of reference for mathematical calculations in accordance with the instant disclosure.

Turning to FIGS. 19 and 20, establishing registration of the cutting guide 190 with respect to the patient bone may also include repositioning of the cutting guide with respect to the mechanical connection 220 using the upper spherical joint 236. In exemplary form, the upper spherical joint 236 allows the guide body 192 to selectively allow the guide body (and cutting slot 200) to be angularly repositioned with respect to the adjuster 224 (and PAM 130) up to 45 degrees with respect to an axis extending parallel to the rotational axis of the revolute joint 234. In this manner, the spherical joint 236 allows for varus or valgus adjustment of the cutting slot 200. By way of example, the solid line position of the cutting guide 190 body 192 is representative of the registration position, whereas the phantom lines are representative of possible changes in angular orientation that the guide body 192 may occupy with respect to the rotational axis of the revolute joint 234. Because the IMU 183 is rigidly mounted to the guide body 192, changes in the position and orientation of the cutting slot 200 are correspondingly reflected in changes in position and orientation of the IMU 183, which sends its data to the image guided surgical system 100. The image guided surgical system uses the data from the IMU 183, along with knowing the dimensions of the guide body 192 and the position of the spherical joint 236 with respect thereto, to calculate the position and orientation of the cutting slot 200. As a result, as depicted in FIG. 20, the image guided surgical system 100 displays a virtual bone model 114 of the patient's bone 160 along with a pair of phantom lines 187, 189 denoting the position and orientation of the cutting slot 200 (that may be color highlighted (e.g., white 189)) with respect to the position and orientation of the intended cutting slot (that may be color highlighted (e.g., green 187)) to differentiate between a position and/or orientation of the cutting slot that is or is not consistent with a pre-operative surgical plan establishing the position and orientation of a bone cutting plane. Post registration, the image guided surgical system 100 may be utilized to facilitate one or more bone cuts at a distal end of the femur as part of a TKA.

Figure 22:
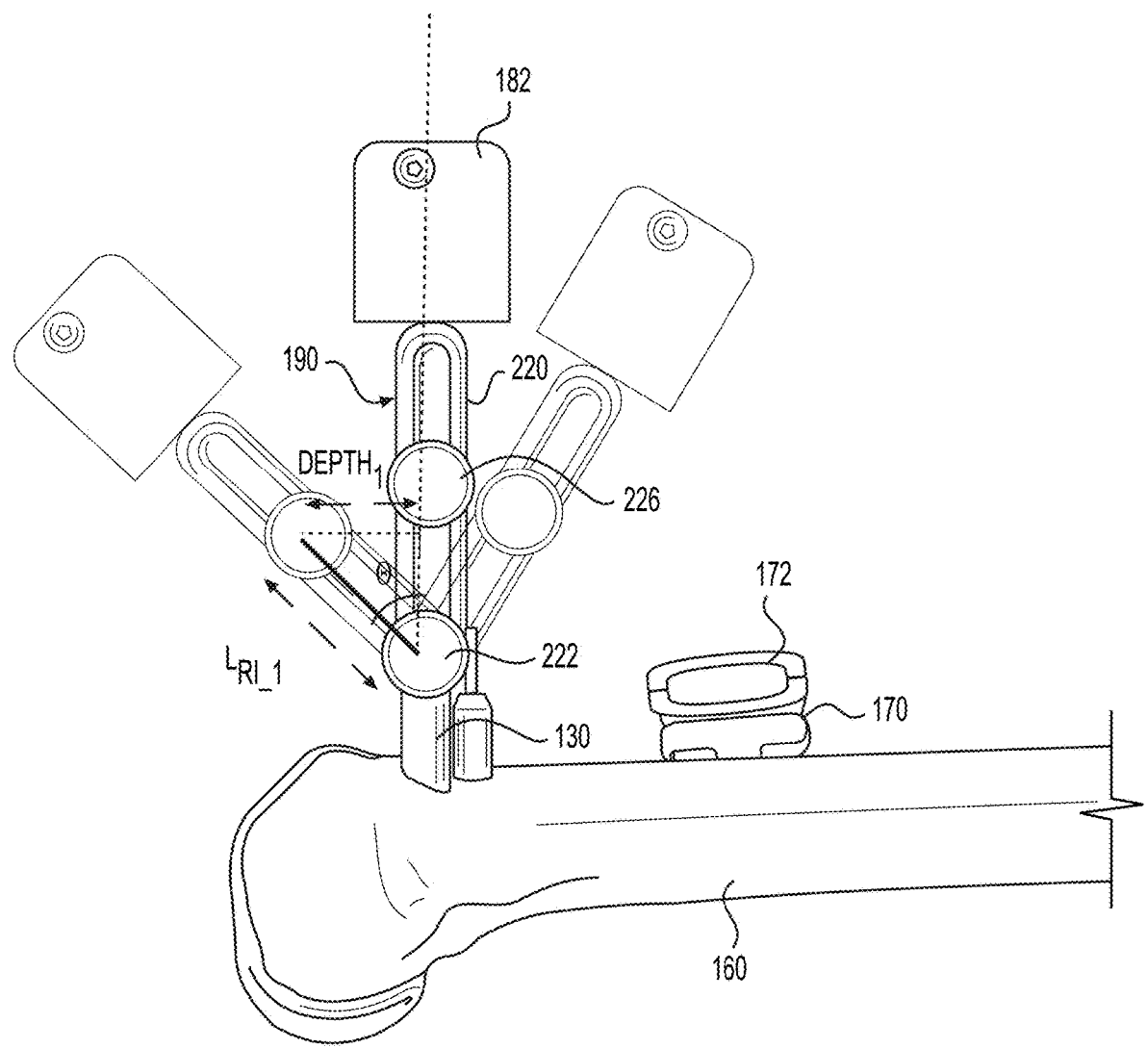
FIG. 22 is a side view of a femur with components in accordance with the instant disclosure mounted thereto and points of reference for mathematical calculations in accordance with the instant disclosure, specific to a lower joint.

Referring to FIG. 22, a TKA surgery may include a distal femoral resection. After registration of the image guided surgical system 100 as previously described, the cutting guide 190 may be repositioned with respect to the PAM using one or both of the joints 222, 226. By way of example, the lower revolute joint 222 may be manipulated so as to allow the cutting guide 190 to rotation around the PAM 130 via a rotational axis extending through the bolt/screw 230 in preparation for the distal femoral resection. In exemplary form, the image guided surgical system 100 may be operative to process data from the IMUs 173, 183 and display virtual bone model 114 of the patient's bone 160 and the relative updated position and orientation of the cutting slot 200 from calculating the relative position and orientation of the cutting guide 190 with respect to the patient's bone. In the context of the lower joint 222, because only a single revolute joint is used, the one or more visual displays 106 may show a "reachable" region, or the allowable range of bone that may be cut by manipulating the upper spherical joint. In particular, using trigonometry, the image guided surgical system 100 calculates the distal-to-proximal distance "$depth_1$" by taking the know distance "$1_{R1\_1}$" between the first and second joints 222, 226 and multiplying by the sine θ, where angle θ is the angle between the registration position of the cutting guide 190 and the current position of the cutting guide. Using data from the IMUs 173, 183, the image guided surgical system 100 is operative to calculate the position of the cutting guide and, correspondingly, calculate angle θ. Using the calculated angle θ, the image guided surgical system 100 then calculates "$depth_1$" and depicts the virtual bone model 114 of the patient's bone 160 and the relative updated position and orientation of the cutting slot 200. In this fashion, the surgeon is able to determine whether the cutting guide 190 should be further rotated with respect to the PAM 130 in accordance with the pre-operative surgical plan to make the correct distal femoral bone cut. Presuming the "$depth_1$" of the femoral bone cut is reached, the surgeon may lock the lower joint 222 in position and focus on repositioning the upper joint 226.

Figure 23:
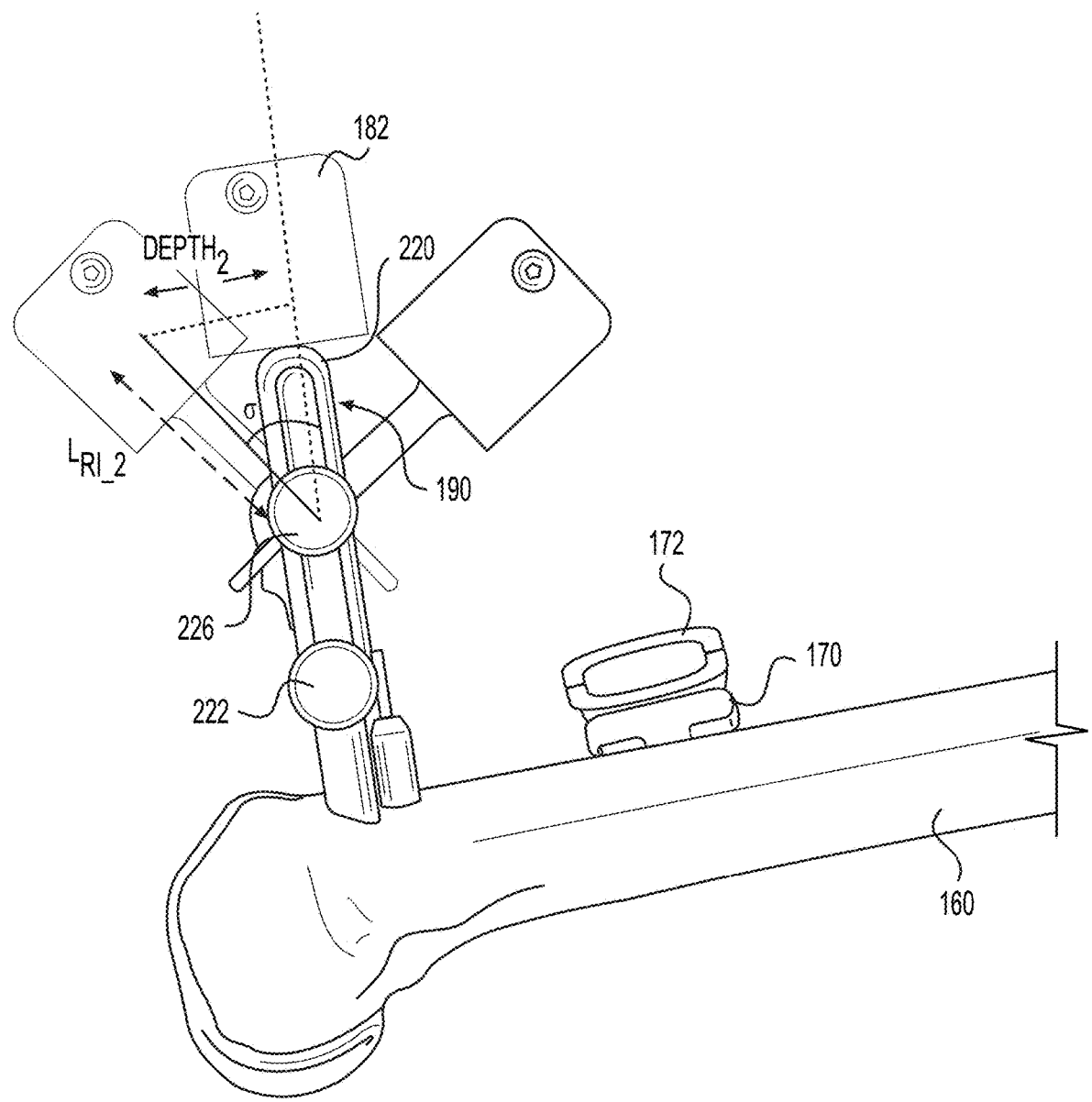
FIG. 23 is a side view of a femur with components in accordance with the instant disclosure mounted thereto and points of reference for mathematical calculations in accordance with the instant disclosure, specific to an upper joint.

Turning to FIG. 23, the upper joint 226 may include a revolute joint 234 and a spherical joint 236. Each may be repositioned to adjust the position of the cutting guide 190 with respect to the PAM 130. In exemplary form, the cutting guide 190 may be allowed to rotate around a rotational axis extending through the bolt/screw 240. Rotation about the bolt/screw 240 may be used to correct for (or make adjustments to) the flexion and extension angle for resection. In particular, using trigonometry, the image guided surgical system 100 calculates the distal-to-proximal distance "$depth_2$" by taking the know distance "$1_{R1\_2}$", between the second joint 226 and the center of the cutting guide body 192, and multiplying by the sine σ, where angle σ is the angle between the registration position of the cutting guide 190 and the current position of the cutting guide with respect to upper joint 226. Using data from the IMUs 173, 183, the image guided surgical system 100 is operative to calculate the position of the cutting guide 190 and, correspondingly, calculate angle σ. Using the calculated angle σ, the image guided surgical system 100 then calculates "$depth_2$" and depicts the virtual bone model 114 of the patient's bone 160 and the relative updated position and orientation of the cutting slot 200. In this fashion, the surgeon is able to determine whether the cutting guide 190 should be further rotated with respect to the second joint 226 in accordance with the pre-operative surgical plan to make the correct distal femoral bone cut. Presuming the "$depth_2$" of the femoral bone cut is reached, the surgeon may lock the upper revolute joint 234 in position and focus on repositioning the spherical joint 236.

Figure 24:
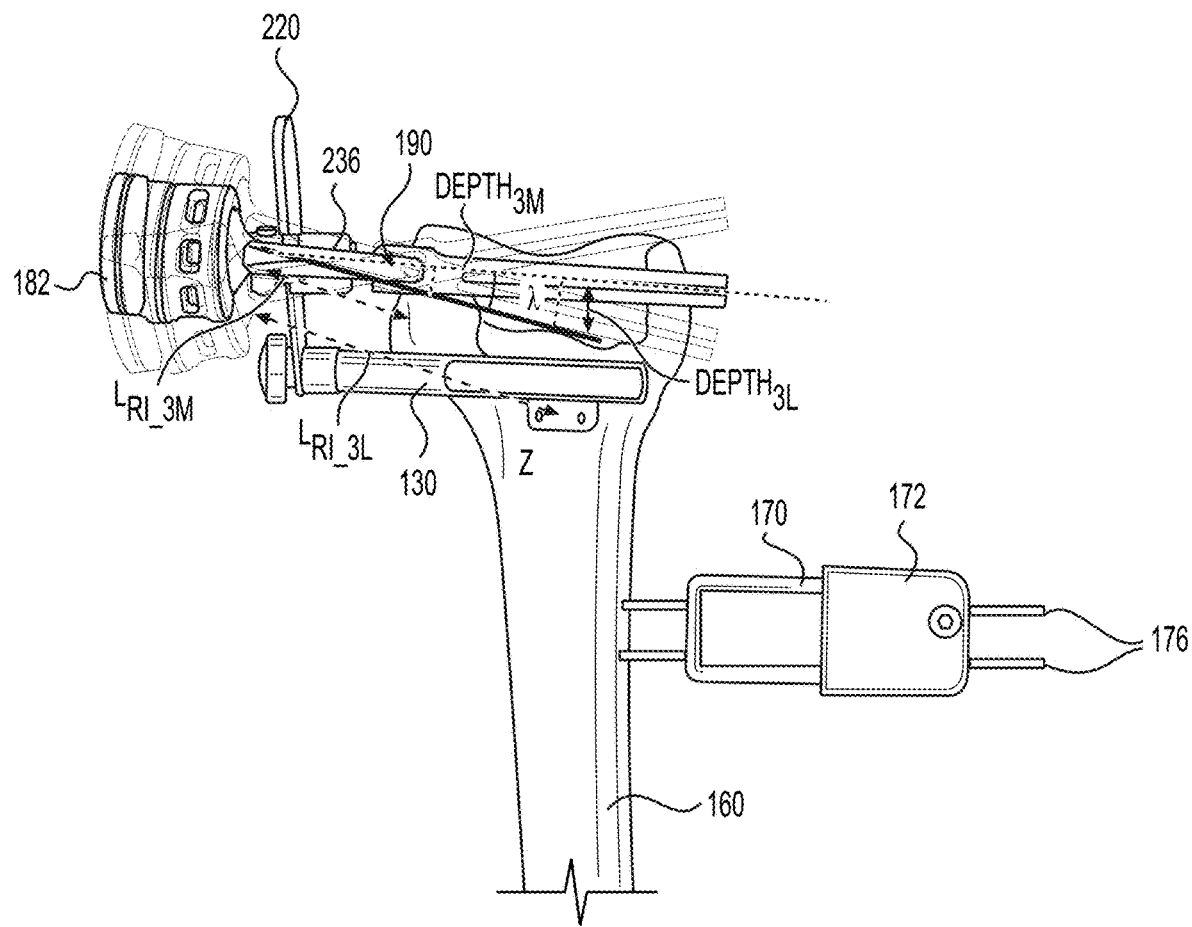
FIG. 24 is an elevated perspective view of a femur with components in accordance with the instant disclosure mounted thereto and points of reference for mathematical calculations in accordance with the instant disclosure, specific to an upper spherical joint.

As depicted in FIG. 24, adjustment of the spherical joint 236 allows for rotation of the cutting slot 200 to accommodate for varus and valgus angular adjustments. In other words, unlocking the spherical joint 236 allows the cutting slot 200 to be manipulated so that the resection depth, varus orientation, and flexion orientation of the cut is acceptable relative to a pre-operative plan. In exemplary form, the cutting guide 190 may be allowed to rotate around a sphere of the spherical joint 236. In particular, using trigonometry, the image guided surgical system 100 calculates medial compartment offset and lateral compartment offset using the following equations:

$\lambda = \text{proj}(q_{current})$ $depth_{3M} = 1_{R1\_3M} * a \sin(\lambda)$ $depth_{medial} = depth_1 + depth_2 + depth_{3M}$ $depth_{3L} = 1_{R1\_3L} * a \sin(\lambda)$ $depth_{lateral} = depth_1 + depth_{2L} + depth_{3L}$ where:
"$1_{R1\_3M}$" is the length of the guide body 192 across the medial compartment;
"$1_{R1\_3L}$" is the length of the guide body 192 across the lateral compartment;
angle "λ" is the angle between the registration position and the angular offset.

Figure 25:
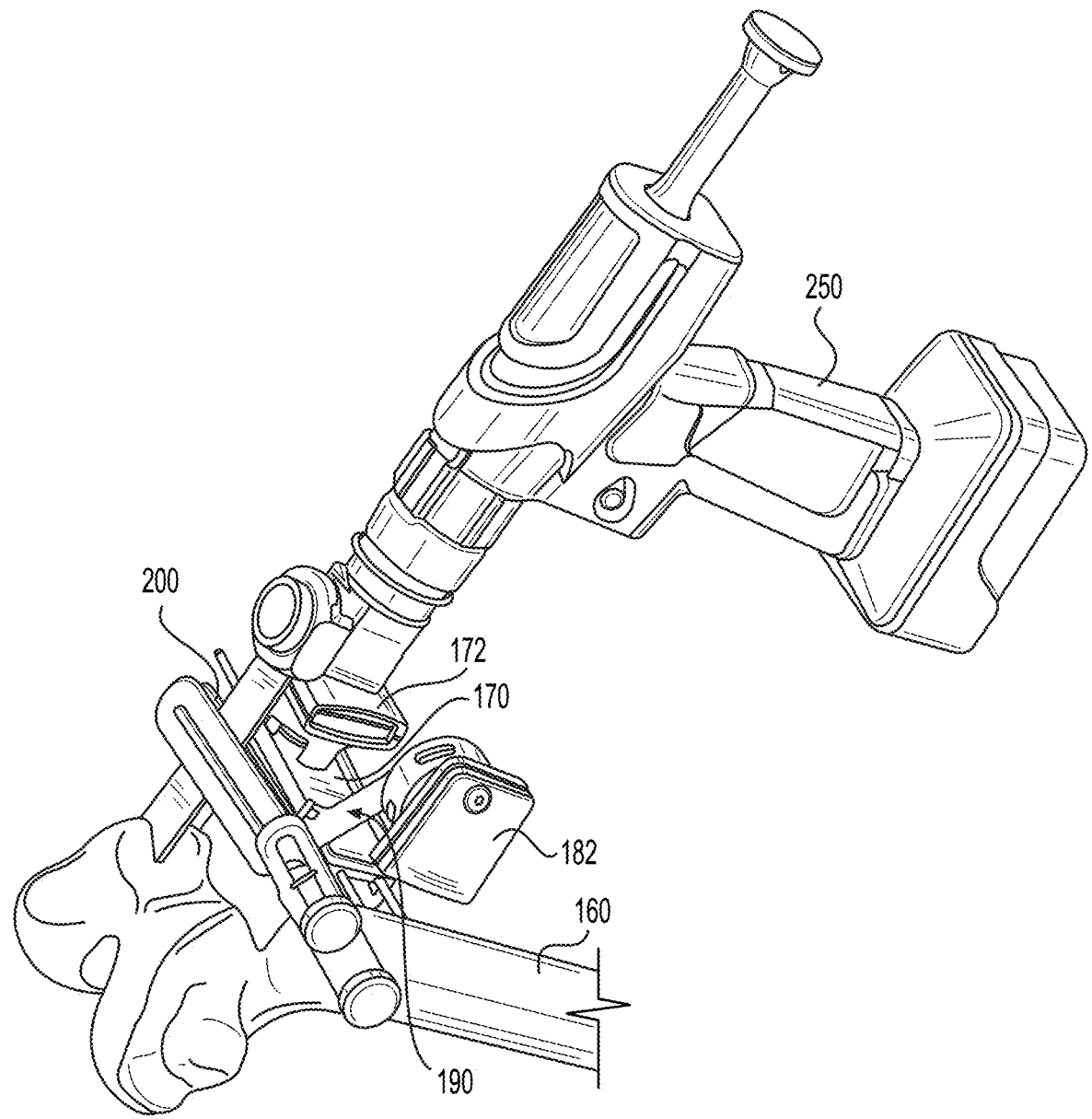
FIG. 25 is an elevated perspective view of a distal end of the femur showing components in accordance with the instant disclosure mounted thereto and being used to guide a surgical saw as part of making a distal femoral resection cut.
Figure 26:
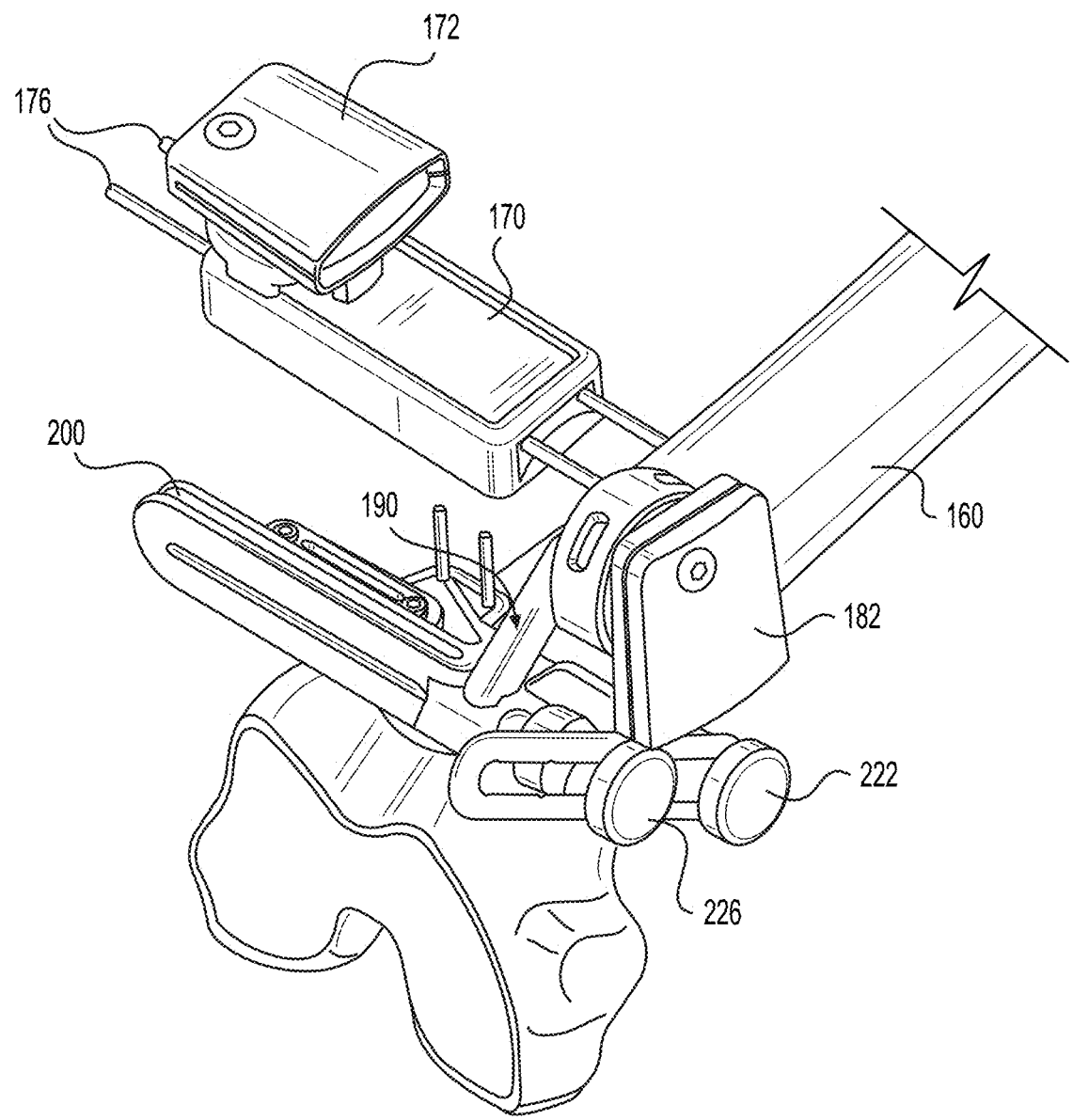
FIG. 26 is an elevated perspective view of a distal end of the femur showing components in accordance with the instant disclosure mounted thereto after making the distal femoral resection cut.
Figure 27:
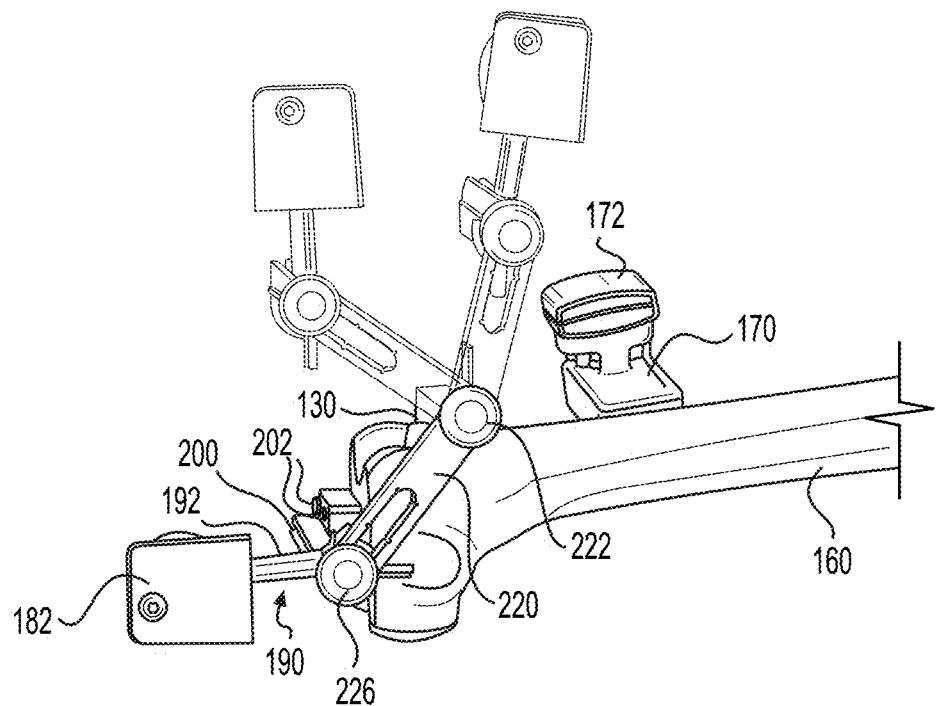
FIG. 27 is an elevated perspective view of a distal end of the femur showing components in accordance with the instant disclosure mounted thereto and having the cutting guide repositioned in anticipation of surgical pin placement into the resected femur after making the distal femoral resection cut.

Referring to FIGS. 22-26, presuming the "$depth_2$" of the femoral bone cut is reached, the surgeon may lock the upper revolute joint 234. Accordingly, to get the medial depth offset "$depth_{3M}$", the known length of "$1_{R1\_3M}$" is multiplied by sine λ. Likewise, to get the lateral depth offset "$depth_{3L}$", the known length of "$1_{R1\_3L}$" is multiplied by sine λ. In order to calculate the actual resection depth in the medial compartment. "depth$_1$" and "depth$_2$" and "depth$_{3M}$" are summed (see FIGS. 22-24). Similarly, to calculate the actual resection depth in the lateral compartment, "depth$_1$" and "depth$_2$" and "depth$_{3L}$" are summed (see FIGS. 22-24). Using data from the IMUs 173, 183, the image guided surgical system 100 is operative to calculate the foregoing. In this fashion, the surgeon is able to determine whether the cutting guide 190 should be further rotated about the spherical joint 236 in accordance with the pre-operative surgical plan to make the correct distal femoral bone cut. Once the position and orientation of the cutting guide 190 is acceptable, the joints 222, 226, 236 may be locked and the distal femoral resection cut may be undertaken, as depicted in FIGS. 25 and 26, with a surgeon controlling a surgical saw 250.

Referring to FIGS. 27-30, after the distal femoral resection cut is completed, the cutting guide 190 and PAM 130 may be used to facilitate placement of fixation devices (e.g., surgical pins 210) that will guide and engage a fixed position cutting block 300. In femoral TKA surgical procedures, having five bone cuts, the remaining cuts (besides the distal femoral resection) are the anterior, posterior, and two chamfer cuts. To facilitate these four bone cuts, one may make use of a conventional instrument, referred to as the 4-in-1 cutting block 300. This cutting block 300, which is fixed to the distal end of a patient's resected femur 160, includes two or more openings configured to receive two or more surgical pins 210 extending from the resected distal surface. In this fashion, the surgical pins 210 are operative to align the cutting block 300 with respect to the distal femur and to guide the cutting block into position against the resected femur surface. In addition to the openings configured to receive the surgical pins 210, the cutting block 300 includes four or more cutting slots, each cutting slot belonging to one of the four mentioned remaining bone cuts. It should be noted, however, that different knee implants may require different cutting positions and even different numbers of bone cuts. Nevertheless, the exemplary devices and methods disclosed herein may be applied to any cutting guide (e.g., smart or dumb) whether placed by physical alignment guides or via computer feedback or control.

Figure 28:
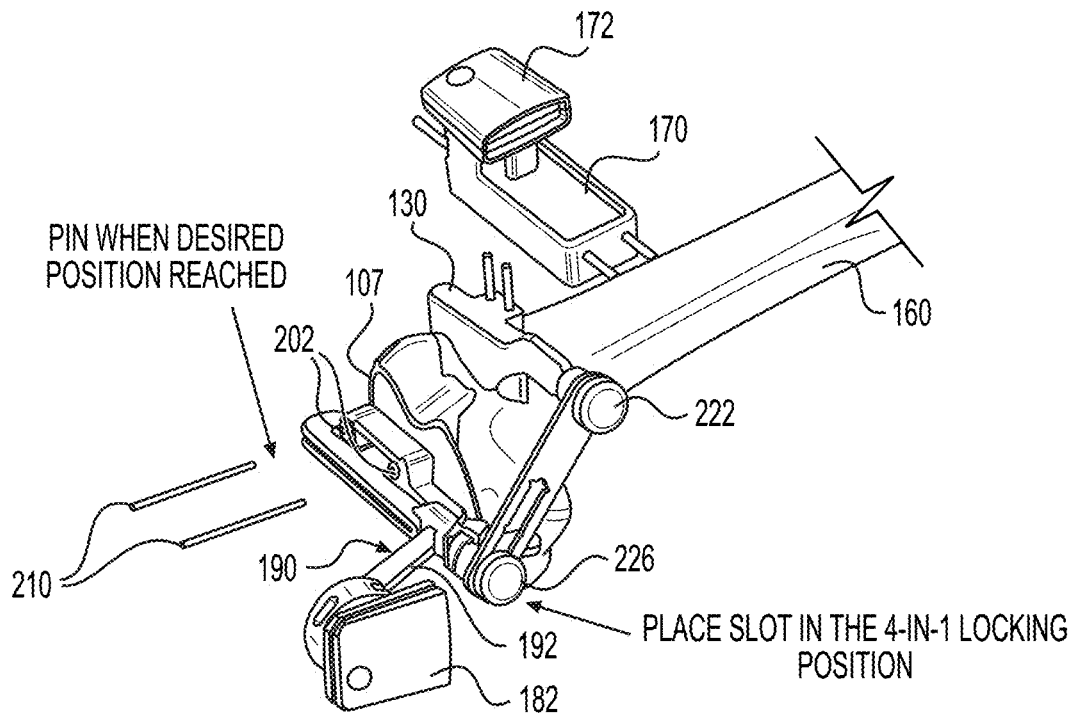
FIG. 28 is an elevated perspective view of a distal end of the femur showing components in accordance with the instant disclosure mounted thereto, after making the distal femoral resection cut, in anticipation of surgical pin placement into the resected femur.
Figure 29:
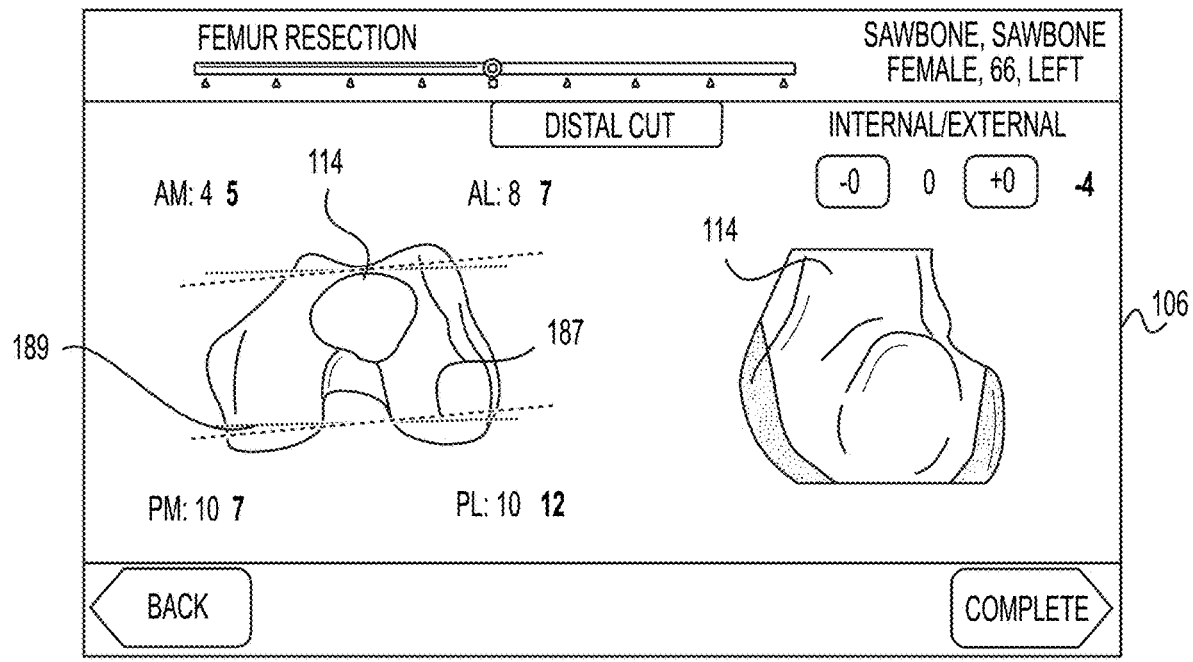
FIG. 29 is a screen shot from a display in accordance with the instant system and disclosure showing a first virtual distal femur model and a first dotted line showing the pre-operative intended location of the resection with respect to the model, as well as a second dotted line showing the actual position of the cutting guide slot with respect to the patient anatomy (for both the anterior cut and the posterior cut), as well as a second virtual model from a profile view showing the distal resection and areas of the femur yet to be resected.

As depicted in FIGS. 28 and 29, in order to prepare the resected femur for using the 4-in-1 cutting block 300, the image guided surgical system 100 provides instructions via the one or more visual displays 106 for repositioning the cutting guide 190 so that the guide body 192 is positioned against the exposed surface of the resected distal femur 107 based upon data from the IMUs 173, 183. In particular, the guide body 192 is positioned so that one or more though orifices 202 are aligned with intended locations of the resected femur 107 so that a surgical drill may extend through the orifices and drill out holes within the femur. The pin holes dictate the internal-external rotation and anterior-posterior positioning of the remaining bone cuts. Post hole creation, two or more surgical pins 210 are placed, one in each hole, optionally using the guide body orifices 202 to align the surgical pins into position so that the surgical pins extend into the resected femur and extend distally generally perpendicular to the resected, femoral planar surface. After the surgical pins 210 are mounted to the resected femur, the cutting guide 190 and PAM 130 may be removed from the surgical site.

Figure 30:
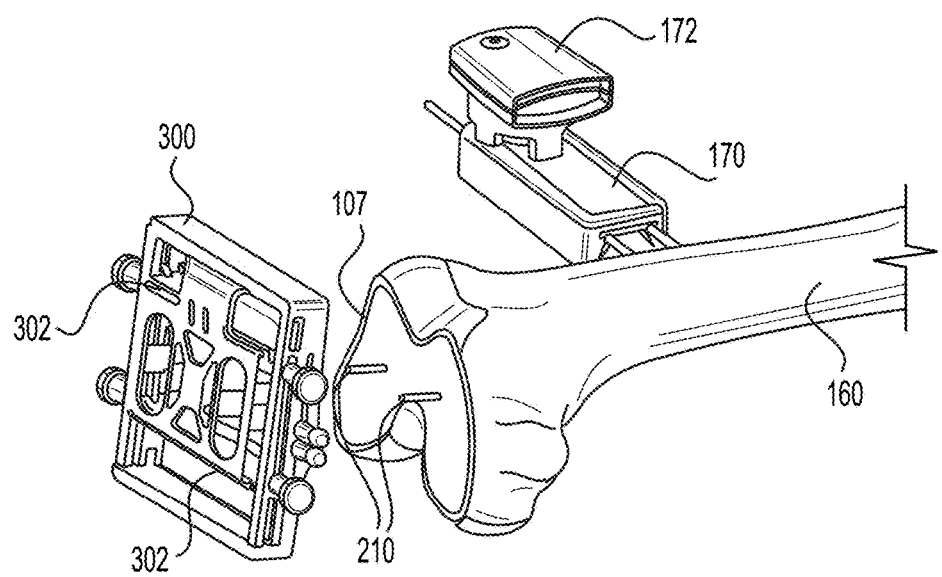
FIG. 30 is an elevated perspective view of a distal end of the femur showing components in accordance with the instant disclosure mounted thereto and having a 4-in-1 cutting guide to be mounted to the resected femur using pins installed as depicted in FIG. 28.

Turning to FIGS. 30 and 31, with the surgical pins 210 in position on the resected femur 107, a 4-in-1 cutting block 300 is aligned with respect to the distal resected femur 107 so that two or more openings of the cutting block 300 are configured to receive the two or more surgical pins 210 so that the cutting block may be repositioned against the exposed bone surface of the distal femoral resection cut. With the cutting block aligned using the surgical pins 210 and against the resected distal femur surface, the surgeon may lock the cutting block 300 in position. Thereafter, the surgeon may reposition a surgical blade through the respective slots 302 of the block 300 to make the anterior, posterior, and two chamfer distal femur cuts. After completion of the bone cuts (see FIG. 31), the block 300 and surgical pins 210 may be removed from the distal femur in anticipation of orthopedic trial fitting. While the foregoing exemplary surgical procedure makes use of a 4-in-1 cutting block 300 to make the anterior, posterior, and two chamfer distal femur cuts, it is also within the scope of the disclosure to utilize the cutting guide 190, the PAM 130, and a guide foot 260.

Referencing FIGS. 32-37, after the distal femoral resection cut is completed, the cutting guide 190 and PAM 130 may be used to facilitate placement of fixation devices (e.g., surgical pins 210) that will guide and engage the guide foot 260. As discussed herein, femoral TKA surgical procedures generally include five bone cuts, four of which remain after the distal femoral resection has been completed. To facilitate these four bone cuts, one may make use of the guide foot 260 that replaces the PAM 130 as the anchor to which the mechanical connection 220 and the cutting guide 190 are mounted.

As depicted in FIG. 32, after the PAM 130, mechanical connection 220, and cutting guide 190 have been utilized to position the surgical pins 210, the foregoing components may be removed from the surgical site. In exemplary form, the PAM 130 is replaced with a guide foot 260 that connects to the mechanical connection 220 just as the PAM did, so that the guide foot, mechanical connection, and cutting guide 190 are mounted to one another. In exemplary form, the guide foot 260 includes two or more orifices configured to receive, respectively, the surgical pins 260 extending from the resected portion of the femur 107. The orifices of the guide foot 260 are configured to receive the surgical pins 210 in only a single orientation so that, when the guide foot receives the surgical pins and is repositioned against the resected femur 107 and affixed in position, the image guided surgical system 100 knows precisely the position and orientation of the guide foot with respect to the femur.

In this exemplary embodiment, the image guided surgical system 100 is programmed with the precise dimensions of the guide foot 260 so that when the guide foot is in a registration position, the position of the cutting guide 190 with respect to the femur is known. In other words, the cutting guide 190 is mounted to the guide foot 260 in a known registration position and orientation using the mechanical connection 220, which is in turn a known position and orientation relative to the patient bone 160 (e.g., the femur) by way of the guide foot.

As discussed herein, the lower joint 222 couples the guide foot 260 to the adjuster 224, and the upper joint 226 couples the cutting guide 190 to the adjuster. In particular, the cutting guide 190 is oriented so that a dominant longitudinal axis of the cutting slot 200 is parallel to a dominant longitudinal axis of the cutting guide so the axes are co-planar. In addition, a spacing is set between the cutting guide 190 and the guide foot 260, along the adjuster 224 using the joints 222, 226, that corresponds to a predetermined spacing that is known. In this manner, the position of the cutting guide 190 is known with respect to the guide foot 260. When the cutting guide 190 is mounted to the guide foot 260, via the mechanical connection 220, and assumes the known registration position (and when the rigid reference 170 is mounted to the patient tissue), data from the IMUs 173, 183 is recorded by the image guided surgical system 100 to establish a point of reference for the cutting guide 190 having a known position and orientation with respect to the resected femur. And, as discussed hereafter, this point of reference is utilized by the image guided surgical system 100 to track and inform a user (e.g., a surgeon) concerning the position and orientation of the cutting guide to facilitate utilizing the cutting guide to perform the anterior, posterior, and two chamfer distal femur cuts.

Figure 34:
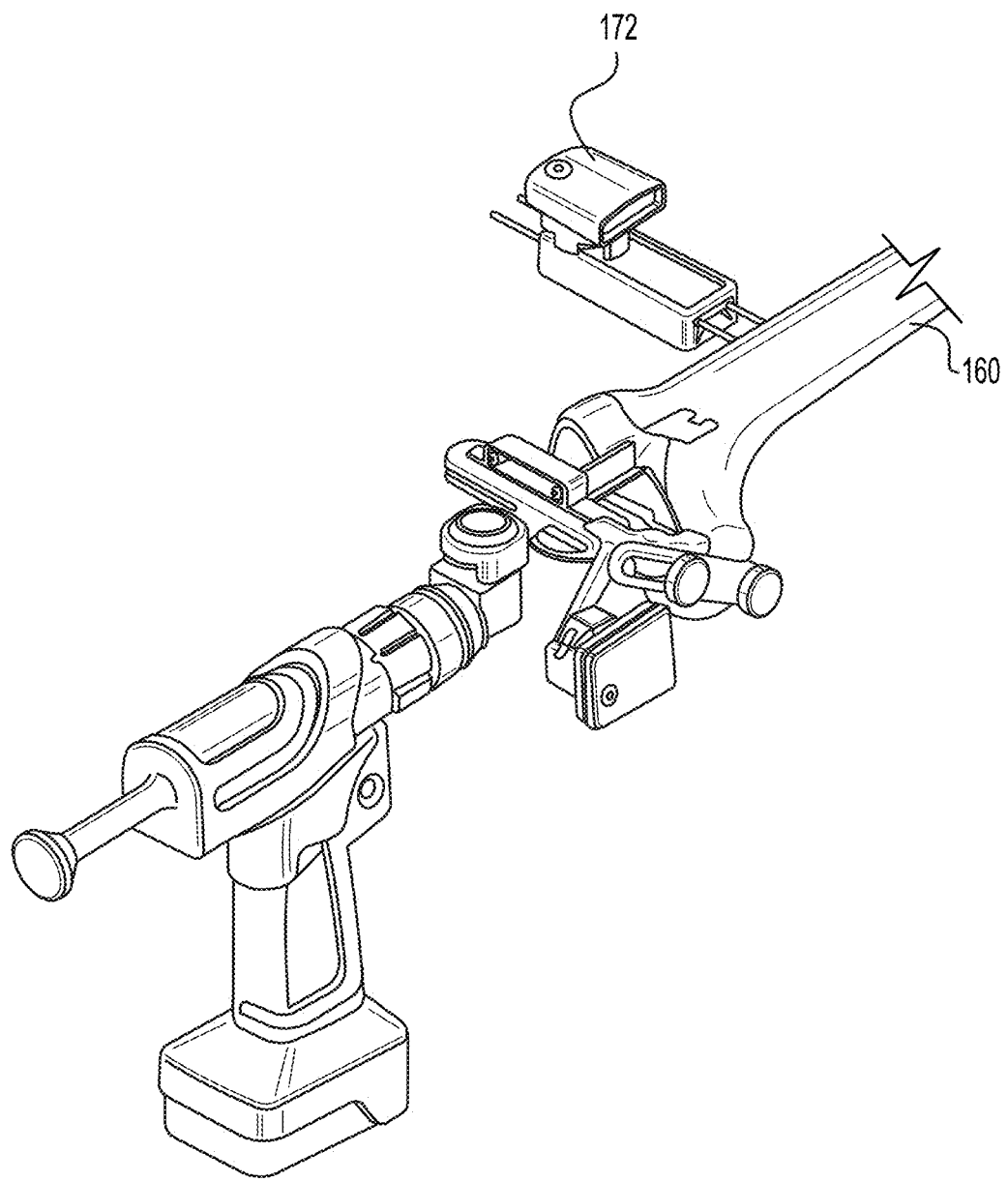
FIG. 34 is an elevated perspective view of a distal end of the femur showing components in accordance with the instant disclosure mounted thereto and being used to guide a surgical saw as part of making an anterior femoral resection cut.
Figure 35:
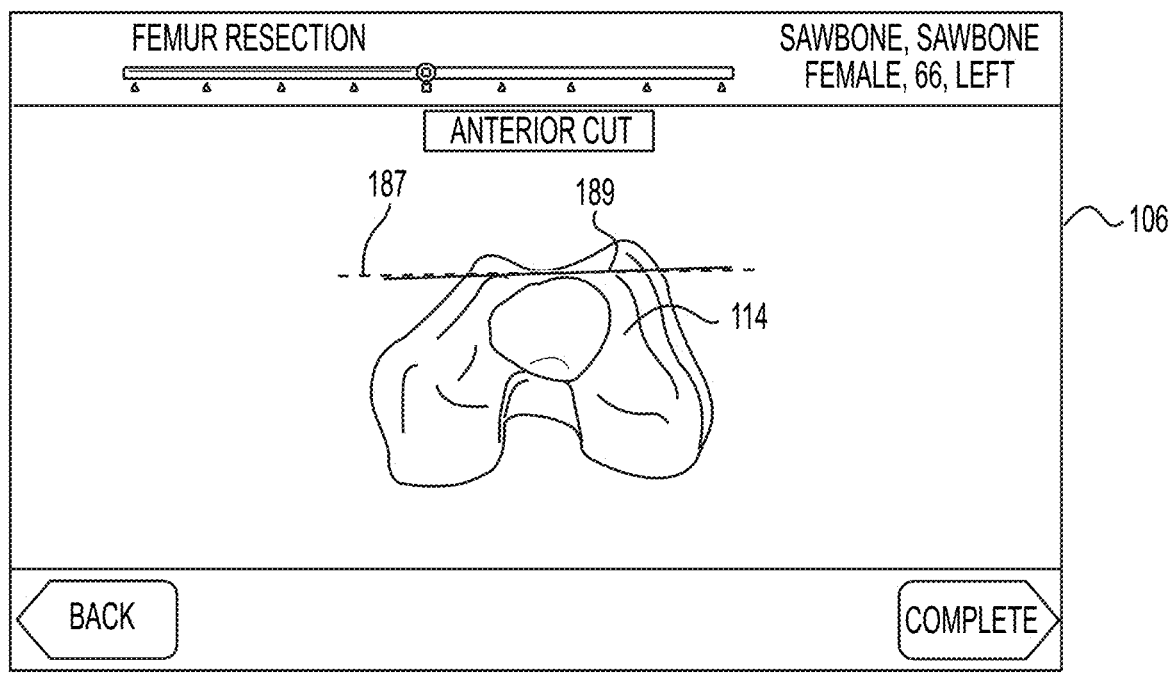
FIG. 35 is a screen shot from a display in accordance with the instant system and disclosure showing a first virtual distal femur model and a first dotted line showing the pre-operative intended location of the anterior resection with respect to the model, as well as a second dotted line showing the actual position of the cutting guide slot with respect to the patient anatomy.
Figure 36:
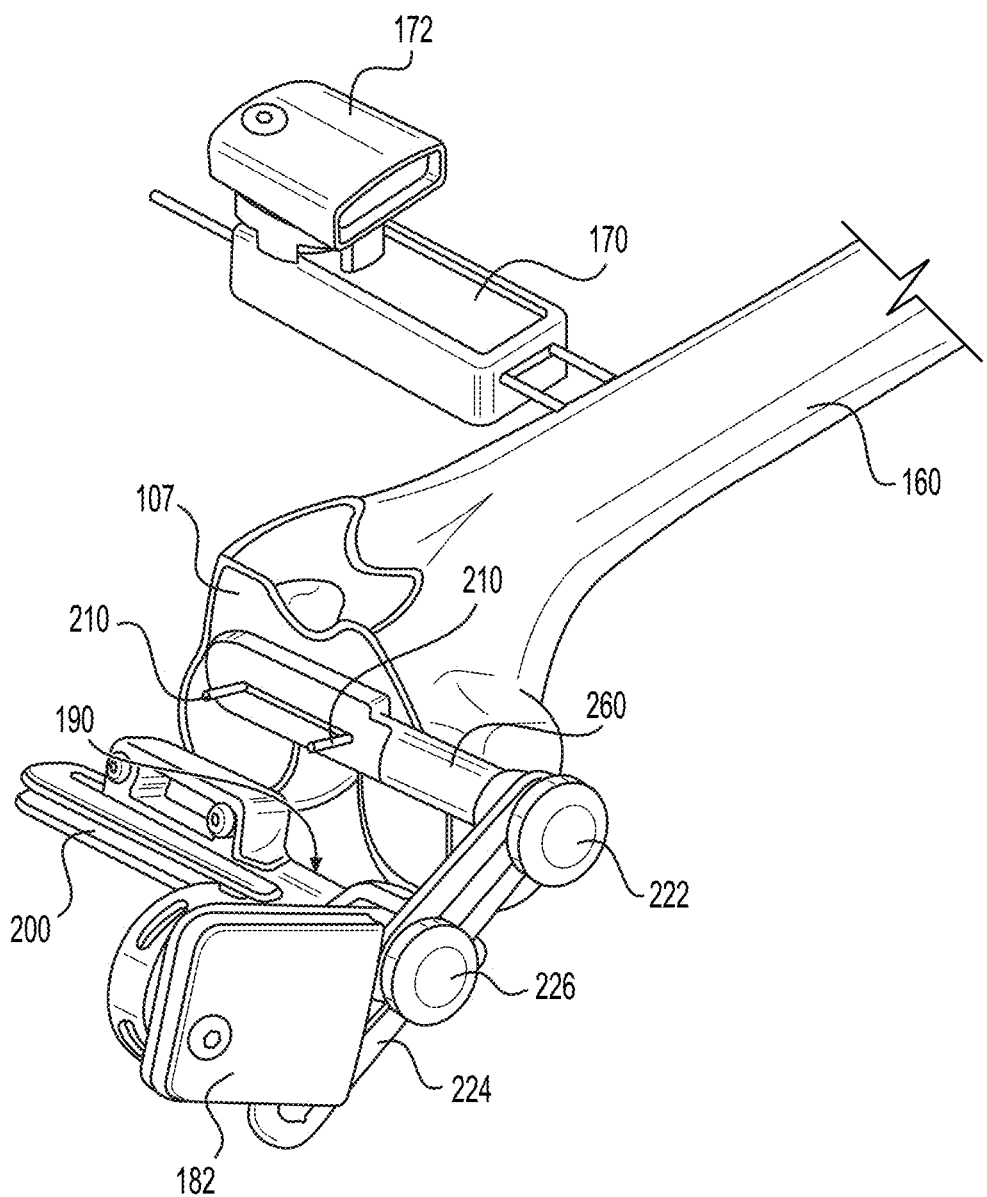
FIG. 36 is an elevated perspective view of a distal end of the femur showing components in accordance with the instant disclosure mounted thereto and being used to guide a surgical saw as part of making a posterior femoral resection cut.
Figure 37:
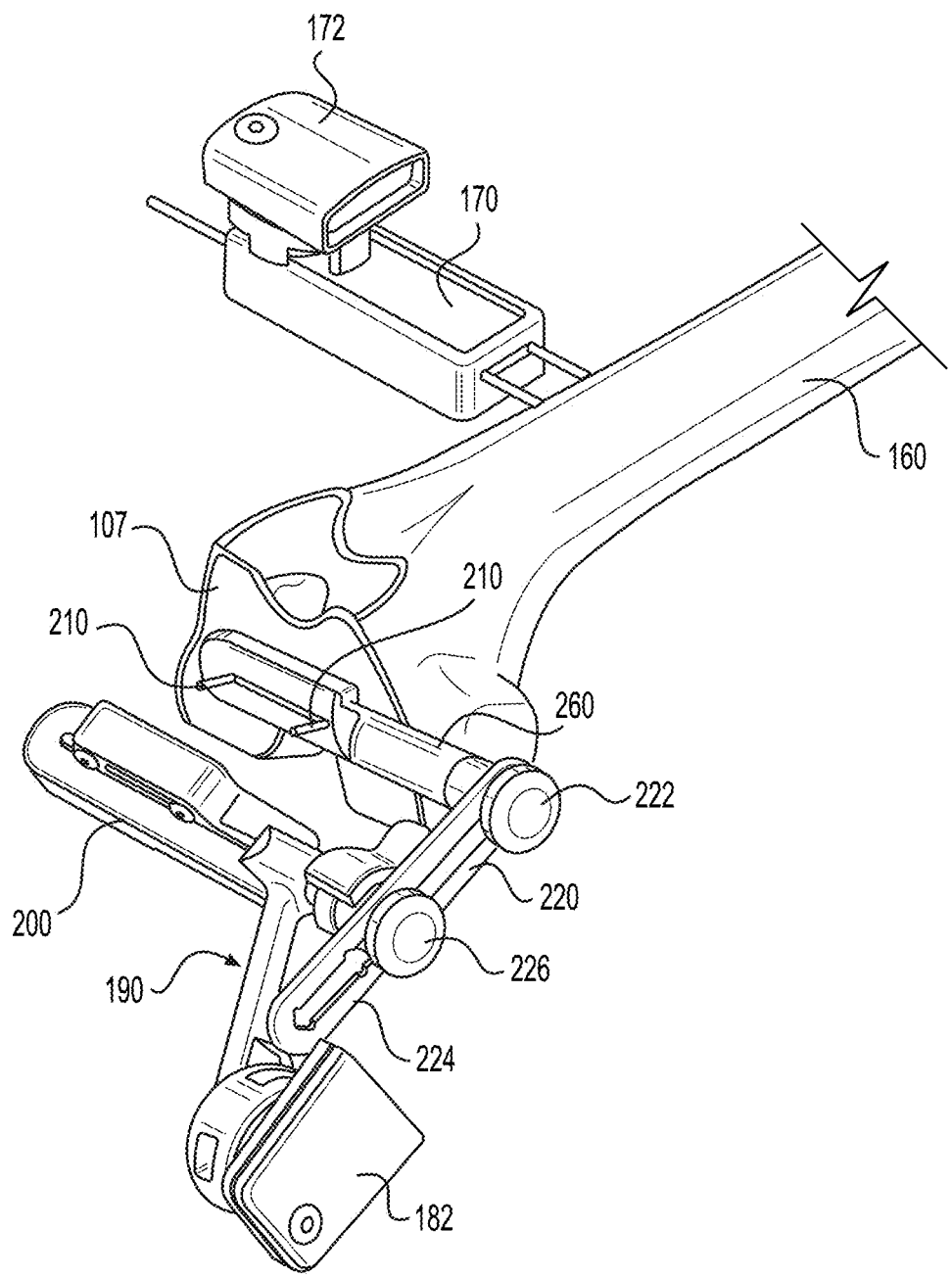
FIG. 37 is an elevated perspective view of a distal end of the femur showing components in accordance with the instant disclosure mounted thereto and being used to guide a surgical saw as part of making an anterior chamfer femoral resection cut.
Figure 38:
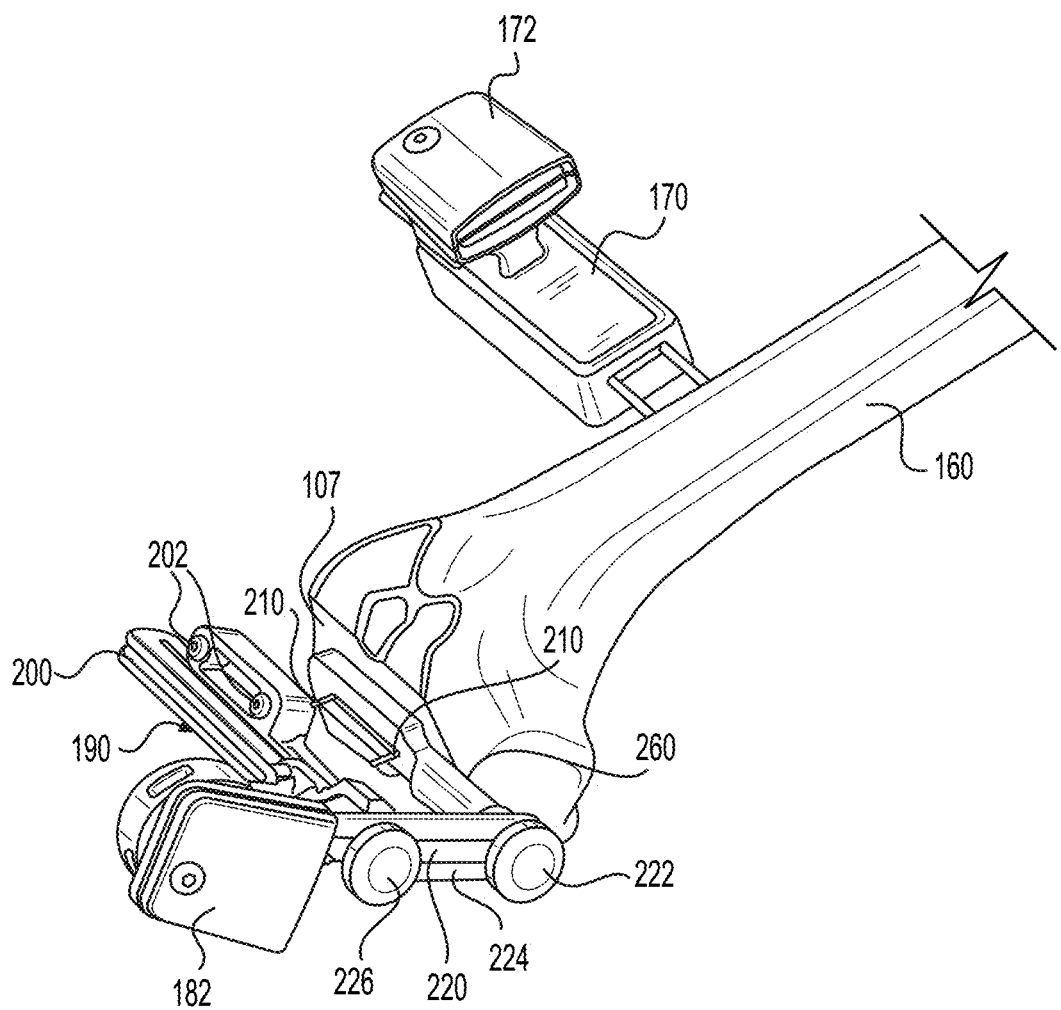
FIG. 38 is an elevated perspective view of a distal end of the femur showing components in accordance with the instant disclosure mounted thereto and being used to guide a surgical saw as part of making a posterior chamfer femoral resection cut.

Referring to FIGS. 34 and 35, data from the IMUs 173, 183 is processed by the image guided surgical system 100 to determine changes in position and orientation of the cutting guide 190 with respect to the patient bone 160. In this fashion, motions of the patient bone 160 are tracked independently using the IMU 173 of the rigid reference 170, while motions of the cutting guide 190 are tracked separately using the tracking IMU 183. As a result, the image guided surgical system 100 displays a virtual bone model 114 of the patient's bone 160 along with a phantom line 310 color coded (e.g., green) to confirm that the intended cut line is in accordance with a pre-operative surgical plan. In this exemplary sequence, the surgeon may reposition the cutting guide 190 by loosening and tightening the revolute joints 222, 234 and the spherical joint 236 in order to position and orient the cutting slot 200 to make the requisite cuts in accordance with the pre-operative surgical plan, namely the anterior cut as depicted in FIG. 34. The one or more visual displays 106 are updated in real-time or near real-time to depict the bone model 114 consistent with the position and orientation the patient's actual bone with respect to the projected cutting line, which passes through the cutting slot 200. Consequently, when the cutting guide 190 is positioned and oriented consistent with the pre-operative surgical plan, the surgeon may visually confirm the position using the one or more visual displays 106 and carry out the bone cut by using a surgical saw 250 having a blade received within the cutting slot 200. This process is repeated by repositioning the cutting guide 190 via loosening and tightening the revolute joints 222, 234 and the spherical joint 236 in order to reposition and reorient the cutting slot 200 to also make the posterior cut (see FIG. 36), the anterior chamfer cut (see FIG. 37), and the posterior chamfer cut (see FIG. 38). After making the last four (or so) bone cuts using the cutting guide 190, the cutting guide, mechanical connection 220, and the guide foot 260 may be removed from the surgical pins 210 and away from the surgical site. Likewise, the surgical pins 210 may be removed from the distal resected femur to accommodate orthopedic trial test fitting. But the instant embodiments can also be used with bone cuts beyond the distal femoral cuts.

Figure 39:
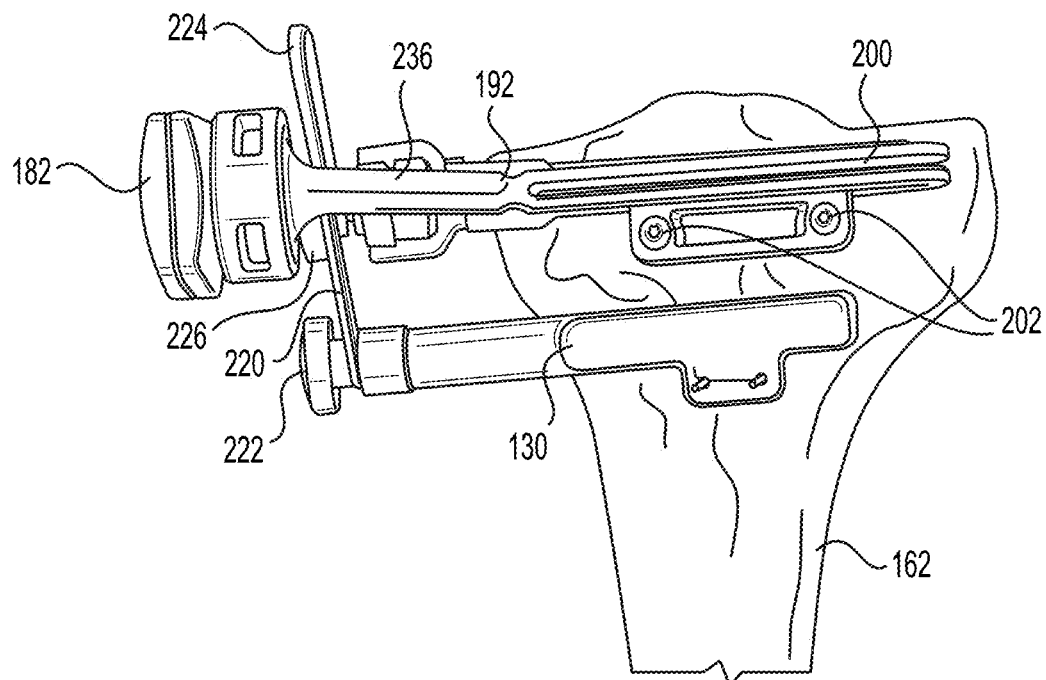
FIG. 39 is a frontal view of a proximal end of the tibia showing components in accordance with the instant disclosure mounted thereto and having the cutting guide repositioned in anticipation of making the proximal tibial resection cut.
Figure 40:
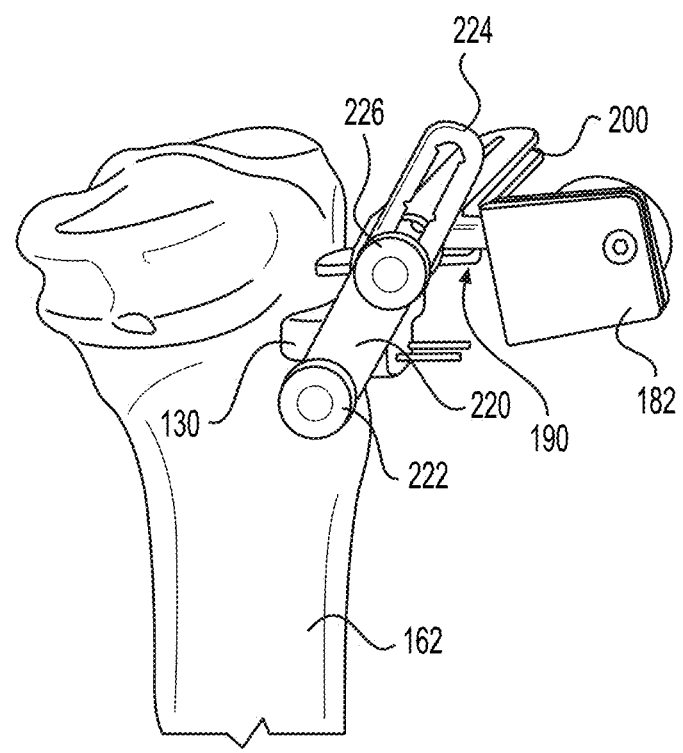
FIG. 40 is an elevated perspective view of the tibia and components of FIG. 39.

Referencing FIGS. 39 and 40, it is also in accordance with the instant disclosure that the image guided surgical system 100 be utilized to guide bone cuts beyond those of the distal femur. By way of example, the image guided surgical system 100 may be utilized to carry out the tibia resection as part of a TKA procedure (revision or replacement). For example, the image guided surgical system 100 may make use of the same workstation 102, software 104, visual displays 106, mechanical connections 220, and surgical instruments 170, 190. But what differs are the patient-specific virtual tissue models 114 (which comprise a proximal tibia, rather than a distal femur discussed above) and the PAM 130 (PAM for femur is not the same as the PAM for the tibia).

In this exemplary discussion, the PAM 130 is configured to have at least one surface with a geometry matching the negative of the patient's proximal tibia (in other words, the surface shape of the PAM precisely follows the surface, including shape changes, of the patient's proximal tibia). By utilizing a PAM 130 that fits to the patient's tibia in only a single location and orientation, instrumentation or other parts having known geometries (size, width, length, height, etc.) may be attached to the PAM to facilitate localization of position and orientation of the instrumentation or other parts within a frame of reference utilized by the surgical navigation software 104. In other words, because one knows the exact position and orientation of the PAM 130 with respect to a patient's tibia, any structure (having known dimensions) rigidly mounted to the PAM will also have a known position and orientation with respect to the patient's tibia. In this fashion, the PAM 130 operates to correlate the virtual frame of reference with the real-world frame of reference.

In the context of the instant disclosure, virtual pre-operative surgical planning may establish the position and orientation of the proximal tibia resection bone cut for a TKA, as well as the placement of the PAM 130 on the patient's tibia 162. As part of this pre-operative surgical planning, the image guided surgical system 100 makes use of a registration to align the image guided surgical system to the patient 110. As part of establishing registration, the PAM 130 is aligned to the patient so that the patient specific surface(s) of the PAM match and precisely contact the patient's tibia in only a single orientation and position. Upon positioning the PAM 130 on the patient's tibia 162 so the PAM occupies the single orientation and position matching precisely the topography of the tibia, the PAM may be mounted to the tibia using one or more surgical pins 132 or screws that are received within holes that may be drilled into the tibia. In this fashion, the PAM 130 is rigidly affixed to the tibia so that as the tibia is repositioned, so too is the PAM. In addition to mounting the PAM 130 to patient tissue, a rigid reference (not shown) is also mounted to the tibia. Similarly, as discussed before, the cutting guide 190 is repositionably mounted to the PAM 130 via the mechanical connection 220.

In exemplary form, the cutting guide 190 is mounted to the PAM 130 in a known registration position and orientation using the mechanical connection 220, which is in turn a known position and orientation relative to the patient bone (e.g., the tibia 162) by way of the PAM. Consistent with the prior discussion, the lower joint 222 couples the PAM 130 to the adjuster 224, and the upper joint 226 couples the cutting guide 190 to the adjuster. In particular, the cutting guide 190 may be oriented so that a dominant longitudinal axis of the cutting slot 200 is parallel to a dominant longitudinal axis of the cutting guide so the axes are co-planar. In addition, a spacing is set between the cutting guide 190 and the PAM 130, along the adjuster 224 using the joints 222, 226, that corresponds to a predetermined spacing that is known. It should be noted that by adjusting the revolute lower joint 222, the cutting guide 190 may be rotated about the PAM 130. When the cutting guide 190 is mounted to the PAM 130, via the mechanical connection 220, and assumes the known registration position (and when the rigid reference 170 is mounted to the patient tissue), data from the IMUs 173, 183 is recorded by the image guided surgical system 100 to establish a point of reference. More specifically, data from the IMUs 173, 183 is processed to determine changes in position and orientation of the cutting guide 190 with respect to the patient bone 162. In this fashion, future motions of the tibia 162 are tracked independently using the IMU 173 of the rigid reference 170, while motions of the cutting guide 190 are tracked separately using the tracking IMU 183. As a result, the image guided surgical system 100 displays a virtual bone model 114 of the tibia along with a visual reference denoting the position and orientation of the cutting slot 200 (that may be color highlighted (e.g., green)) to differentiate between a position of the cutting slot that is or is not consistent with a pre-operative surgical plan establishing the position and orientation of a bone cutting plane.

Because the IMU 183 is rigidly mounted to the guide body 192, changes in the position and orientation of the cutting slot 200 are correspondingly reflected in changes in position and orientation of the IMU 183, which sends its data to the image guided surgical system 100. The image guided surgical system uses the data from the IMU 183, along with knowing the dimensions of the guide body 192 to calculate the position and orientation of the cutting slot 200. As a result, the image guided surgical system 100 may display a virtual bone model 114 of the patient's tibia 162 along with a pair of phantom lines denoting the position and orientation of the cutting slot 200 (that may be color highlighted (e.g., white)) with respect to the position and orientation of the intended cutting slot (that may be color highlighted (e.g., green)) to differentiate between a position and/or orientation of the cutting slot that is or is not consistent with a pre-operative surgical plan establishing the position and orientation of the tibia resection cut. Post registration, the image guided surgical system 100 may be utilized to facilitate the tibia resection cut.

Referring again to FIGS. 39 and 40, the cutting guide 190 may be repositioned with respect to the PAM 130 using one or both of the joints 222, 226. By way of example, the lower revolute joint 222 may be manipulated so as to allow the cutting guide 190 to rotation around the PAM 130 via a rotational axis extending through the bolt/screw 230 in preparation for the distal femoral resection. In exemplary form, the image guided surgical system 100 may be operative to process data from the IMUs 173, 183 and display virtual bone model 114 of the patient's tibia 162 and the relative updated position and orientation of the cutting slot 200 from calculating the relative position and orientation of the cutting guide 190 with respect to the patient's tibia. In the context of the lower joint 222, because only a single revolute joint is used, the one or more visual displays 106 may show a "reachable" region, or the allowable range of proximal tibia that may be cut by manipulating the upper spherical joint. In particular, as discussed herein, using trigonometry, the image guided surgical system 100 the position of the cutting slot 200 using data from the IMUs 173, 183. Upon reaching the appropriate position, as confirmed by the visual displays 106, the surgeon may utilize a surgical saw blade (not shown) extending into the cutting slot 200 in order to remove the proximal section of the tibia. After making the tibia resection cut, the rigid reference 170, PAM 130, mechanical connections 220, and cutting guide 190 may be removed from the surgical site. In the alternative, the rigid reference 170 may be maintained as part of positioning an orthopedic trial or permanent implant.

Figure 41:
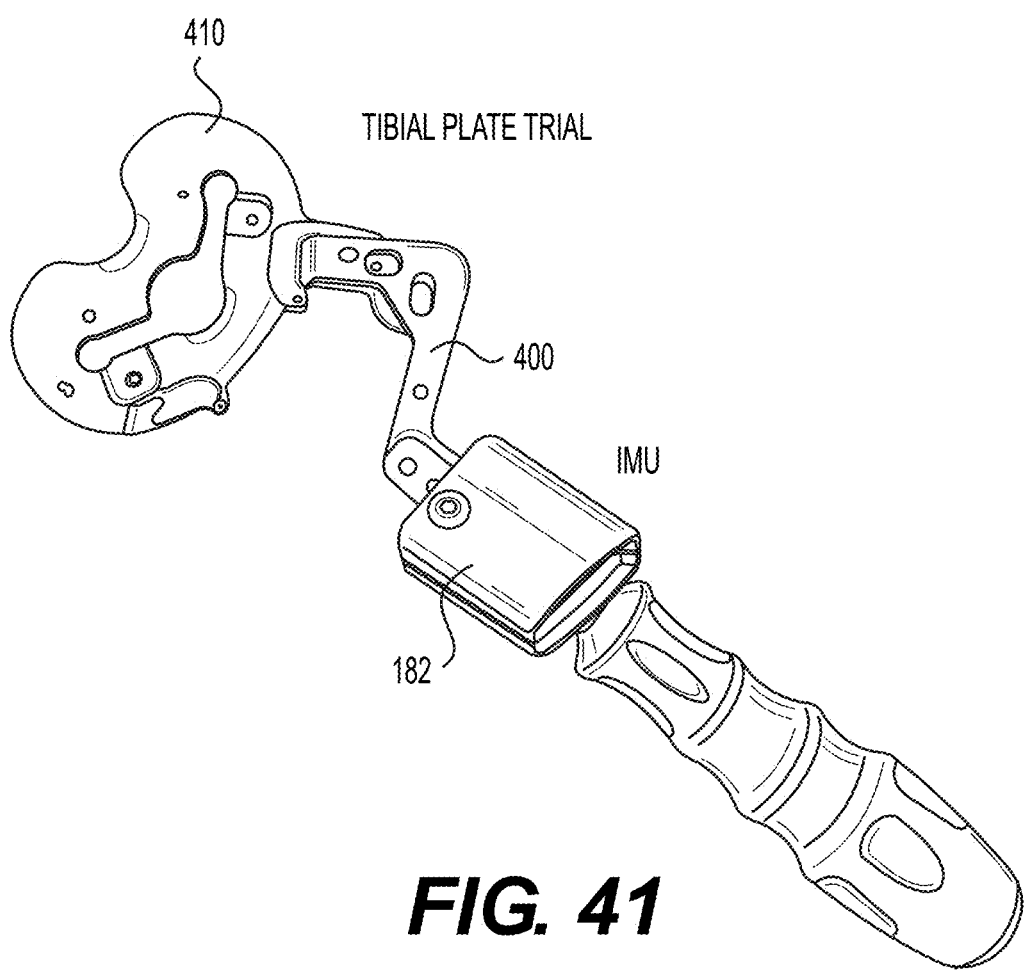
FIG. 41 is an elevated perspective view of an exemplary placement device, mounted to a tibial trial, in accordance with the instant disclosure.

Turning to FIG. 41, it is also within the scope of the disclosure to remove the second inertial measurement device 182 from the cutting guide 190 and mount the inertial measurement device to a placement device 400. In such a circumstance, the second inertial measurement device 182 may be mounted to a placement device 400, to which is mounted an orthopedic trial 410 (e.g., a tibial trial plate) or a final orthopedic implant. It should be noted that while the following example is described with respect to a tibial trail 410, any orthopedic trial or final implant for any joint (e.g., knee, hip, shoulder, ankle, etc.) may be similarly used in conjunction with the placement device 400.

In exemplary form, the placement device 400 has known dimensions and may accept the second inertial measurement device 182 in only a single orientation and position. As a result, the when the second inertial measurement device 182 is mounted to the placement device 400, the image guided surgical system 100 may realize this mounting automatically or rely on a manual input to tell the system that the second inertial measurement device is now mounted to the placement device. Either way, the image guided surgical system 100 uses the registration position and orientation of the second inertial measurement device 182 (when it was mounted to the cutting guide 190) to calculate the position and orientation of the IMU 183 in real-time. Because the position and orientation of the IMU 183 with respect to the second inertial measurement device 182 is constant, and the second inertial measurement device can only be mounted to the placement device 400 in a single position and orientation, by calculating the position and orientation of the IMU, the image guided surgical system 100 is operative to calculate the position and orientation of the placement device 400.

In this exemplary embodiment, the placement device 400 may only be mounted to the orthopedic trial or final implant in a predetermined position and orientation, where the image guided surgical system 100 includes CAD files or similar data for each orthopedic trial or final implant that maybe utilized during the TKA procedure. In this manner, the image guided surgical system 100, by knowing the position and orientation of the placement device, and knowing which orthopedic trial or implant is mounted to the placement device (whether automatically or via manual input), calculates the relative position of the orthopedic trial or implant with respect to the patient bone (e.g., tibia). As a result, the surgeon may be guided as to the position and orientation of the orthopedic trial or implant in accordance with a pre-operative surgical plan. By guiding the surgeon concerning placement and orientation of the final implant and/or orthopedic trail, the surgeon is able to more precisely position and orient the implant/trial. If the implant/trial does not appear to confirm, the surgeon may make professional judgments concerning whether further bone cuts are necessary, whether a different size implant/trail is necessary, and whether a different implant altogether is necessary.

Figure 42:
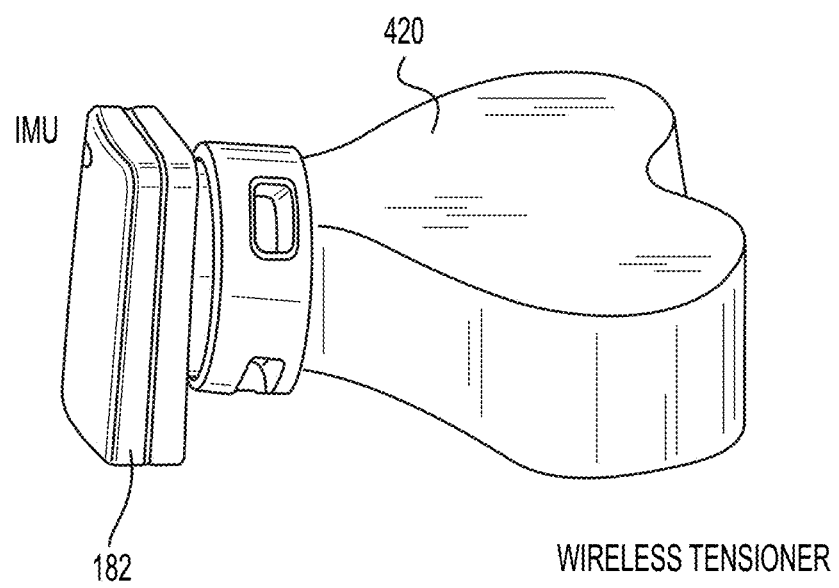
FIG. 42 is an elevated perspective view of a load measurement device in accordance with the instant disclosure.

With reference to FIG. 42, it is also within the scope of the disclosure to remove the second inertial measurement device 182 from the cutting guide 190 (or other surgical device it is mounted to) and mount the inertial measurement device to a tensioning device 420 (while retaining the rigid reference 170 mounted to a patient bone). In this exemplary circumstance, the tensioning device 420 may comprise a wireless tensioner or load measurement device. By way of example, the load measurement device 420 may comprise a multitude of piezoresistive, capacitive, and/or piezoelectric based strain sensors. These sensors may be configured into an array of sensors for mapping the location of high strain on the joint surface. In exemplary form, the load measurement device 420 may have a surface that can be flat or surfaced to match the articulating surface of the joint component. Moreover, the load measurement device 420 may include a microcomputer and/or a wireless transmitter for data communication.

In exemplary form, the load measurement device 420, in the context of TKA, may be placed after the femoral and tibia resection to evaluate the tightness of the joint. As part of evaluating the tightness of the joint, the joint may be taken through a range of motion while an orthopedic trial or the final implant is in place. More specifically, when teamed with IMU data, the load measurement device 420 may provide joint tightness information along with the flexion angles calculated from IMU data, not to mention the overall position and orientation of the device using the IMU data.

In exemplary form, the load measurement device 420 has known dimensions and may accept the second inertial measurement device 182 in only a single orientation and position. As a result, the when the second inertial measurement device 182 is mounted to the load measurement device 420, the image guided surgical system 100 may realize this mounting automatically or rely on a manual input to tell the system that the second inertial measurement device is now mounted to the load measurement device. Either way, the image guided surgical system 100 uses the registration position and orientation of the second inertial measurement device 182 (when it was mounted to the cutting guide 190) to calculate the position and orientation of the IMU 183 in real-time. Because the position and orientation of the IMU 183 with respect to the second inertial measurement device 182 is constant, and the second inertial measurement device can only be mounted to the load measurement device 420 in a single position and orientation, by calculating the position and orientation of the IMU, the image guided surgical system 100 is operative to calculate the position and orientation of the load measurement device 420.

In this exemplary embodiment, the image guided surgical system 100, by knowing the position and orientation of the IMU 182, calculates the relative position of the load measurement device 420 with respect to the patient bone (e.g., tibia). As a result, the surgeon may receive feedback from the load measurement device 420 indicative of whether the joint loading is or is not consistent with a pre-operative surgical plan. By guiding the surgeon concerning joint tightness, the surgeon is able address any concerns by professional judgments concerning whether further bone cuts are necessary, whether a different size implant/trail is necessary, and whether a different implant altogether is necessary.

By way of summary, the exemplary disclosed steps for carrying out a TKA replacement or revision surgery may include one or more of the following, without limitation, in any order: (a) mount PAM 130 to femur 160; (b) mount reference IMU 173 to femur 160; (c) mount instrument IMU 183 to cutting guide 190; (d) register IMUs 173, 183 with respect to one another, where at least one IMU is in a known position with respect to the patient bone 160; (e) reposition the cutting guide 190 with respect to the PAM 130 (femur specific) (that may include repositioning the revolute joints 222, 234 and spherical joint 236) using IMU guidance to position the cutting slot 200 to guide a distal femoral resection cut consistent with a pre-operative surgical plan; (f) make the distal femoral resection cut; (g) reposition the cutting guide 190 with respect to the PAM 130 (tibia specific)(that may include repositioning the revolute joints 222,234 and spherical joint 236) using IMU guidance to position the cutting slot 200 to guide a proximal tibial resection cut consistent with a pre-operative surgical plan; (h) make the proximal tibial resection cut; (i) perform evaluation(s) with guided IMU load measurement device to determine any needed resection alterations and appropriate component rotation; (j) using IMU guidance and using display(s) to show user real-time or near real-time updates on pin positions, posterior resections, anterior notching, internal/external rotation, (1) reposition the cutting guide to 4-in-1 pin position, (2) unlock lower revolute joint, rotate until desired pin proximity is achievable, (3) lock bottom revolute joint, unlock spherical joint and reposition until desired pin position is achievable, (4) lock all joints when acceptable position achieved. (5) drill surgical pin holes, (6) mount surgical pins to resected femur using the drilled holes; (k) remove PAM 130, mechanical connections 220, and cutting guide 190; (l) mount a multi-cut cutting guide to the resected distal femur using the surgical pins as guides; (m) mount a guide foot 260 to the resected distal femur using the surgical pins as guides, where the guide foot is ultimately mounted to a repositionable cutting guide 190; (n) adjust cut slot for each of posterior, posterior chamfer, anterior chamfer and anterior cuts on the distal femur; (o) make each of each of posterior, posterior chamfer, anterior chamfer and anterior cuts on the distal femur (that may include using a surgical saw); (p) position orthopedic trial components on the resected femur and tibia to verify component size and placement position; (q) place final orthopedic components on the resected femur and tibia.

Figure 43:
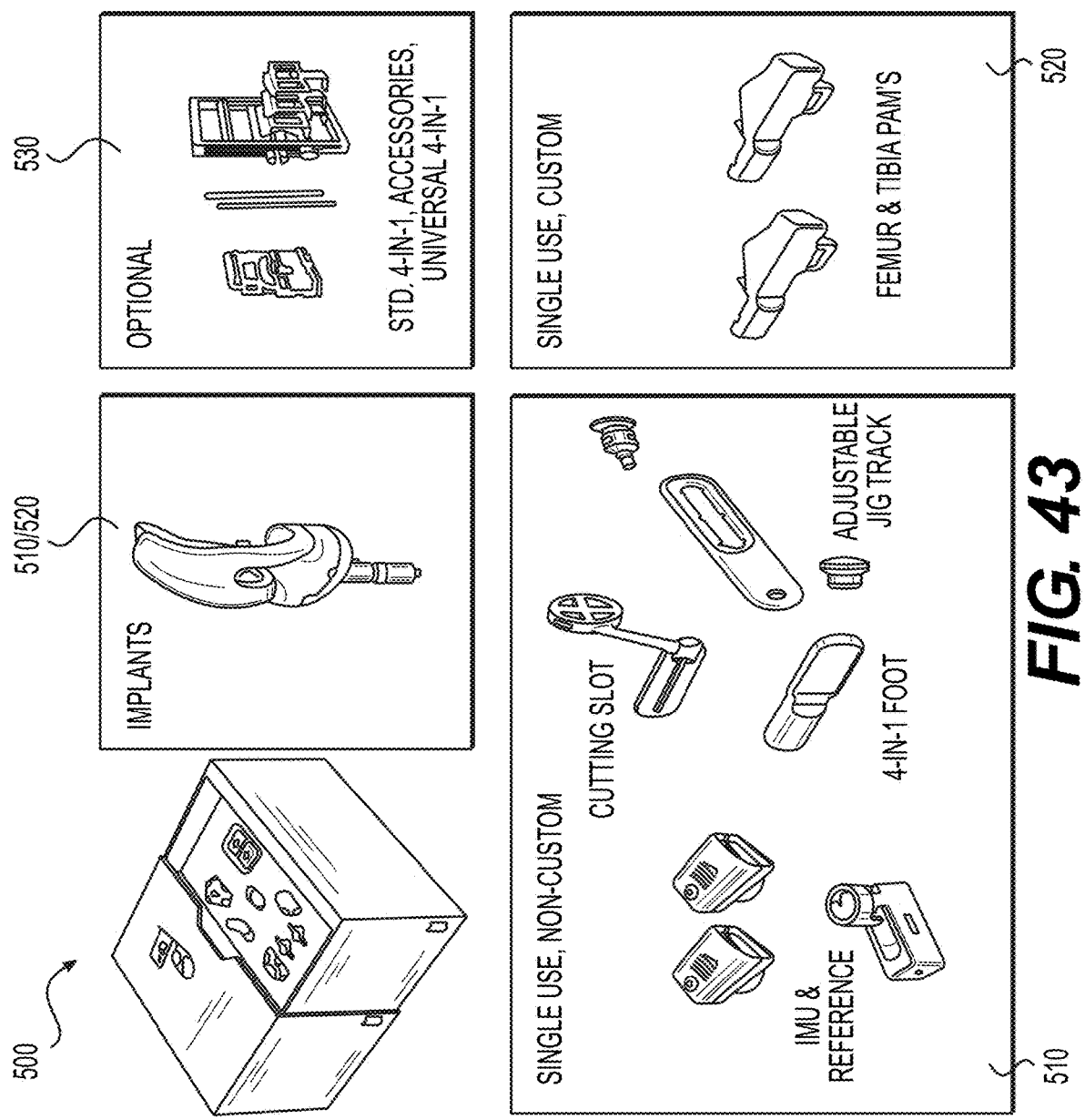
FIG. 43 is a diagram depicting exemplary components that may comprise a surgical kit in accordance with the instant disclosure.

Referring to FIG. 43, it is also within the scope of the instant disclosure to provide a kit 500 that includes one or more of the components disclosed herein, in addition to final orthopedic implants (and optionally trial orthopedic implants). Given the need for instrument and inventory reduction in orthopedic surgery, specifically in primary knee arthroplasty, it is desirable that the kit 500 be deliverable in a "just-in-time" or made-to-order manner to reduce needed shelf space at healthcare facilities and instrument/inventory costs for implant manufacturers. Each component of the kit 500 may be delivered sterile or non-sterile depending on customer requirements.

As part of an exemplary kit 500, the kit may include a non-patient-specific package 510 comprising one or more of the following: two or more IMU devices 172, 182, a rigid reference housing 174, the mechanical connections 220, the cutting guide 190, the guide foot 260, a placement device 400, and a tensioning device 420. The foregoing exemplary package 510 components of the kit 500 are anticipated to be single use (i.e., disposable), but could also be re-sterilized and reused as multi-use components. In this fashion, the kit 500 may or may not include the non-patient-specific package 510, particularly where a surgeon is reusing components from a prior kit. In addition to non-patient-specific components, the kit 500 may include various patient-specific components.

By way of example, the kit 500 may include a patient-specific package 520 comprising one or more of the following: a distal femur PAM 130, a proximal tibia PAM 130, patient-specific orthopedic implants and optionally orthopedic trials (e.g., femoral component, tibial tray, tibial tray insert, etc.). The foregoing exemplary package 520 components of the kit 500 are anticipated to be used for only a single surgical procedure (i.e., disposable).

By way of further example, the kit 500 may include an optional package 530 including components that a surgeon or hospital may anticipate using as part of the surgical procedure, whether or not the components are single use or reusable. In exemplary form, the optional package 530 may include one or more of the following: surgical pins, surgical drill bit(s), static multi-cut bone cutting guide (e.g., 4-in-1 cutting block 300), reconfigurable multi-cut bone cutting guide without navigation, and non-patient-specific orthopedic implants and optionally orthopedic trials (e.g., femoral component, tibial tray, tibial tray insert, etc.). The foregoing exemplary package 530 components of the kit 500 are anticipated to be single use (i.e., disposable), but could also be re-sterilized and reused as multi-use components.

By way of even further example, the kit 500 may include one or more of the packages 510, 520, 530 and, when including a patient-specific package 520, may be manufactured and delivered in a just-in-time fashion. Moreover, as part of the kit, before or at the time of surgery, a surgical plan may be prepared and made available to the surgical navigation software 104, wirelessly or via USB or similar portable memory, and used with the kit 500 components to execute the desired surgical procedure such as, without limitation, TKA.

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A surgical navigation system comprising:
a tibial patient-specific anatomical mapper (PAM) that includes a surface precisely and correctly mating with a tibial surface in only a single location and orientation, where the tibial PAM is configured to be mounted to the tibial surface;
a femoral patient-specific anatomical mapper (PAM) that includes a surface precisely and correctly mating with a femoral surface in only a single location and orientation, where the femoral PAM is configured to be mounted to the femoral surface;
a first inertial measurement unit (IMU) having a gyroscope, a plurality of accelerometers, and a magnetometer;
a first transmitter communicatively coupled to the first IMU;
a second inertial measurement unit (IMU) having a gyroscope, a plurality of accelerometers, and a magnetometer;
a second transmitter communicatively coupled to the second IMU;
a first signal receiver communicatively coupled to the first and second transmitters;
a cutting guide configured to be operatively coupled to at least one of the tibial PAM and the femoral PAM, the guide including at least one of a cutting slot and a pin orifice, the cutting guide configured to couple to the first IMU correctly in only a single position and orientation;
a controller communicatively coupled to the first signal receiver, the controller including software having access to a virtual model of patient anatomy and a pre-operative surgical plan indicating intended resection cuts with respect to the virtual model.

2. The surgical navigation system of claim 1, further comprising a visual display communicatively coupled to the controller, wherein the controller software configured to process data from the first and second IMUs to determine the position and orientation of the cutting guide with respect to the patient anatomy and output instructions for the visual display to visually represent the virtual model of the patient anatomy and provide guidance as to whether the cutting guide is positioned with respect to the patient anatomy consistent with the pre-operative surgical plan to achieve the intended resection cuts.

3. The surgical navigation system of claim 1, wherein the tibial PAM is configured to engage a proximal portion of a tibia and the femoral PAM is configured to engage a distal portion of the femur.

4. The surgical navigation system of claim 1, further comprising a mechanical connection operative to couple the cutting guide to at least one of the tibial PAM and the femoral PAM, the mechanical connection including at least one joint.

5. The surgical navigation system of claim 4, wherein the at least one joint comprises at least two joints.

6. The surgical navigation system of claim 5, wherein the at least two joints include a revolute joint and a spherical joint.

7. The surgical navigation system of claim 5, wherein the at least two joints include a pair of revolute joints.

8. The surgical navigation system of claim 4, wherein the mechanical connection is configured to concurrently mount to a first predetermined location of at least one of the tibial PAM and the femoral PAM and a second predetermined location of the cutting guide to assume a registration position and orientation.

9. The surgical navigation system of claim 1, further comprising a load measuring device configured to couple to the first IMU in a known position and orientation.

10. The surgical navigation system of claim 9, wherein the load measuring device comprises at least one of a plurality of piezoresistive sensors, a plurality of capacitive sensors, and a plurality of piezoelectric based strain sensors.

11. The surgical navigation system of claim 1, further comprising an orthopedic implant placement device configured to couple to the first IMU in a known position and orientation.

12. The surgical navigation system of claim 11, wherein the orthopedic implant placement device is configured to couple to an orthopedic implant in a predetermined location and orientation, where the orthopedic implant comprises at least one of an orthopedic trial and a final orthopedic implant.

13. The surgical navigation system of claim 12, wherein the orthopedic implant comprises at least one of a trial implant and a femoral implant as part of at least one of a knee replacement surgery or a knee revision surgery.

14. The surgical navigation system of claim 2, wherein the visual display comprises a plurality of display windows.

15. The surgical navigation system of claim 14, wherein each of the plurality of display windows is associated with a stand-alone screen.

16. The surgical navigation system of claim 1, further comprising an orthopedic implant comprising at least one of a final orthopedic implant and an orthopedic trial.

17. The surgical navigation system of claim 16, wherein the final orthopedic implant comprises a component of a total knee joint replacement or a partial knee joint replacement.

18. The surgical navigation system of claim 16, wherein the final orthopedic implant comprises at least one of a patient-specific femoral component and a patient-specific tibial component of a total knee replacement.

19. The surgical navigation system of claim 1, further comprising a guide foot configured to be operatively coupled to the cutting guide when the guide foot is mounted to the patient anatomy in order to facilitate at least one bone cut.

20. A method of conducting a surgical procedure, the surgical procedure comprising:
repositioning a cutting guide using navigation guidance displayed on a visual display, the cutting guide including a first inertial measurement unit (IMU), the cutting guide operatively coupled to a femoral patient-specific anatomical mapper (PAM) that includes a surface precisely and correctly mating with a femoral surface in only a single location and orientation, where the navigation guidance includes at least one of a virtual model of the cutting guide and a virtual model of a patient femur, as well as an indication regarding a three dimensional position of the cutting guide with respect to the patient femur using data from the first IMU, where the navigation guidance also includes guidance for repositioning the cutting guide to make a femoral bone cut consistent with a pre-operative surgical plan.

21. The method of claim 20, further comprising:
repositioning the cutting guide using navigation guidance displayed on the visual display, the cutting guide including the first inertial measurement unit (IMU), the cutting guide operatively coupled to a tibial patient-specific anatomical mapper (PAM) that includes a surface precisely and correctly mating with a tibial surface in only a single location and orientation, where the navigation guidance includes at least one of the virtual model of the cutting guide and a virtual model of a patient tibia, as well as an indication regarding the three dimensional position of the cutting guide with respect to the patient tibia using data from the first IMU, where the navigation guidance also includes guidance for repositioning the cutting guide to make a tibial bone cut consistent with the pre-operative surgical plan.

22. The method of claim 20, further comprising:
mounting the femoral PAM surface to the patient femoral surface in the correct single location and orientation;
coupling a second inertial measurement unit (IMU) to the patient femur; and,
registering the first and second IMUs with respect to one another.

23. The method of claim 20, further comprising:
mounting the tibial PAM surface to the patient tibial surface in the correct single location and orientation;
coupling a second inertial measurement unit (IMU) to the patient tibia; and,
registering the first and second IMUs with respect to one another.

24. The method of claim 20, wherein the navigation guidance includes only the virtual model of the cutting guide.

25. The method of claim 20, wherein the navigation guidance includes only the virtual model of the patient femur.

26. The method of claim 21, wherein the navigation guidance includes at least one of the virtual model of the patient femur and the virtual model of the patient tibia, in addition to a first cutting line representing the real-world position of the cutting guide and a second cutting line representing an intended pre-operative plan position of the cutting guide for making at least one of the femoral bone cut and the tibial bone cut.

27. The method of claim 21, further comprising:
making the femoral bone cut using a surgical saw guided by the cutting guide;
repositioning the cutting guide using navigation guidance displayed on the visual display, the cutting guide including the first inertial measurement unit (IMU) and being operatively coupled to the femoral patient-specific anatomical mapper (PAM), where the navigation guidance includes at least one of the virtual model of the cutting guide and the virtual model of the patient femur, as well as an indication regarding the three dimensional position of the cutting guide with respect to the patient femur using data from the first IMU, where the navigation guidance also includes guidance for repositioning the cutting guide to make a subsequent femoral bone cut consistent with the pre-operative surgical plan.

28. The method of claim 21, further comprising:
making the femoral bone cut using a surgical saw guided by the cutting guide, where the femoral bone cut is a distal resection; and,
repositioning the cutting guide using navigation guidance displayed on the visual display, the cutting guide including the first inertial measurement unit (IMU) and being operatively coupled to the femoral patient-specific anatomical mapper (PAM), where the navigation guidance includes at least one of the virtual model of the cutting guide and the virtual model of the patient femur, as well as an indication regarding the three dimensional position of the cutting guide with respect to the patient femur using data from the first IMU, where the navigation guidance also includes guidance for repositioning the cutting guide to drill holes into the resected femur consistent with the me-operative surgical plan.

29. The method of claim 28, further comprising:
drilling holes into the resected femur femoral bone using a surgical drill guided by the cutting guide;
inserting surgical pins into the drill holes;
repositioning a 4-in-1 cutting guide against the resected femur using the inserted surgical pins for alignment; and,
making at least one femoral resection cut using guidance from the 4-in-1 cutting guide.

30. The method of claim 28, further comprising:
drilling holes into the resected femur femoral bone using a surgical drill guided by the cutting guide;
inserting surgical pins into the drill holes;
repositioning a fixed position cutting guide against the resected femur using the inserted surgical pins for alignment; and,
making at least one femoral resection cut using guidance from the fixed position cutting guide.

* * * * *